(12) United States Patent
Blaser et al.

(10) Patent No.: US 9,386,793 B2
(45) Date of Patent: Jul. 12, 2016

(54) COMPOSITIONS AND METHODS FOR TREATING OBESITY AND RELATED DISORDERS BY CHARACTERIZING AND RESTORING MAMMALIAN BACTERIAL MICROBIOTA

(75) Inventors: Martin J. Blaser, New York, NY (US); Laura Cox, Brooklyn, NY (US); Ilseung Cho, New York, NY (US)

(73) Assignee: New York University, New York, NY (US)

( * ) Notice: Subject to any disclaimer, the term of this patent is extended or adjusted under 35 U.S.C. 154(b) by 841 days.

(21) Appl. No.: 13/214,034

(22) Filed: Aug. 19, 2011

(65) Prior Publication Data

US 2012/0058094 A1  Mar. 8, 2012

Related U.S. Application Data

(60) Provisional application No. 61/375,678, filed on Aug. 20, 2010.

(51) Int. Cl.
| | |
|---|---|
| *A61K 35/74* | (2015.01) |
| *A23L 1/30* | (2006.01) |
| *A61K 35/741* | (2015.01) |

(52) U.S. Cl.
CPC .................. *A23L 1/30* (2013.01); *A23L 1/3014* (2013.01); *A61K 35/741* (2013.01)

(58) Field of Classification Search
CPC ....... A61K 35/741; A23L 1/30; A23L 1/3014
See application file for complete search history.

(56) References Cited

U.S. PATENT DOCUMENTS

| | | |
|---|---|---|
| 2001/0001711 A1 | 5/2001 | Olshenitsky et al. |
| 2002/0048567 A1 | 4/2002 | Olshenitsky et al. |
| 2002/0048568 A1 | 4/2002 | Olshenitsky et al. |
| 2002/0048569 A1 | 4/2002 | Olshenitsky et al. |
| 2002/0048570 A1 | 4/2002 | Olshenitsky et al. |
| 2002/0051772 A1 | 5/2002 | Olshenitsky et al. |
| 2002/0051773 A1 | 5/2002 | Olshenitsky et al. |
| 2002/0051774 A1 | 5/2002 | Olshenitsky et al. |
| 2002/0051775 A1 | 5/2002 | Olshenitsky et al. |
| 2002/0051776 A1 | 5/2002 | Olshenitsky et al. |
| 2002/0054866 A1 | 5/2002 | Olshenitsky et al. |
| 2002/0054867 A1 | 5/2002 | Olshenitsky et al. |
| 2002/0054868 A1 | 5/2002 | Olshenitsky et al. |
| 2002/0071835 A1 | 6/2002 | Olshenitsky et al. |
| 2004/0028689 A1 | 2/2004 | Borody |
| 2004/0052909 A1 | 3/2004 | Contento et al. |
| 2004/0265291 A1 | 12/2004 | Drake et al. |
| 2005/0037089 A1 | 2/2005 | Jobbins |
| 2005/0176001 A1 | 8/2005 | Nakano et al. |
| 2006/0088514 A1 | 4/2006 | O'Mahony et al. |
| 2007/0009577 A1 | 1/2007 | Mankovitz |
| 2009/0035329 A1 | 2/2009 | Blaser et al. |
| 2010/0074872 A1 | 3/2010 | Blaser et al. |
| 2010/0172874 A1 | 7/2010 | Turnbaugh et al. |
| 2011/0280840 A1 | 11/2011 | Blaser et al. |
| 2012/0171193 A1 | 7/2012 | Blaser et al. |

FOREIGN PATENT DOCUMENTS

| | | | |
|---|---|---|---|
| EP | 1886680 | | 2/2008 |
| WO | WO9734591 | * | 9/1997 ............ A61K 31/75 |
| WO | 00/75284 A1 | | 12/2000 |
| WO | 01/15715 A2 | | 3/2001 |
| WO | 2009/018447 A2 | | 2/2009 |
| WO | WO 2012/024638 | | 2/2012 |

OTHER PUBLICATIONS

Holzapfel et al., "Overview of gut flora and probiotics," Int J Food Microbiol 41:85-101, 1998.
Tuohy et al, "Using probiotics and prebiotics to improve gut health," Therapeutic Focus 8(15):692-700, 2003.
International Search Report issued in International Appl. No. PCT/US2011/048501 mailed Mar. 13, 2012.
Armougom et al., "Use of pyrosequencing and DNA barcodes to monitor variations in Firmicutes and Bacteroidetes communities in the gut microbiota of obese humans", BMC Genomics, vol. 9:576, 2008.
Armougom et al., "Monitoring Bacterial Community of Human Gut Microbiota Reveals an Increase in Lactobacillus in Obese Patients and Methanogens in Anorexic Patients", PLoS One, vol. 4(9):e7125, 2009.
Li et al., "Symbiotic gut microbes modulate human metabolic phenotypes", Proc. Natl. Acad. Sci. USA, vol. 105:2117-2122, 2008.
Hong Hye Jin et al, "Differential suppression of allergen-induced airway inflammation in murine model of asthma by lactic acid bacteria", FASEB Journal, vol. 22, 2008, abstract.
Stockert K, "Physiological intestinal flora in children of 6 to 12 years of age with bronchial asthma", Deutsche Zeitschrift Fur Akupunktur 2001 DE, vol. 44, No. 4, 2001, pp. 268-271 (English abstract provided).
Morris et al, "Helicobacter pylori infection link to lower rates of asthma", Lancet Infectious Diseases, Elsevier Ltd., US, vol. 7, No. 6, 2007, p. 379.
Extended European Search Report, dated Feb. 28, 2013, which issued during the prosecution of European Patent Application No. 09816896.6.
Andersson et al., Comparative analysis of human gut microbiota by barcoded pyrosequencing, PLoS One, vol. 3 Issue 7, e2836, pp. 1-8, 2008.
Bartosch, et al., Characterization of bacterial communities in feces from healthy elderly volunteers and hospitalized elderly patients by using real-time PCR and effects of antibiotic treatment on the fecal microbiota, Applied and Environmental Microbiology, vol. 70, No. 6, pp. 3575-3581, 2004.

(Continued)

*Primary Examiner* — Taeyoon Kim
*Assistant Examiner* — Tiffany Gough
(74) *Attorney, Agent, or Firm* — Troutman Sanders LLP

(57) ABSTRACT

The present invention relates to characterizing changes in mammalian intestinal microbiota associated with associated with high-fat and low-fat diets and with diets containing hydroxypropylmethylcellulose (HPMC) and related methods for diagnosing, preventing and treating obesity and related conditions such as metabolic syndrome and diabetes mellitus. Therapeutic methods of the invention involve the use of probiotics, and/or prebiotics, and/or narrow spectrum antibiotics/anti-bacterial agents that are capable of restoring healthy mammalian bacterial intestinal microbiota.

7 Claims, 26 Drawing Sheets

(56) References Cited

OTHER PUBLICATIONS

Blaser et al., Does Helicobacter pylon protect against asthma and allergy? Gut, vol. 57, pp. 561-567, 2008.
Chen et al., Helicobacter pylon Colonization Is Inversely Associated with Childhood Asthma, Journal of Infectious Diseases, vol. 198, pp. 553-560, 2008.
Cho et al., Antibiotics in early life alter the murine colonic microbiome and adiposity, Nature, vol. 488, pp. 621-626, 2012.
Duncan et al., Cultivable bacterial diversity from the human colon, Letters in Applied Microbiology, vol. 44, pp. 343-350, 2007.
Eckburg et al., Diversity of the Human Intestinal Microbial Flora, Science, vol. 308, pp. 1635-1638, 2005.
Flint, Antibiotics and adiposity, Nature, vol. 488, pp. 601-602, 2012.
Flint, The significance of prokaryote diversity in the human gastrointestinal tract, *In* SGM symposium 66: Prokaryotic Diversity: mechanisms and significance, Logan et al., eds., Cambridge University Press, pp. 65-90, 2012.
Fuller, Probiotics in man and animals, J. Applied Bacteriol., vol. 66, pp. 365-378, 1989.
Gao et al., Molecular analysis of human forearm superficial skin bacterial biota, Proc. Natl. Acad. Sci. USA, vol. 104, pp. 2927-2932, 2007.
Gao et al., Substantial Alterations of the Cutaneous Bacterial Biota in Psoriatic Lesions, PLoS One, vol. 3, pp. e2719-e2728, 2008.
Hopkins, et al., Age and disease related changes in intestinal bacterial populations assessed by cell culture, 16S rRNA abundance, and community cellular fatty acid profiles, Gut, vol. 48, pp. 198-205, 2001.
International Preliminary Report on Patentability issued in International Appl. No. PCT/US2009/058351, dated Mar. 29, 2011.
International Search Report issued in International Appl. No. PCT/US2009/058351, dated May 10, 2010.
Ley et al., Microbial ecology: Human gut microbes associated with obesity, Nature, vol. 444, pp. 1022-1023, 2006.
Ley et al., Obesity alters gut microbial ecology, Proc. Natl. Acad. Sci. USA, vol. 102, pp. 11070-11075, 2005.
Paulino et al., Molecular Analysis of Fungal Microbiota in Samples from Healthy Human Skin and Psoriatic Lesions, J Clin Microbiol, vol. 44, pp. 2933-2941, 2006.
Ray, Adding weight to the microbiota's role in obesity-exposure to antibiotics early in life can lead to increased adiposity, Nature Reviews/Gastroenterology & Hepatology, vol. 9, 2012.
Sonnerburg et al. Genomic and metabolic studies of the impact of probiotics on a model gut symbiont and host, PLoS Biol, vol. 4(12): e413, pp. 2213-2226, 2006.
Trasande et al, Infant antibiotic exposures and early-life body mass, International Journal of Obesity, advance online publication, pp. 1-8, (doi:10.1038/ijo.2012.132), 2012.
Turnbaugh et al., An obesity-associated gut microbiome with increased capacity for energy harvest, Nature, vol. 444, pp. 1027-1031, 2006.
Wade, Unculturable bacteria—the uncharacterized organisms that cause orl infections, Journal of the Royal Society of Medicine, vol. 95, pp. 81-83, 2002.
Wen et al., Innate immunity and intestinal microbiota in the development of Type 1 diabetes, Nature, vol. 455, pp. 1109-1113, 2008.
Wilson et al., Applications of molecular ecology in the characterization of uncultured microorganisms associated with human disease, Reviews in Medical Microbiology, vol. 8, pp. 91-101, 1997.
Written Opinion of International Searching Authority issued in International Appl. No. PCT/US2009/058351, dated May 10, 2010.
Written Opinion of International Searching Authority issued in International Appl. No. PCT/US2011/048501, dated Mar. 13, 2012.
Zoetendal, et al., High-throughput diversity and functionality analysis of the gastrointestinal tract microbiota, Gut, vol. 57, pp. 1605-1615, 2008.
Hemarajata, P. & Versalovic, J. Effects of probiotics on gut microbiota: mechanisms of intestinal immunomodulation and neuromodulation. Therapeutic Advances in Gastroenterology 6(1), 39-51, doi:10.1177/1756283X12459294 (2013).
Rauch, M. & Lynch, S. Probiotic manipulation of the gastrointestinal microbiota. Gut Microbes 1(5), 335-338, doi:10.4161/gmic.1.5. 13169 (2010).
O'Toole, P. W. & Cooney, J. C. Probiotic Bacteria Influence the Composition and Function of the Intestinal Microbiota. Interdisciplinary Perspectives on Infectious Diseases, 1-9, doi:10.1155/2008/175285 (2008).
Pieper, R. et al. Effect of a single oral administration of Lactobacillus plantarum DSMZ 8862/8866 before and at the time point of weaning on intestinal microbial communities in piglets. International Journal of Food Microbiology 130, 227-232, doi:10.1016/j.ijfoodmicro. 2009.01.026 (2009).
Cox, M. J. et al. Lactobacillus casei Abundance Is Associated with Profound Shifts in the Infant Gut Microbiome. PLoS One 5(1), e8745, doi:10.1371/journal.pone.0008745 (2010).
Kwok, L. et al. The impact of oral consumption of Lactobacillus plantarum P-8 on faecal bacteria revealed by pyrosequencing. Beneficial Microbes, 6(4), 405-413 (2015).

* cited by examiner

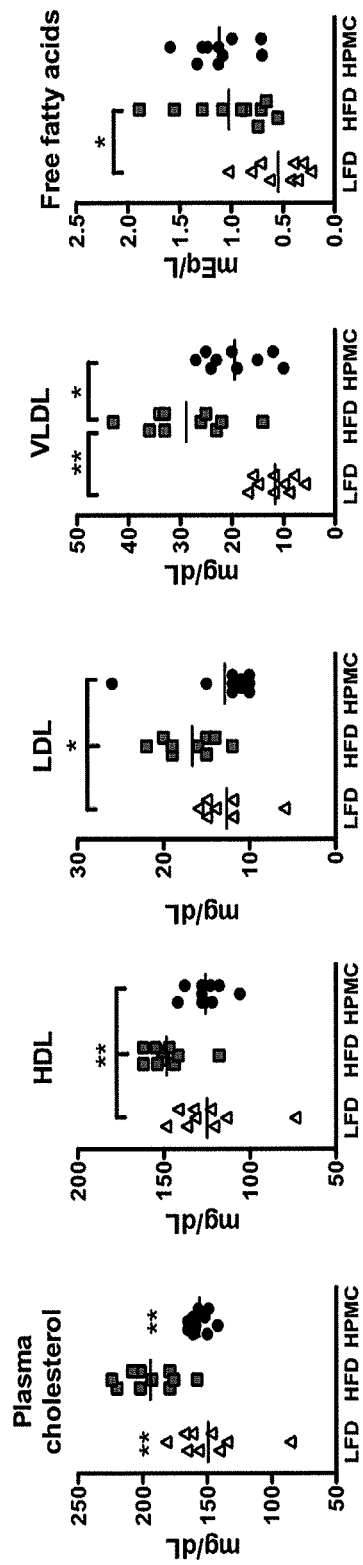
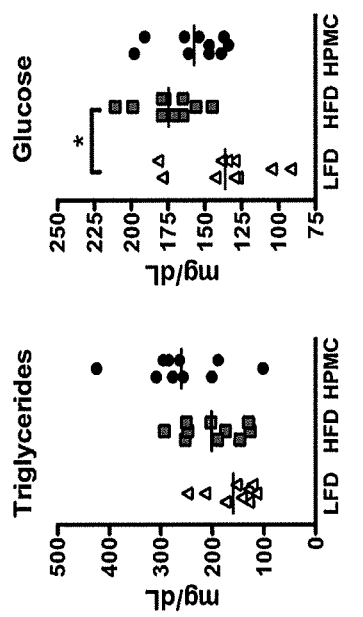

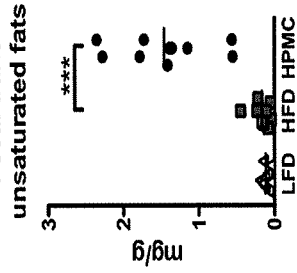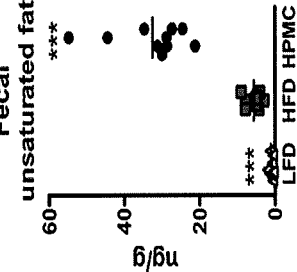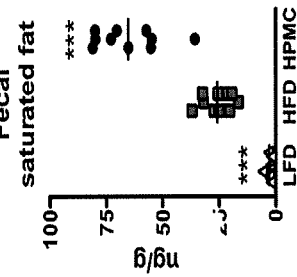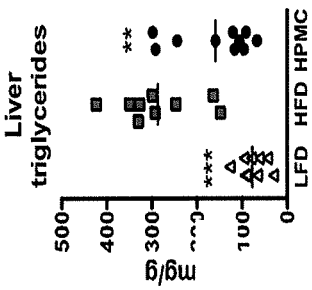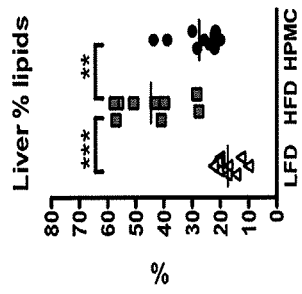

FIG. 4A  Cecal Microbiota

| HPMC induced changes in cecal microbiota compared to 60% fat (DIO) diet | | | | |
|---|---|---|---|---|
| Phylum | Class | Order | Family | Genus |
| ↓ Firmicutes[a] | ↑ Erysipelotrichi | ↑ Erysipelotrichales | ↑ Erysipelotrichaceae | ↑ *Coprobacillus* |
| | | | | ↑ *Holdemania* |
| | ↓ Clostridia | ↓ Clostridiales | ↑ Peptostreptococcaceae | ↑ *Sporacetigenium* |
| | | | ↓ Ruminococcaceae | ↓ *Oscillibacter* |
| | | | ↓ Lachnospiraceae | ↓ *Johnsonella* |
| | | | | ↑ *Dorea* |
| | | | ↑ Incertae Sedis XIV | ↑ *Blautia* |
| | ↑ Bacilli | ↑ Lactobacillales | ↑ Enterococcaceae | ↑ *Enterococcus* |

| 10% fat (low fat) induced changes in cecal microbiota compared to 60% fat (DIO) diet | | | | |
|---|---|---|---|---|
| Phylum | Class | Order | Family | Genus |
| | ↑ Erysipelotrichi | ↑ Erysipelotrichales | ↑ Erysipelotrichaceae | ↓ *Coprobacillus* |
| | | | | ↓ *Papillibacter* |
| | | | | ↑ *Dorea* |

| Alterations in 60% + HPMC diet cecal microbiota compared to 10% kCal fat | | | | |
|---|---|---|---|---|
| Phylum | Class | Order | Family | Genus |
| ↓ Firmicutes | ↑ Erysipelotrichi | ↑ Erysipelotrichales | ↑ Erysipelotrichaceae | ↑ *Coprobacillus* |
| | | | | ↑ *Holdemania* |
| | ↓ Clostridia | ↓ Clostridiales | ↑ Peptostreptococcaceae | ↑ *Sporacetigenium* |
| | | | ↓ Ruminococcaceae | ↓ *Oscillibacter* |
| | | | | ↑ *Anaerotruncus* |
| | | | ↓ Lachnospiraceae | ↓ *Johnsonella* |
| | | | | ↑ *Dorea* |
| | ↑ Bacilli | ↑ Lactobacillales | | |
| ↑ Bacteroidetes | ↑ Bacteroidia | ↑ Bacteroidales | | |

▨ = significantly increased taxa, ▨ = significantly decreased taxa,
P < 0.05 by Mann-Whitney U Test aShown by qPCR

FIG. 4B

| Family Hierarchical Clustering | | | | Chi² | Fisher's Exact Test | | |
|---|---|---|---|---|---|---|---|
| Baseline | HFD | LFD | HPMC | | HFD v LFD | HFD v HPMC | LFD v HPMC |
| Top Branch | 9 | 6 | 9 | 0.1534 | 0.3034 | 1 | 0.3034 |
| Bottom Branch | 1 | 4 | 1 | | | | |
| 2 week fecal | HFD | LFD | HPMC | | | | |
| Top Branch | 10 | 4 | 1 | 0.0004 | 0.0108 | 0.0001 | 0.3034 |
| Bottom Branch | 0 | 6 | 8 | | | | |
| 4 week fecal | HFD | LFD | HPMC | | | | |
| Top Branch | 0 | 8 | 9 | <0.0001 | 0.0007 | 0.0001 | 1 |
| Bottom Branch | 10 | 2 | 1 | | | | |
| 4 week cecal | HFD | LFD | HPMC | | | | |
| Top Branch | 9 | 10 | 0 | <0.0001 | 1 | <0.0001 | <0.0001 |
| Bottom Branch | 0 | 0 | 10 | | | | |
| 4 week ileal | HFD | LFD | HPMC | | | | |
| Top Branch | 9 | 3 | 5 | 0.0228 | 0.0198 | 0.2745 | 0.3416 |
| Bottom Branch | 1 | 7 | 3 | | | | |

FIG. 19

COMPOSITIONS AND METHODS FOR TREATING OBESITY AND RELATED DISORDERS BY CHARACTERIZING AND RESTORING MAMMALIAN BACTERIAL MICROBIOTA

CROSS REFERENCE TO RELATED APPLICATIONS

This application claims the benefit of U.S. Provisional Patent Application No. 61/375,678, filed Aug. 20, 2010, which is incorporated herein by reference in its entirety.

STATEMENT REGARDING FEDERALLY SPONSORED RESEARCH

Research and development leading to certain aspects of the present invention were supported, in part, by grants 1UL1RR029893 and R01DK098989 from the National Institutes of Health. Accordingly, the U.S. government may have certain rights in the invention.

FIELD OF THE INVENTION

The present invention relates to characterizing changes in mammalian intestinal microbiota associated with high-fat and low-fat diets and with diets containing hydroxypropylmethylcellulose (HPMC) and related methods for diagnosing, preventing and treating obesity and related conditions such as metabolic syndrome and diabetes mellitus. Therapeutic methods of the invention involve the use of probiotics, and/or prebiotics, and/or narrow spectrum antibiotics/anti-bacterial agents that are capable of restoring healthy mammalian bacterial intestinal microbiota.

BACKGROUND OF THE INVENTION

Obesity has become widespread with increases in prevalence across all developed nations (Bouchard, C (2000) *N Engl J. Med.* 343, 1888-9). According to the Center for Disease Control (CDC), over 60% of the United States population is overweight, and greater than 30% are obese. For affected persons, the problem often begins in childhood, and continues for life. Major contributors are believed to be increased consumption of high calorie foods and a more sedentary life style. However, neither of these alone or together are sufficient to explain the rise in obesity and subsequent or concomitant obesity-related disorders, such as, e.g., type II diabetes mellitus, metabolic syndrome, hypertension, cardiac pathology, and non-alcoholic fatty liver disease. According to the National Institute of Diabetes, Digestive and Kidney Diseases (NIDDK) approximately 280,000 deaths annually are directly related to obesity. The NIDDK further estimated that the direct cost of healthcare in the U.S. associated with obesity is $51 billion. In addition, Americans spend $33 billion per year on weight loss products. The prevalence of obesity continues to rise at alarming rates.

It is estimated that between 20-25% of American adults (about 47 million) have metabolic syndrome, a complex condition associated with an increased risk of vascular disease. Metabolic syndrome is also known as Syndrome X, metabolic syndrome X, insulin resistance syndrome, or Reaven's syndrome. Metabolic syndrome is generally believed to be a combination of disorders that affect a large number of people in a clustered fashion. The symptoms and features of the syndrome include at least three of the following conditions: diabetes mellitus type II; impaired glucose tolerance or insulin resistance; high blood pressure; central obesity and difficulty losing weight; high cholesterol; combined hyperlipidemia; including elevated LDL; decreased HDL; elevated triglycerides; and fatty liver (especially in concurrent obesity). Insulin resistance is typical of metabolic syndrome and leads to several of its features, including glucose intolerance, dyslipidemia, and hypertension. Obesity is commonly associated with the syndrome as is increased abdominal girth, highlighting the fact that abnormal lipid metabolism likely contributes to the underlying pathophysiology of metabolic syndrome.

Metabolic syndrome was codified in the United States with the publication of the National Cholesterol Education Program Adult Treatment Panel III (ATP III) guidelines in 2001. On a physiologic basis, insulin resistance appears to be responsible for the syndrome. However, insulin resistance can be defined in a myriad of different ways, including impaired glucose metabolism (reduced clearance of glucose and/or the failure to suppress glucose production), the inability to suppress lipolysis in tissues, defective protein synthesis, altered cell differentiation, aberrant nitric oxide synthesis affecting regional blood flow, as well as abnormal cell cycle control and proliferation, all of which have been implicated in the cardiovascular disease associated with metabolic syndrome. At least at present, there is no obvious molecular mechanism causing the syndrome, probably because the condition represents a failure of one or more of the many compensatory mechanisms that are activated in response to energy excess and the accumulation of fat.

Individuals at risk for metabolic syndrome include those who exhibit central obesity with increased abdominal girth (due to excess visceral adiposity) of about more than 35 inches in women and more than 40 inches in men. Individuals at risk for metabolic syndrome also include those that have a BMI greater than or equal to 30 kg/M2 and may also have abnormal levels of nonfasting glucose, lipids, and blood pressure.

Although certain bacterial associations have been examined for these and related conditions, the role of bacterial microbiota in these conditions has not been clearly understood or appreciated. Thus, there remains a need for methods for diagnosing, treating and preventing conditions such as obesity, metabolic syndrome, insulin-deficiency or insulin-resistance related disorders, glucose intolerance, diabetes mellitus, non-alcoholic fatty liver, abnormal lipid metabolism, atherosclerosis, and related disorders.

The average human body, consisting of about $10^{13}$ cells, has about ten times that number of microorganisms. The $10^{14}$ microbes that live in and on each of our bodies belong to all three domains of life on earth—bacteria, archaea and eukarya. The major sites for our indigenous microbiota are the intestinal tract, skin and mucosal surfaces such as nasal mucosa and vagina as well as the oropharynx. By far, the largest bacterial populations are in the colon. Bacteria make up most of the flora in the colon and 60% of the dry mass of feces. Probably more than 1000 different species live in the gut. However, it is probable that >90% of the bacteria come from less than 50 species. Fungi and protozoa also make up a part of the gut flora, but little is known about their activities. While the microbiota is highly extensive, it is barely characterized. Consequently, the Roadmap of the National Institutes of Health (NIH) includes the "Human Microbiome Project" to better characterize our microbial communities and the genes that they harbor (our microbiome) and better understand its relation to both human health and disease. Reviewed in Dethlefsen et al., Nature, 2007, 449:811-818; Turnbaugh et al., Nature, 2007, 449:804-810; Ley et al., Cell, 2006, 124: 837-848.

Studies show that the relationship between gut flora and humans is not merely commensal (a non-harmful coexistence), but rather often is a mutualistic, symbiotic relationship. Although animals can survive with no gut flora, the microorganisms perform a host of useful functions, such as training the immune system, preventing growth of harmful species, regulating the development of the gut, fermenting unused energy substrates, metabolism of glycans and amino acids, synthesis of vitamins (such as biotin and vitamin K) and isoprenoids, biotransformation of xenobiotics, and producing hormones to direct the host to store fats. See, e.g., Gill et al., Science. 2006, 312:1355-1359; Zaneveld et al., Curr. Opin. Chem. Biol., 2008, 12(1):109-114; Guarner, Digestion, 2006, 73:5-12; Li et al., Proc. Natl. Acad. Sci. USA, 2008, 105: 2117-2122; Hooper, Trends Microbiol., 2004, 12:129-134; Mazmanian et al., Cell, 2005, 122:107-118; Rakoff-Nahoum et al., Cell, 2004, 118:229-241. It is therefore believed that changes in the composition of the gut microbiota could have important health effects (Dethlefsen et al., PLoS Biology, 2008, 6(11):2383-2400). Indeed, a correlation between obesity and changes in gut microbiota has been observed (Ley et al., Proc Natl Acad Sci USA, 2005; 102:11070-11075; Backhed et al., Proc Natl Acad Sci USA, 2004; 101:15718-15723). Furthermore, in certain conditions, some microbial species are thought to be capable of directly causing disease by causing infection or increasing cancer risk for the host (O'Keefe et al., J. Nutr. 2007; 137:175 S-182S; McGarr et al., J Clin Gastroenterol., 2005; 39:98-109).

Substantial number of species in vertebrate microbiota is very hard to culture and analyze via traditional cultivation-based studies (Turnbaugh et al., Nature, 2007, 449:804-810; Eckburg et al., Science, 2005, 308:1635-1638). In contrast, broad-range PCR primers targeted to highly conserved regions makes possible the amplification of small subunit rRNA gene (16S rDNA) sequences from all bacterial species (Zoetendal et al., (2006) *Mol Microbiol* 59, 1639-1650), and the extensive and rapidly growing 16S rDNA database facilitates identification of sequences to the species or genus level (Schloss and Handelsman, (2004) *Microbiol Mol Biol Rev* 68, 686-691). Such techniques can also be used for identifying bacterial species in complex environmental niches (Smit et al., (2001) *Appl Environ Microbiol* 67, 2284-2291), including the human mouth, esophagus, stomach, intestine, feces, skin, and vagina, and for clinical diagnosis (Harris and Hartley, (2003) *J Med Microbiol* 52, 685-691; Saglani et al., (2005) *Arch Dis Child* 90, 70-73).

Much of the microbiota is conserved from human to human, at least at the level of phylum and genus (for a general description of human microbiota see, e.g., Turnbaugh et al., Nature 2007; 449:804-810; Ley et al., Nature 2006; 444: 1022-1023; Gao et al., Proc Natl Acad Sci USA 2007; 104: 2927-32; Pei et al., Proc Natl Acad Sci USA 2004; 101:4250-4255; Eckburg et al., Science 2005; 308:1635-1638; Bik et al., Proc Natl Acad Sci USA 2006; 103:732-737). A major source of the human microbiota is from one's mother (for a summary of typical maternal colonization patterns see, e.g., Palmer et al., Plos Biology 2007; 5:e177; Raymond et al., Emerg Infect Dis 2004; 10:1816-21), and to a lesser extent from one's father and siblings (for examples of typical colonization patterns see, e.g., Raymond et al., Emerg Infect Dis 2004; 10:1816-21; Raymond et al., Plos One 2008; 3:e2259; Goodman et al., Am J Epidemiol 1996; 144:290-299; Goodman et al., Lancet 2000; 355:358-362). However, many of the natural mechanisms for the transmission of these indigenous organisms across generations and between family members have diminished with socioeconomic development. The impediments include: childbirth by caesarian section, reduced breast-feeding, smaller family size (fewer siblings), reduced household crowding with shared beds, utensils, indoor plumbing.

It has been known for more than 50 years that the administration of low doses of antibiotics promotes the growth of farm animals. See, e.g., Jukes, Bioscience 1972; 22: 526-534; Jukes (1955) *Antibiotics in Nutrition*. New York, N.Y., USA: Medical Encyclopedia; Feighner and Dashkevicz, Appl. Environ. Microbiol., 1987, 53: 331-336; McEwen and Fedorka-Cray, Clin. Infect. Dis., 2002, 34 (Suppl 3): S93-S106).

The mechanism for this widespread phenomenon has not been established but because of the activity of anti-bacterial but not anti-fungal agents, it can be ascertained to be anti-bacterial.

The vertebrate intestinal tract has a rich component of cells involved in immune responses. The nature of the microbiota colonizing experimental animals or humans affects the immune responses of the populations of reactive host cells (see, e.g., Ando et al., Infection and Immunity 1998; 66:4742-4747; Goll et al., Helicobacter. 2007; 12:185-92; Lundgren et al., Infect Immun. 2005; 73:523-531).

The vertebrate intestinal tract also is a locus in which hormones are produced. In mammals, many of these hormones related to energy homeostasis (including insulin, glucagon, leptin, and ghrelin) are produced by organs of the intestinal tract (see, e.g., Mix et al., Gut 2000; 47:481-6; Kojima et al., Nature 1999; 402:656-60; Shak et al., Obesity Surgery 2008; 18(9):1089-96; Roper et al., Journal of Clinical Endocrinology & Metabolism 2008; 93:2350-7; Francois et al., Gut 2008; 57:16-24; Cummings and Overduin, J Clin Invest 2007; 117:13-23; Bado et al., Nature 1998; 394:790-793).

Changing of the microbiota of the intestinal tract appears to affect the levels of some of these hormones (see, e.g., Breidert et al., Scand J Gastroenterol 1999; 34:954-61; Liew et al., Obes. Surg. 2006; 16:612-9; Nwokolo et al., Gut. 2003; 52, 637-640; Kinkhabwala et al., Gastroenterology 132:A208). The hormones affect immune responses (see, e.g., Matarese et al., J Immunol 2005; 174:3137-3142; Matsuda et al., J. Allergy Clin. Immunol. 2007; 119, 5174) and adiposity (see, e.g., Tschop et al., Nature 2000; 407:908-13).

Hydroxypropylmethylcellulose (HPMC) is modified cellulose fiber that produces viscous solutions in the gastrointestinal tract. It has been demonstrated that high viscosity (HV) HPMC consumed as part of a meal reduced peak blood glucose concentrations in subjects with type 2 diabetes compared with a cellulose control (Reppas et al., Diabetes Res. Clin. Pract., 1993, 22:61-9). It has been further demonstrated that HPMC reduced weight gain and insulin resistance in diet-induced obese mice and Syrian hamsters fed a high fat (HF) diet similar in fat content to the American diet. (Hung et al., J Diab 2009; 1(3):194-206); Kim et al., FASEB J., 2009, Meeting Abstracts, Abstract 212.2).

PCT Pat. Appl. Publ. Nos. WO 2008/051793 and WO 2008/051794 disclose the use of HPMC and other water-soluble and water-insoluble cellulose derivatives for preventing or treating metabolic syndrome and related conditions. See also U.S. Pat. Nos. 5,576,306; 5,585,366; 6,899,892; 5,721,221. PCT Pat. Appl. Publ. No. WO 2004/022074 discloses the use of a composition comprising a non-glucose carbohydrate and soluble fiber or a mixture of pectin and soluble fiber for controlling metabolic syndrome, diabetes mellitus and obesity, and for the promotion of weight loss or maintenance of the desired body weight.

SUMMARY OF THE INVENTION

As specified in the Background section above, there is a great need in the art to understand the impact that mammalian bacterial microbiota has on development of obesity and related disorders such as metabolic syndrome, diabetes mellitus, insulin-deficiency or insulin-resistance related disorders, glucose intolerance, non-alcoholic fatty liver, abnormal lipid metabolism, and atherosclerosis. There is further a great need in the art to employ such knowledge in development of new therapeutics to treat these and related disorders.

The present invention addresses these and other needs by characterizing specific diet-induced-obesity-associated changes in mammalian bacterial microbiota and by providing related diagnostic and therapeutic methods and probiotic and prebiotic compositions. The present invention further provides novel prebiotic compositions based on a surprising finding that cellulose ethers with a beta 1,4 linkage of anhydrous glucose units have a prebiotic effect although they are known to be substantially non-fermentable and non-digestible materials in the digestive tract of mammals.

In one aspect, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising
(a) measuring the populations of Firmicutes and/or Bacteroidetes in the ileal microbiota of the mammal;
(b) measuring the populations of Firmicutes and/or Bacteroidetes in the ileal microbiota of a healthy control;
(c) comparing the populations measured in steps (a) and (b), and
(d) determining that the mammal has a predisposition to the disease if the populations of Firmicutes and/or Bacteroidetes in the ileal microbiota of the mammal are increased as compared to the healthy control.

In a related aspect, the invention provides a method for promoting weight loss in a mammal comprising administering to the mammal a therapeutically effective amount of a probiotic composition, wherein said probiotic composition lowers the populations of Firmicutes and/or Bacteroidetes in the ileal microbiota of the mammal.

In another related embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a probiotic composition, wherein said probiotic composition lowers the populations of Firmicutes and/or Bacteroidetes in the ileal microbiota of the mammal.

In another embodiment, the invention provides a method for promoting weight loss in a mammal comprising administering to the mammal a therapeutically effective amount of a prebiotic composition, wherein said prebiotic composition lowers the populations of Firmicutes and/or Bacteroidetes in the ileal microbiota of the mammal.

In a further embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a prebiotic composition, wherein said prebiotic composition lowers the populations of Firmicutes and/or Bacteroidetes in the ileal microbiota of the mammal.

In a separate embodiment, the invention provides a method of lowering populations of Firmicutes and/or Bacteroidetes in the ileal microbiota of a mammal comprising administering to the mammal a prebiotic composition.

In another aspect, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising
(a) measuring the populations of Firmicutes in the cecal and/or fecal microbiota of the mammal;
(b) measuring the populations of Firmicutes in the cecal and/or fecal microbiota of a healthy control;
(c) comparing the populations measured in steps (a) and (b), and
(d) determining that the mammal has a predisposition to the disease if the populations of Firmicutes in the cecal and/or fecal microbiota of the mammal are increased as compared to the healthy control.

In a related aspect, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising
(a) measuring the ratio of the populations of Firmicutes to the populations of Eubacteria (F/E ratio=relative abundance of Firmicutes) in the cecal and/or fecal microbiota of the mammal;
(b) measuring the F/E ratio in the cecal and/or fecal microbiota of a healthy control;
(c) comparing the F/E ratios measured in steps (a) and (b), and
(d) determining that the mammal has a predisposition to the disease if the F/E ratio is increased in the cecal and/or fecal microbiota of the mammal as compared to the healthy control.

In a related aspect, the invention provides a method for promoting weight loss in a mammal comprising administering to the mammal a therapeutically effective amount of a probiotic composition, wherein said probiotic composition lowers the populations of Firmicutes in the cecal and/or fecal microbiota of the mammal.

In another related embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a probiotic composition, wherein said probiotic composition lowers the populations of Firmicutes in the cecal and/or fecal microbiota of the mammal.

In a further embodiment, the invention provides a method for promoting weight loss in a mammal comprising administering to the mammal a therapeutically effective amount of a prebiotic composition, wherein said prebiotic composition lowers the populations of Firmicutes in the cecal and/or fecal microbiota of the mammal.

In yet another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a prebiotic composition, wherein said prebiotic composition lowers the populations of Firmicutes in the cecal and/or fecal microbiota of the mammal.

In a separate embodiment, the invention provides a method of lowering the populations of Firmicutes in the cecal and/or fecal microbiota of a mammal comprising administering to the mammal a prebiotic composition.

In another embodiment, the invention provides a method for promoting weight loss in a mammal comprising administering to the mammal a therapeutically effective amount of a probiotic composition, wherein said probiotic composition lowers the ratio of the populations of Firmicutes to Eubacteria (F/E ratio=relative abundance of Firmicutes) in the cecal and/or fecal microbiota of the mammal.

In yet another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a probiotic composition, wherein said probiotic composition lowers the ratio of the populations of Firmicutes to Eubacteria (F/E ratio=relative abundance of Firmicutes) in the cecal and/or fecal microbiota of the mammal.

In a further embodiment, the invention provides a method for promoting weight loss in a mammal comprising administering to the mammal a therapeutically effective amount of a prebiotic composition, wherein said prebiotic composition lowers the ratio of the populations of Firmicutes to Eubacteria (F/E ratio=relative abundance of Firmicutes) in the cecal and/or fecal microbiota of the mammal.

In an additional embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a prebiotic composition, wherein said prebiotic composition lowers the ratio of the populations of Firmicutes to Eubacteria (F/E ratio=relative abundance of Firmicutes) in the cecal and/or fecal microbiota of the mammal.

In a separate embodiment, the invention provides a method of lowering the ratio of the populations of Firmicutes to Eubacteria (F/E ratio=relative abundance of Firmicutes) in the cecal and/or fecal microbiota of the mammal comprising administering to the mammal a prebiotic composition.

In another aspect, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising (a) measuring the populations of at least one genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae IS (PIS) in the intestinal microbiota of the mammal;

(b) measuring the populations of the same genus in the intestinal microbiota of a healthy control;

(c) comparing the populations measured in steps (a) and (b), and (d) determining that the mammal has a predisposition to the disease if the populations of at least one genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal are decreased as compared to the healthy control.

In a related aspect, the invention provides a method for promoting weight loss in a mammal comprising administering to the mammal a therapeutically effective amount of a probiotic composition, wherein said probiotic composition stimulates growth or metabolic activity of at least one strain from the genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal.

In a further embodiment, the invention provides a method for promoting weight loss in a mammal comprising administering to the mammal a therapeutically effective amount of a prebiotic composition, wherein said prebiotic composition stimulates growth or metabolic activity of at least one strain from the genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal.

The invention also provides a method for determining whether weight loss can be achieved in a mammal by the above two methods comprising (a) measuring the populations of at least one genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal;

(b) measuring the populations of the same genus in the intestinal microbiota of a healthy control;

(c) comparing the populations measured in steps (a) and (b), and (d) determining that weight loss can be achieved in the mammal by the above two methods if the populations of at least one genus selected from the group consisting of *Coprobacillus, Sporacetigenium Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal is decreased as compared to the healthy control.

In another related aspect, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a probiotic composition, wherein said probiotic composition stimulates growth or metabolic activity of at least one strain from the genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal.

In yet another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a prebiotic composition, wherein said prebiotic composition stimulates growth or metabolic activity of at least one strain from the genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal.

The invention also provides a method for determining whether a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis can be prevented or treated by the above two methods comprising (a) measuring the populations of at least one genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal;
(b) measuring the populations of the same genus in the intestinal microbiota of a healthy control;
(c) comparing the populations measured in steps (a) and (b), and
(d) determining that the disease in the mammal can be prevented or treated by the above two methods if the populations of at least one genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal is decreased as compared to the healthy control.

In a separate embodiment, the invention provides a method of stimulating growth or metabolic activity of at least one strain from the genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of a mammal comprising administering to the mammal a prebiotic composition.

In another aspect, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising
(a) measuring the populations of at least one taxon selected from the group consisting of *Johnsonella, Oscillibacter*, Lachnospiraceae, Ruminococcaceae, and Clostridiales in the intestinal microbiota of the mammal;
(b) measuring the populations of the same taxon in the intestinal microbiota of a healthy control;
(c) comparing the populations measured in steps (a) and (b), and
(d) determining that the mammal has a predisposition to the disease if the populations of at least one taxon selected from the group consisting of *Johnsonella, Oscillibacter*, Lachnospiraceae, Ruminococcaceae, and Clostridiales in the intestinal microbiota of the mammal is increased as compared to the healthy control.

In a related aspect, the invention provides a method for promoting weight loss in a mammal comprising administering to the mammal a therapeutically effective amount of a composition or a compound, wherein said composition or compound inhibits growth or metabolic activity of at least one strain from the taxon selected from the group consisting of *Johnsonella, Oscillibacter*, Lachnospiraceae, Ruminococcaceae, and Clostridiales in the intestinal microbiota of the mammal.

In another aspect, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a composition or a compound, wherein said composition or compound inhibits growth or activity of at least one strain from the taxon selected from the group consisting of *Johnsonella, Oscillibacter*, Lachnospiraceae, Ruminococcaceae, and Clostridiales in the intestinal microbiota of the mammal.

In one specific embodiment, the compound used in the above two methods is a narrow spectrum antibiotic. In another specific embodiment, the composition used in the above two methods is a probiotic composition comprising at least one strain from the genus selected from the group consisting of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS).

In a related embodiment, the invention provides a method for determining whether weight loss can be achieved in a mammal by the above method comprising
(a) measuring the populations of at least one taxon selected from the group consisting of *Johnsonella, Oscillibacter*, Lachnospiraceae, Ruminococcaceae, and Clostridiales in the intestinal microbiota of the mammal;
(b) measuring the populations of the same taxon in the intestinal microbiota of a healthy control;
(c) comparing the populations measured in steps (a) and (b), and
(d) determining that weight loss can be achieved in the mammal by the above method if the populations of at least one taxon selected from the group consisting of *Johnsonella, Oscillibacter*, Lachnospiraceae, Ruminococcaceae, and Clostridiales in the intestinal microbiota of the mammal is increased as compared to the healthy control.

In another related embodiment, the invention provides a method for determining whether a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis can be prevented or treated by the above method comprising (a) measuring the populations of at least one taxon selected from the group consisting of *Johnsonella, Oscillibacter*, Lachnospiraceae, Ruminococcaceae, and Clostridiales in the intestinal microbiota of the mammal;

(b) measuring the populations of the same taxon in the intestinal microbiota of a healthy control;

(c) comparing the populations measured in steps (a) and (b), and (d) determining that the disease in the mammal can be prevented or treated by the above method if the populations of at least one taxon selected from the group consisting of *Johnsonella, Oscillibacter*, Lachnospiraceae, Ruminococcaceae, and Clostridiales in the intestinal microbiota of the mammal is increased as compared to the healthy control.

In a separate embodiment, the invention provides a method of inhibiting growth or metabolic activity of at least one strain from the taxon selected from the group consisting of *Johnsonella, Oscillibacter*, Lachnospiraceae, Ruminococcaceae, and Clostridiales in the intestinal microbiota of a mammal comprising administering to the mammal a prebiotic composition.

In another aspect, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising (a) measuring the populations of at least one genus selected from the group consisting of *Coprobacillus* (C), *Sporacetigenium* (S), and *Holdemania* (H), in the intestinal microbiota of the mammal;

(b) measuring the populations of at least one genus selected from *Johnsonella* (J) and *Oscillibacter* (O) in the intestinal microbiota of the mammal;

(c) determining a ratio of one of C+S+H, C+H, C+S, S+H, C, S, or H as measured in step (a) to one of J+O, J, or O as measured in step (b), and (d) determining that the mammal has a predisposition to the disease if the ratio in step (c) is below 1, or determining that the mammal has no predisposition to the disease if the ratio in step (c) is above 3.

In a related aspect, the invention provides a method for promoting weight loss in a mammal comprising administering to the mammal a therapeutically effective amount of a probiotic composition, wherein said probiotic composition increases the ratio of populations of one of (a) *Coprobacillus* (C), *Sporacetigenium* (S), *Holdemania* (H), C+H, C+S, S+H, or C+S+H to populations of one of (b) *Johnsonella* (J), *Oscillibacter* (O), or J+O to above 3 in the intestinal microbiota of the mammal.

In another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a probiotic composition, wherein said probiotic composition increases the ratio of populations of one of (a) *Coprobacillus* (C), *Sporacetigenium* (S), *Holdemania* (H), C+H, C+S, S+H, or C+S+H to populations of one of (b) *Johnsonella* (J), *Oscillibacter* (O), or J+O to above 3 in the intestinal microbiota of the mammal.

In a further embodiment, the invention provides a method for promoting weight loss in a mammal comprising administering to the mammal a therapeutically effective amount of a prebiotic composition, wherein said prebiotic composition increases the ratio of populations of one of (a) *Coprobacillus* (C), *Sporacetigenium* (S), *Holdemania* (H), C+H, C+S, S+H, or C+S+H to populations of one of (b) *Johnsonella* (J), *Oscillibacter* (O), or J+O to above 3 in the intestinal microbiota of the mammal.

In yet another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a prebiotic composition, wherein said prebiotic composition increases the ratio of populations of one of (a) *Coprobacillus* (C), *Sporacetigenium* (S), *Holdemania* (H), C+H, C+S, S+H, or C+S+H to populations of one of (b) *Johnsonella* (J), *Oscillibacter* (O), or J+O to above 3 in the intestinal microbiota of the mammal.

In a separate embodiment, the invention provides a method of increasing the ratio of populations of one of (a) *Coprobacillus* (C), *Sporacetigenium* (S), *Holdemania* (H), C+H, C+S, S+H, or C+S+H to populations of one of (b) *Johnsonella* (J), *Oscillibacter* (O), or J+O in the intestinal microbiota of a mammal comprising administering to the mammal a prebiotic composition.

In another aspect, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising (a) measuring the populations of at least one genus selected from the group consisting of Erysipelotrichaceae Incertae Sedis (EIS), Peptostreptococcaceae Incertae Sedis (PIS), and *Clostridium cocleatum* (Cc) in the intestinal microbiota of the mammal;

(b) measuring the populations of *Johnsonella* (J) in the intestinal microbiota of the mammal;

(c) determining a ratio of one of EIS, PIS, EIS+PIS, or Cc as measured in step (a) to J as measured in step (b), and (d) determining that the mammal has a predisposition to the disease if the ratio in step (c) is below 1, or determining that the mammal has no predisposition to the disease if the ratio in step (c) is above 1.

In a related aspect, the invention provides a method for promoting weight loss in a mammal comprising administering to the mammal a therapeutically effective amount of a probiotic composition, wherein said probiotic composition increases the ratio of populations of one of (a) Erysipelotrichaceae Incertae Sedis (EIS), Peptostreptococcaceae Incertae Sedis (PIS), *Clostridium cocleatum* (Cc), or EIS+PIS to populations of (b) *Johnsonella* (J) to above 1 in the intestinal microbiota of the mammal.

In another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a probiotic composition, wherein said probiotic composition increases the ratio of populations of one of (a) Erysipelotrichaceae Incertae Sedis (EIS), Peptostreptococcaceae Incertae Sedis (PIS), *Clostridium cocleatum* (Cc), or EIS+PIS to populations of (b) *Johnsonella* (J) to above 1 in the intestinal microbiota of the mammal.

In a further embodiment, the invention provides a method for promoting weight loss in a mammal comprising administering to the mammal a therapeutically effective amount of a prebiotic composition, wherein said prebiotic composition increases the ratio of populations of one of (a) Erysipelotrichaceae Incertae Sedis (EIS), Peptostreptococcaceae Incertae Sedis (PIS), *Clostridium cocleatum* (Cc), or EIS+PIS to populations of (b) *Johnsonella* (J) to above 1 in the intestinal microbiota of the mammal.

In yet another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a prebiotic composition, wherein said prebiotic composition increases the ratio of populations of one of (a) Erysipelotrichaceae Incertae Sedis (EIS), Peptostreptococcaceae Incertae Sedis (PIS), *Clostridium cocleatum* (Cc), or EIS+PIS to populations of (b) *Johnsonella* (J) to above 1 in the intestinal microbiota of the mammal.

In a separate embodiment, the invention provides a method of increasing the ratio of populations of one of (a) Erysipelotrichaceae Incertae Sedis (EIS), Peptostreptococcaceae Incertae Sedis (PIS), *Clostridium cocleatum* (Cc), or EIS+PIS to populations of (b) *Johnsonella* (J) in the intestinal microbiota of a mammal comprising administering to the mammal a prebiotic composition.

In an additional embodiment, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising
(a) measuring the populations of at least one genus selected from the group consisting of *Coprobacillus* (C), *Sporacetigenium* (S), *Holdemania* (H), Erysipelotrichaceae Incertae Sedis (EIS), Peptostreptococcaceae Incertae Sedis (PIS), and *Clostridium cocleatum* (Cc) in the intestinal microbiota of the mammal;
(b) measuring the populations of Firmicutes (F) in the intestinal microbiota of the mammal;
(c) determining a ratio of one of C+S+H, C+H, C+S, S+H, C, S, H, EIS, PIS, or Cc as measured in step (a) to F as measured in step (b), and
(d) determining that the mammal has a predisposition to the disease if the ratio in step (c) is below 0.1, or determining that the mammal has no predisposition to the disease if the ratio in step (c) is above 0.1.

In a related embodiment, the invention provides a method for promoting weight loss in a mammal comprising administering to the mammal a therapeutically effective amount of a probiotic composition, wherein said probiotic composition increases the ratio of populations of one of (a) *Coprobacillus* (C), *Sporacetigenium* (S), *Holdemania* (H), Erysipelotrichaceae Incertae Sedis (EIS), Peptostreptococcaceae Incertae Sedis (PIS), *Clostridium cocleatum* (Cc), C+H, C+S, S+H, or C+S+H to populations of (b) Firmicutes (F) to above 0.1 in the intestinal microbiota of the mammal.

In another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a probiotic composition, wherein said probiotic composition increases the ratio of populations of one of (a) *Coprobacillus* (C), *Sporacetigenium* (S), *Holdemania* (H), Erysipelotrichaceae Incertae Sedis (EIS), Peptostreptococcaceae Incertae Sedis (PIS), *Clostridium cocleatum* (Cc), C+H, C+S, S+H, or C+S+H to populations of (b) Firmicutes (F) to above 0.1 in the intestinal microbiota of the mammal.

In yet another embodiment, the invention provides a method for promoting weight loss in a mammal comprising administering to the mammal a therapeutically effective amount of a prebiotic composition, wherein said prebiotic composition increases the ratio of populations of one of (a) *Coprobacillus* (C), *Sporacetigenium* (S), *Holdemania* (H), Erysipelotrichaceae Incertae Sedis (EIS), Peptostreptococcaceae Incertae Sedis (PIS), *Clostridium cocleatum* (Cc), C+H, C+S, S+H, or C+S+H to populations of (b) Firmicutes (F) to above 0.1 in the intestinal microbiota of the mammal.

In a further embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a prebiotic composition, wherein said prebiotic composition increases the ratio of populations of one of (a) *Coprobacillus* (C), *Sporacetigenium* (S), *Holdemania* (H), Erysipelotrichaceae Incertae Sedis (EIS), Peptostreptococcaceae Incertae Sedis (PIS), *Clostridium cocleatum* (Cc), C+H, C+S, S+H, or C+S+H to populations of (b) Firmicutes (F) to above 0.1 in the intestinal microbiota of the mammal.

In a separate embodiment, the invention provides a method of increasing the ratio of populations of one of (a) *Coprobacillus* (C), *Sporacetigenium* (S), *Holdemania* (H), Erysipelotrichaceae Incertae Sedis (EIS), Peptostreptococcaceae Incertae Sedis (PIS), *Clostridium cocleatum* (Cc), C+H, C+S, S+H, or C+S+H to populations of (b) Firmicutes (F) in the intestinal microbiota of a mammal comprising administering to the mammal a prebiotic composition.

In another aspect, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising
(a) measuring the populations of at least one family selected from Erysipelotrichaceae and Peptostreptococcacea, in the intestinal microbiota of the mammal;
(b) measuring the populations of at least one family selected from Lachnospiraceae and Ruminococcaceae in the intestinal microbiota of the mammal;
(c) determining a ratio of one of Erysipelotrichaceae+Peptostreptococcacea, Erysipelotrichaceae, or Peptostreptococcacea as measured in step (a) to one of Lachnospiraceae+ Ruminococcaceae, Lachnospiraceae, or Ruminococcaceae as measured in step (b), and (d) determining that the mammal has a predisposition to the disease if the ratio in step (c) is below 0.1, or determining that the mammal has no predisposition to the disease if the ratio in step (c) is above 0.1.

In a related embodiment, the invention provides a method for promoting weight loss in a mammal comprising administering to the mammal a therapeutically effective amount of a probiotic composition, wherein said probiotic composition increases the ratio of populations of one of (a) Erysipelotrichaceae+Peptostreptococcacea, Erysipelotrichaceae, or Peptostreptococcacea to populations of one of (b) Lachnospiraceae+Ruminococcaceae, Lachnospiraceae, or Ruminococcaceae to above 0.1 in the intestinal microbiota of the mammal.

In another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a probiotic composition, wherein said probiotic composition increases the ratio of populations of one of (a) Erysipelotrichaceae+Peptostreptococcacea, Erysipelotrichaceae, or Peptostreptococcacea to populations of one of (b) Lachnospiraceae+Ruminococcaceae, Lachnospiraceae, or Ruminococcaceae to above 0.1 in the intestinal microbiota of the mammal.

In a further embodiment, the invention provides a method for promoting weight loss in a mammal comprising administering to the mammal a therapeutically effective amount of a prebiotic composition, wherein said prebiotic composition increases the ratio of populations of one of (a) Erysipelotrichaceae+Peptostreptococcacea, Erysipelotrichaceae, or Peptostreptococcacea to populations of one of (b) Lachnospiraceae+Ruminococcaceae, Lachnospiraceae, or Ruminococcaceae to above 0.1 in the intestinal microbiota of the mammal.

In yet another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a prebiotic composition, wherein said prebiotic composition increases the ratio of populations of one of (a) Erysipelotrichaceae+Peptostreptococcacea, Erysipelotrichaceae, or Peptostreptococcacea to populations of one of (b) Lachnospiraceae+Ruminococcaceae, Lachnospiraceae, or Ruminococcaceae to above 0.1 in the intestinal microbiota of the mammal.

In a separate embodiment, the invention provides a method of increasing the ratio of populations of one of (a) Erysipelotrichaceae+Peptostreptococcacea, Erysipelotrichaceae, or Peptostreptococcacea to populations of one of (b) Lachnospiraceae+Ruminococcaceae, Lachnospiraceae, or Ruminococcaceae in the intestinal microbiota of a mammal comprising administering to the mammal a prebiotic composition.

In any of the above methods, the populations of bacteria can be determined by any method known in the art. In a preferred embodiment, the populations of bacteria are determined by qPCR of bacterial 16S rRNA.

In another aspect, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising (a) measuring the total number of Butyryl CoA transferase (BCoAT)-encoding genes in the intestinal microbiota of the mammal;

(b) measuring the total number of BCoAT-encoding genes in the intestinal microbiota of a healthy control;

(c) comparing the total number of BCoAT-encoding genes measured in steps (a) and (b), and (d) determining that the mammal has a predisposition to the disease if the total number of BCoAT-encoding genes in the intestinal microbiota of the mammal is increased as compared to the healthy control.

In another aspect, the invention provides a method for diagnosing predisposition to a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising (a) measuring a ratio of the total number of Butyryl CoA transferase (BCoAT)-encoding genes to copies of Bacteroidetes 16S rRNA in the intestinal microbiota of the mammal;

(b) measuring a ratio of the total number of BCoAT-encoding genes to copies of Bacteroidetes 16S rRNA in the intestinal microbiota of a healthy control;

(c) comparing the ratios of the total number of BCoAT-encoding genes to copies of Bacteroidetes 16S rRNA measured in steps (a) and (b), and (d) determining that the mammal has a predisposition to the disease if the ratio of the total number of BCoAT-encoding genes to copies of Bacteroidetes 16S rRNA in the intestinal microbiota of the mammal is increased as compared to the healthy control.

In the above methods, the total number of BCoAT-encoding genes and copies of Bacteroidetes 16S rRNA can be measured by any method known in the art. In a preferred embodiment, the total number of BCoAT-encoding genes and copies of Bacteroidetes 16S rRNA are measured by qPCR.

In a related aspect, the invention provides a method for promoting weight loss in a mammal comprising administering to the mammal a therapeutically effective amount of a probiotic composition, wherein said probiotic composition lowers the levels of Butyryl CoA transferase (BCoAT) enzyme and/or the levels of butyrate in the intestinal microbiota of the mammal.

In another embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a probiotic composition, wherein said probiotic composition lowers the levels of Butyryl CoA transferase (BCoAT) enzyme and/or the levels of butyrate in the intestinal microbiota of the mammal.

In yet another embodiment, the invention provides a method for promoting weight loss in a mammal comprising administering to the mammal a therapeutically effective amount of a prebiotic composition, wherein said prebiotic composition lowers the levels of Butyryl CoA transferase (BCoAT) enzyme and/or the levels of butyrate in the intestinal microbiota of the mammal.

In a further embodiment, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a prebiotic composition, wherein said prebiotic composition lowers the levels of Butyryl CoA transferase (BCoAT) enzyme and/or the levels of butyrate in the intestinal microbiota of the mammal.

In a separate embodiment, the invention provides a method of lowering the levels of Butyryl CoA Transferase (BcoAT) enzyme and/or the levels of butyrate in the intestinal microbiota of a mammal comprising administering to the mammal a prebiotic composition.

In any of the above methods, the levels of BCoAT enzyme can be measured by any method known in the art. In a preferred embodiment, the levels of BCoAT enzyme are measured by determining the total number of BCoAT-encoding genes. In another preferred embodiment, the levels of BCoAT enzyme are measured by BCoAT enzyme functional assay.

In any of the above methods, the levels of butyrate can be measured by any method known in the art. In a preferred embodiment, the levels of butyrate are measured using chromatographic methods.

In another aspect, the invention provides a method for promoting weight loss in a mammal comprising administering to the mammal a therapeutically effective amount of a probiotic composition, wherein said probiotic composition lowers the ratio of the total number of Butyryl CoA transferase (BCoAT)-encoding genes to copies of Bacteroidetes 16S rRNA in the intestinal microbiota of the mammal.

In yet another aspect, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a probiotic composition, wherein said probiotic composition lowers the ratio of the total number of Butyryl CoA transferase (BCoAT)-encoding genes to copies of Bacteroidetes 16S rRNA in the intestinal microbiota of the mammal.

In a further aspect, the invention provides a method for promoting weight loss in a mammal comprising administering to the mammal a therapeutically effective amount of a prebiotic composition, wherein said prebiotic composition lowers the ratio of the total number of Butyryl CoA transferase (BCoAT)-encoding genes to copies of Bacteroidetes 16S rRNA in the intestinal microbiota of the mammal.

In an additional aspect, the invention provides a method for preventing or treating a disease in a mammal selected from the group consisting of obesity, metabolic syndrome, diabetes mellitus, insulin-deficiency related disorders, insulin-resistance related disorders, glucose intolerance, non-alcoholic fatty liver, abnormal lipid metabolism, and atherosclerosis, said method comprising administering to the mammal a therapeutically effective amount of a prebiotic composition, wherein said prebiotic composition lowers the ratio of the total number of Butyryl CoA transferase (BCoAT)-encoding genes to copies of Bacteroidetes 16S rRNA in the intestinal microbiota of the mammal.

In a separate embodiment, the invention provides a method of lowering the ratio of the total number of Butyryl CoA Transferase (BcoAT)-encoding genes to copies of bacteroidetes 16S rRNA in the intestinal microbiota of a mammal comprising administering to the mammal a prebiotic composition.

In the above methods, the total number of BCoAT-encoding genes and copies of Bacteroidetes 16S rRNA can be measured by any method known in the art. In a preferred embodiment, the total number of BCoAT-encoding genes and copies of Bacteroidetes 16S rRNA are measured by qPCR.

In conjunction with therapeutic methods, the present invention also provides various probiotic and prebiotic compositions which can be used in such methods. Probiotic compositions according to the present invention can contain live bacterial strains and/or spores and also include conditionally lethal bacterial strains. Non-limiting examples of useful bacterial strains include, e.g., strains from the genera *Coprobacillus*, *Sporacetigenium*, *Holdemania*, *Dorea*, *Blautia*, *Enterococcus*, Erysipelotrichaceae Incertae Sedis (EIS), *Clostridium cocleatum*, and Peptosteptococcaceae Incertae Sedis (PIS).

Probiotic compositions of the present invention can further comprise a buffering agent such as, e.g., sodium bicarbonate, juice, milk, yogurt, infant formula, etc.

Probiotic compositions of the present invention can be administered conjointly with a prebiotic composition which stimulates growth and/or metabolic activity of bacteria contained in the probiotic composition. Such combinations of probiotic and prebiotic compositions can be administered in one composition or as two separate compositions (administered simultaneously or sequentially).

In a specific embodiment, a probiotic composition further comprises a compound selected from the group consisting of xylose, arabinose, ribose, galactose, rhamnose, cellobiose, fructose, lactose, salicin, sucrose, glucose, esculin, tween 80, trehalose, maltose, mannose, mellibiose, raffinose, fructooligosaccharides, galactooligosaccharides, amino acids, alcohols, and any combinations thereof. In another specific embodiment, a probiotic composition further comprises a compound selected from the group consisting of trehalose, cellobiose, maltose, mannose, sucrose, fructose, galactose, lactose, salicin, melibiose, raffinose, and any combinations thereof. In yet another specific embodiment, a probiotic composition further comprises a compound selected from the group consisting of water-soluble cellulose derivatives, water-insoluble cellulose derivatives, unprocessed oatmeal, metamucil, all-bran, and any combinations thereof. In a preferred embodiment, the water-soluble cellulose derivative is selected from the group consisting of methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose. In another preferred embodiment, the water-insoluble cellulose derivative is ethyl cellulose.

In one specific embodiment, the invention provides a probiotic composition comprising one or more strain from the genus *Holdemania* and one or more compounds selected from the group consisting of Tween 80, esculin, fructose, glucose, lactose, maltose, salicin, and sucrose.

In another specific embodiment, the invention provides a probiotic composition comprising one or more strain from the genus *Sporoacetigenicum* and one or more compounds selected from the group consisting of arabinose, fructose, glucose, maltose, and xylose.

In yet another specific embodiment, the invention provides a probiotic composition comprising one or more strain from the genus *Coprobacillus* and one or more compounds selected from the group consisting of mannose, fructose, sucrose, maltose, cellobiose, trehalose, salicin, lactose, glucose, and galactose.

In yet another specific embodiment, the invention provides a probiotic composition comprising one or more strain from the genus *Clostridium cocleatum* and one or more compounds selected from the group consisting of cellobiose, fructose, galactose, glucose, inulin, lactose, maltose, mannose, mellibiose, raffinose, and sucrose.

In one embodiment, the invention provides a prebiotic composition useful in the methods of the present invention which prebiotic composition comprises a compound selected from the group consisting of trehalose, cellobiose, maltose, mannose, sucrose, fructose, galactose, lactose, salicin, melibiose, raffinose, and any combinations thereof. In another embodiment, the invention provides a prebiotic composition comprising a compound selected from the group consisting of xylose, arabinose, ribose, galactose, rhamnose, cellobiose, fructose, lactose, salicin, sucrose, glucose, esculin, tween 80, trehalose, maltose, mannose, mellibiose, raffinose, fructooligosaccharides, galactooligosaccharides, amino acids, alcohols, water-soluble cellulose derivatives, water-insoluble cellulose derivatives, unprocessed oatmeal, metamucil, all-bran, and any combinations thereof. In one preferred embodiment, the water-soluble cellulose derivative is selected from the group consisting of methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose. In another preferred embodiment, the water-insoluble cellulose derivative is ethyl cellulose.

Probiotic and prebiotic compositions useful in the methods of the present invention can be formulated in different forms (e.g., as a liquid solution, powder, capsule, tablet, suppository, etc.) and can be administered by various methods (e.g., orally, rectally, via esophagogastroduodenoscopy, colonoscopy, nasogastric tube, orogastric tube, etc.).

In one embodiment, the mammal in any of the above methods is human.

In one embodiment, the mammal in any of the above methods is on a high fat diet.

BRIEF DESCRIPTION OF THE DRAWINGS

FIGS. 2*a*-2*t* are scatter plots showing changes in murine metabolic phenotypes in response to 4 weeks of dietary intervention. Panels represent fasting plasma: a) cholesterol, b) HDL, c) LDL, d) VLDL, e) free fatty acids, f) triglycerides, g) glucose, h) insulin, i) leptin, j) adiponectin, k) liver adiposity (% lipids), l) liver triglycerides, m) fecal saturatd fat, n) fecal unsaturated fat, o) fecal transunsaturated fats, p) fecal bile acid, q) fecal sterols, r) fecal monoacyglycerides, s) fecal diacylgycerridess, and t) fecal triacylglycerides. * $p<0.05$,  $p<0.01$, * $p<0.001$, FDR-corrected Mann-Whitney U test.

FIG. 19 shows clustering of intestinal microbiota by heat map analysis. Number of samples falling within either the top or bottom major branch for mice fed HFD, LFD, or HPMC, P-values for $\chi^2$ and Fisher's exact test for contingency.

DETAILED DESCRIPTION OF THE INVENTION

Figure 1:
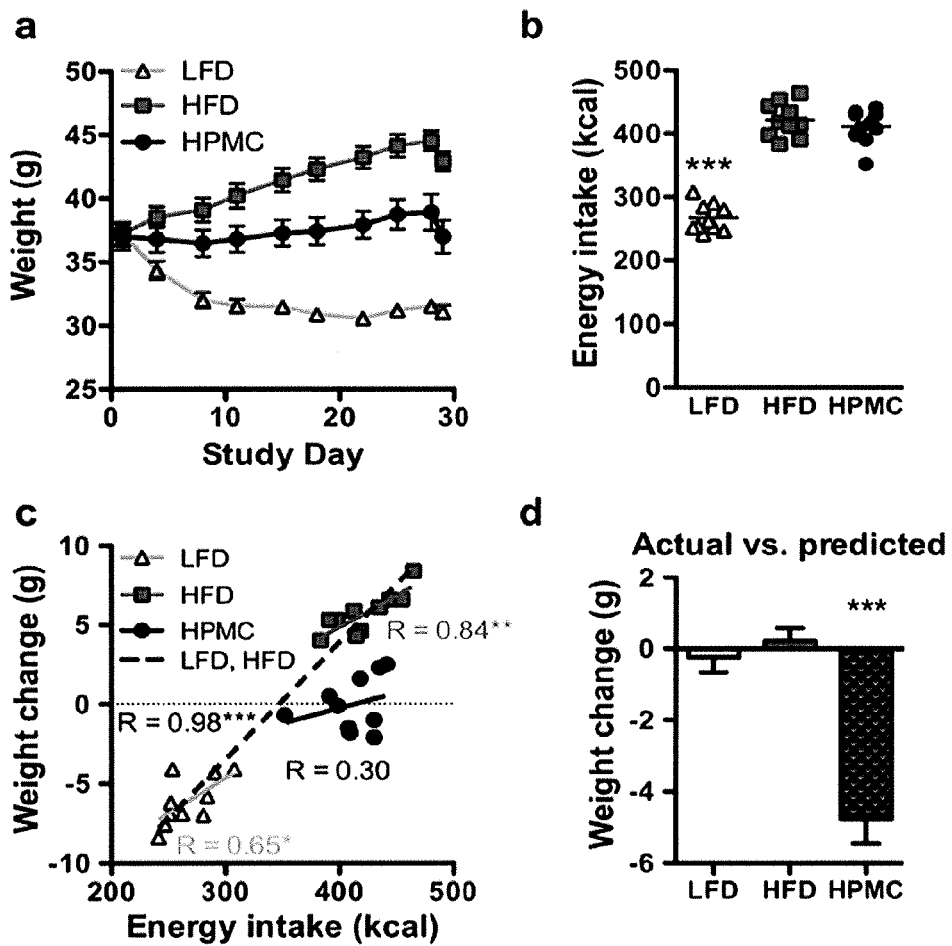
FIGS. 1*a*-1*d* are plots showing the effect of diet on host metabolism. Adult C57BL/6 mice were fed high fat diet (HFD, 60% kcal from fat) for two months prior to the study, then continued on HFD, or switched to either low fat diet (LFD, 10% kcal from fat) or to HFD with 10% HPMC supplementation (HPMC). Panels: (a) weight for the mice over the 4-week study; (b) total energy intake (kcal) for the duration of the 4-week experiment (bar at median); (c) correlation by linear regression between 4-week weight change and total energy intake; (d) Difference (mean±SE) between actual and predicted weight change, based on energy intake and the best fit line for LFD and HFD mice; (f) liver triglycerides; (g) fecal saturated fat; (h) fecal unsaturated fat; (i) fecal bile acids. * $p<0.05$,  $p<0.01$, * $p<0.001$, Mann-Whitney U test for b and d, non-zero slope for c.

The present invention is based on an unexpected experimental observation that prevention of weight gain associated with adding HPMC to a high-fat diet in mice is associated with changes in the population size and composition of an intestinal microbiota with (i) reductions in total bacterial populations, primarily reflecting reduction in phylum Firmicutes (the effect being significant in both the cecum and the ileum), (ii) significant decreases in the populations of genera *Johnsonella* and *Oscillibacter*, family Lachnospiraceae and Ruminococcaceae, order Clostridiales, class Clostridia, and phylum Firmicutes, (iii) marked increases in the populations of genera *Coprobacillus, Sporacetigenium, Holdemania*, Erysipelotrichaceae Incertae Sedis (EIS), *Clostridium cocleatum*, and Peptosteptococcaceae Incertae Sedis (PIS), moderate increases in genera *Dorea, Blautia*, and *Enterococcus*, increases in family Erysipelotrichaceae, Peptostreptococcaceae, Clostridiales Insertae Sedis XIV, and Enterococcaceae, order Erysipelotrichales, and Lactobacillales, and class Erysipelotrichi and Bacilli, especially in relation to the total numbers of Firmicutes, and (iv) significant decreases in BCoAT gene levels, in a manner predicted to lower butyrate availability and energy production. The present invention is further based on a surprising observation that cellulose ethers with a beta 1,4 linkage of anhydrous glucose units have a prebiotic effect although they are known to be substantially non-fermentable and non-digestible materials in the digestive tract of mammals.

The present invention provides novel probiotic and prebiotic compositions and methods for diagnosing predisposition to and methods for treating obesity, metabolic syndrome, insulin-deficiency or insulin-resistance related disorders, glucose intolerance, diabetes mellitus, non-alcoholic fatty liver, abnormal lipid metabolism, atherosclerosis, and related disorders based on the above-identified changes in mammalian bacterial intestinal microbiota.

DEFINITIONS AND ABBREVIATIONS

The term "Eubacteria" refers to all bacteria and excludes archaea. In mammals, >90% of all colonic bacteria are in the phyla Firmicutes or Bacteroidetes (Ley et al., Nat Rev Microbiol 2008; 6:776-88).

The term "intestinal microbiota" refer to bacteria in the digestive tract.

The term "cecal microbiota" refers to microbiota derived from cecum, which in mammals is the beginning region of the large intestine in the form of a pouch connecting the ileum with the ascending colon of the large intestine; it is separated from the ileum by the ileocecal valve (ICV), and joins the colon at the cecocolic junction.

The term "ileal microbiota" refers to microbiota derived from ileum, which in mammals is the final section of the small intestine and follows the duodenum and jejunum; ileum is separated from the cecum by the ileocecal valve (ICV).

As used herein, the term "probiotic" refers to a substantially pure bacteria (i.e., a single isolate), or a mixture of desired bacteria, and may also include any additional components that can be administered to a mammal for restoring microbiota. Such compositions are also referred to herein as a "bacterial inoculant." Probiotics or bacterial inoculant compositions of the invention are preferably administered with a buffering agent to allow the bacteria to survive in the acidic environment of the stomach, i.e., to resist low pH and to grow in the intestinal environment. Such buffering agents include sodium bicarbonate, juice, milk, yogurt, infant formula, and other dairy products.

As used herein, the term "prebiotic" refers to an agent that increases the number of one or more desired bacteria and/or desired metabolic activity. The term "metabolic activity of bacteria" broadly refers to any aspect of microbial catabolism and/or anabolism (including, e.g., the breakdown of carbohydrates, proteins, and lipids, secretion of small molecules such as, e.g., short chain fatty acids and proteins, synthesis or modifications of large molecular weight bioactive molecules that involve energy generation, building of cell walls, capsules, and internal structures) as well as to any pathway affecting the ability of bacteria to move and/or reproduce. The metabolic activity need not relate to the desired bacteria but can be general (e.g., BCoAT activity).

Non-limiting examples of prebiotics useful in the methods of the present invention include xylose, arabinose, ribose, galactose, rhamnose, cellobiose, fructose, lactose, salicin, sucrose, glucose, esculin, tween 80 (e.g., 0.2%), trehalose, maltose, mannose, mellibiose, raffinose, fructooligosaccharides (e.g., oligofructose, inulin, inulin-type fructans), galactooligosaccharides, amino acids, alcohols, water-soluble cellulose derivatives (most preferably, methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose), water-insoluble cellulose derivatives (most preferably, ethyl cellulose), unprocessed oatmeal, metamucil, all-bran, and any combinations thereof. See, e.g., Ramirez-Farias et al., Br J Nutr (2008) 4:1-10; Pool-Zobel and Sauer, J Nutr (2007), 137:2580 S-2584S.

The term "water-soluble cellulose derivative" as used herein means that the cellulose derivative has a solubility in water of at least 2 grams, preferably at least 3 grams, more preferably at least 5 grams in 100 grams of distilled water at 25° C. and 1 atmosphere. The term "water-soluble cellulose derivative" does not include unmodified cellulose itself which tends to be water-insoluble.

The term "water-insoluble cellulose derivative" as used herein does not include unmodified cellulose and means that the cellulose derivative has a solubility in water of less than 2 grams, preferably less than 1 gram, in 100 grams of distilled water at 25° C. and 1 atmosphere.

The terms "treat" or "treatment" of a state, disorder or condition include:
(1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or
(2) inhibiting the state, disorder or condition, i.e., arresting, reducing or delaying the development of the disease or a relapse thereof (in case of maintenance treatment) or at least one clinical or sub-clinical symptom thereof or
(3) relieving the disease, i.e., causing regression of the state, disorder or condition or at least one of its clinical or sub-clinical symptoms.

The benefit to a subject to be treated is either statistically significant or at least perceptible to the patient or to the physician.

A "therapeutically effective amount" means the amount of a bacterial inoculant or a compound (e.g., a prebiotic or a narrow spectrum antibiotic or anti-bacterial agent) that, when administered to a subject for treating a state, disorder or condition, is sufficient to effect such treatment. The "therapeutically effective amount" will vary depending on the compound, bacteria or analogue administered as well as the disease and its severity and the age, weight, physical condition and responsiveness of the subject to be treated.

The term "narrow spectrum antibiotic" is an antibiotic which can selectively inhibit growth and/or activity of one or few bacterial species or taxa.

The terms "diet-induced obesity (DIO) diet" and "high fat diet" are used herein interchangeably to refer to a high-fat diet, typically of 45% or 60% in total fat content, that leads to obesity, hyperglycemia, hyperinsulinemia, and hypertension in a mouse model. The composition of the diet was designed to approximate the typical Western diet. See, e.g., Surwit et al., Metabolism, 1995, 44:645-651.

The term "Butyryl CoA transferase (BCoAT)-encoding genes" as used herein refers to genes encoding an enzyme involved in the regulation of metabolism of short chain fatty acids and, preferably, butyrate synthesis.

As used herein, the term "metagenome" refers to genomic material obtained directly from a subject, instead of from culture. Metagenome is thus composed of microbial and host components.

As used herein, the phrase "pharmaceutically acceptable" refers to molecular entities and compositions that are generally regarded as physiologically tolerable.

As used herein, the term "combination" of a bacterial inoculant, probiotic, analogue, or prebiotic compound and at least a second pharmaceutically active ingredient means at least two, but any desired combination of compounds can be delivered simultaneously or sequentially (preferably, within a 24 hour period).

Within the meaning of the present invention, the term "conjoint administration" is used to refer to administration of a probiotic and a prebiotic simultaneously in one composition, or simultaneously in different compositions, or sequentially (preferably, within a 24 hour period).

"Patient" or "subject" as used herein refers to all mammals and includes human and veterinary animals. The term "healthy control" refers to a mammal of the same species (and preferably same sex and age group) which does not have a disease or condition that is being treated.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The abbreviations used in the nucleotide sequences throughout this application are as follows: A=adenine, G=guanine, C=cytosine, T=thymine, U=uracil, R=purine (G or A), Y=pyrimidine (T or U or C), M=amino (A or C), S=strong interactions 3H-bonds (G or C), V=(A or C or G), K=(G or T), W=weak interactions 2H-bonds (A or T or U), N=any (A or G or C or T or U), I=inosine.

Diagnostic Methods of the Invention

In one embodiment, the present invention provides a method for diagnosing predisposition to obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by comparing the populations of Firmicutes and/or Eubacteria and/or Bacteroidetes in the ileal microbiota of the mammal and in healthy controls, wherein the increased populations of Firmicutes and/or Eubacteria and/or Bacteroidetes in the ileal microbiota as compared to healthy controls are indicative of predisposition to obesity and associated conditions.

In another embodiment, the invention provides a method for diagnosing predisposition to obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by comparing the levels populations of Firmicutes in the cecal and/or fecal microbiota of the mammal and in healthy controls, wherein the increased level populations of Firmicutes in the cecal and/or fecal microbiota as compared to healthy controls are indicative of predisposition to obesity and associated conditions.

In yet another embodiment, the invention provides a method for diagnosing predisposition to obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by comparing the ratio of Firmicutes to Eubacteria (F/E ratio=relative abundance of Firmicutes) in the cecal and/or fecal microbiota of the mammal and in healthy controls, wherein the increased F/E ratio in the cecal and/or fecal microbiota as compared to healthy controls is indicative of predisposition to obesity and associated conditions.

In a further embodiment, the invention provides a method for diagnosing predisposition to obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by determining the level of at least one of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal, comparing the level to the level of the same bacteria in the intestinal microbiota of healthy controls, and identifying as a mammal predisposed to obesity etc. any mammal in which the level of at least one of said bacteria is lower than in healthy controls.

In a separate embodiment, the invention provides a method for diagnosing predisposition to obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by determining the level of at least one of *Johnsonella, Oscillibacter*, Lachnospiraceae, Ruminococcaceae, and Clostridiales in the intestinal microbiota of the mammal, comparing the level to the level of the same bacteria in the intestinal microbiota of healthy controls, and identifying as a mammal predisposed to obesity etc. any mammal in which the level of at least one of said bacteria is higher than in healthy controls.

In another embodiment, the invention provides a method for diagnosing predisposition to obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by comparing the total number of Butyryl CoA transferase (BCoAT)-encoding genes (or the ratio of the total number of BCoAT-encoding genes to copies of Bacteroidetes 16S rRNA) in the intestinal microbiota of the mammal and in healthy controls, wherein the increased levels of BCoAT genes (or the increased ratio of BCoAT-encoding genes to copies of Bacteroidetes 16S rRNA) as compared to healthy controls are indicative of predisposition to obesity and associated conditions.

Specific changes in microbiota can be detected using various methods, including without limitation quantitative PCR (qPCR) or high-throughput sequencing methods which detect over- and under-represented genes in the total bacterial population (e.g., 454-sequencing for community analysis), or transcriptomic or proteomic studies that identify lost or gained microbial transcripts or proteins within total bacterial populations. See, e.g., Eckburg et al., Science, 2005, 308: 1635-8; Costello et al., Science, 2009, 326:1694-7; Orrice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703. While any number of suitable molecular techniques may be utilized, particularly useful molecular techniques for the purposes of the present invention include (i) screening of microbial 16S ribosomal RNAs (16S rRNA) using PCR and (ii) high-throughput "metagenome" sequencing methods, which detect over- and under-represented genes in the total bacterial population. Screening of 16S rRNA genes permits characterizing microorganisms present in the microbiota at the species, genus, family, order, class, or phylum level. Such screening can be performed, e.g., by conducting PCR using universal primers to the V2, V3, V4, V6 (or V2-V4) region of the 16S rRNA gene followed by high-throughput sequencing and taxonomic analysis. See e.g., Gao et al. Proc. Natl. Acad. Sci. USA, 2007; 104:2927-32; Zoetendal et al., Mol. Microbiol., 2006, 59:1639-1650; Schloss and Handelsman, Microbiol. Mol. Biol. Rev., 2004, 68:686-691; Smit et al., Appl. Environ. Microbiol., 2001, 67:2284-2291; Harris and Hartley, J. Med. Microbiol., 2003, 52:685-691; Saglani et al., Arch Dis Child, 2005, 90:70-73. The high-throughput "metagenome" sequencing methods involve obtaining multiple parallel short sequencing reads looking for under- and over-represented genes in a total mixed sample population. Such sequencing is usually followed by determining the G+C content or tetra-nucleotide content (Pride et al., Genome Res., 2003, 13; 145) of the genes to characterize the specific bacterial species in the sample. Additional techniques include those involving cultivation of individual microorganisms from mixed samples. See, e.g., Manual of Clinical Microbiology, 8th edition; American Society of Microbiology, Washington D.C., 2003.

Therapeutic Methods of the Invention

In conjunction with the diagnostic methods, the present invention also provides therapeutic methods for treating obesity, metabolic syndrome, insulin-deficiency or insulin-resistance related disorders, glucose intolerance, diabetes mellitus, non-alcoholic fatty liver, abnormal lipid metabolism, atherosclerosis, and related disorders by restoring mammalian bacterial intestinal microbiota to the composition observed in healthy subjects.

In certain specific embodiments, restoring of microbiota is achieved by administering to a mammal in need thereof a therapeutically effective amount of a probiotic composition comprising an effective amount of at least one bacterial strain, or a combinations of several strains, or a prebiotic composition, or a mixture thereof, wherein the composition (i) stimulates or inhibits specific metabolic pathways involved in host energy homeostasis and/or (ii) stimulates growth and/or activity of bacteria which are under-represented in a disease and/or (iii) inhibits growth and/or activity of bacteria which are over-represented in a disease.

In one embodiment, the present invention provides a method for promoting weight loss, preventing or treating obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by administering a probiotic or a prebiotic composition or a combination thereof, that stimulates growth or activity of at least one of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal. In a related embodiment, the invention provides a method for determining whether weight loss can be achieved or obesity and associated conditions can be treated in a mammal by the latter method by determining the level of at least one of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS) in the intestinal microbiota of the mammal and comparing said level to the level of the same bacteria in the intestinal microbiota of healthy controls, and identifying as a mammal treatable by the latter method any mammal in which the level of at least one of said bacteria is lower than in healthy controls.

In another embodiment, the invention provides a method for promoting weight loss, preventing or treating obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by inhibiting growth or activity of at least one of *Johnsonella, Oscillibacter*, Lachnospiraceae, Ruminococcaceae, and Clostridiales in the intestinal microbiota of the mammal (e.g., by administering a narrow spectrum antibiotic, or another anti-bacterial agent, including a probiotic [e.g., at least one of *Coprobacillus, Sporacetigenium, Holdemania, Dorea, Blautia, Enterococcus*, Erysipelotrichaceae Incertae Sedis (EIS), *Clostridium cocleatum*, and Peptosteptococcaceae Incertae Sedis (PIS)] which competes with at least one of *Johnsonella, Oscillibacter*, Lachnospiraceae, Ruminococcaceae, and Clostridiales for metabolic substrates, physical niches, or produces relevant antibiotic(s)). In a related embodiment, the invention provides a method for determining whether weight loss can be achieved or obesity and associated conditions can be treated in a mammal by the latter method by determining the level of at least one of *Johnsonella, Oscillibacter*, Lachnospiraceae, Ruminococcaceae, and Clostridiales in the intestinal microbiota of the mammal and comparing said level to the level of the same bacteria in the intestinal microbiota of a healthy control, and identifying as a mammal treatable by the latter method any mammal in which the level of at least one of said bacteria is higher than in healthy controls.

In yet another embodiment, the invention provides a method for promoting weight loss, preventing or treating obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by administering a probiotic or a prebiotic composition or a combination thereof, that lowers the populations of Firmicutes and/or Eubacteria and/or Bacteroidetes in the ileal microbiota of the mammal.

In a further embodiment, the invention provides a method for promoting weight loss, preventing or treating obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by administering a probiotic or a prebiotic composition or a combination thereof, that lowers the populations of Firmicutes in the cecal and/or fecal microbiota of the mammal.

In a separate embodiment, the invention provides a method for promoting weight loss, preventing or treating obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by administering a probiotic or a prebiotic composition or a combination thereof, that lowers the ratio of Firmicutes to Eubacteria (F/E ratio=relative abundance of Firmicutes) in the cecal and/or fecal microbiota of the mammal.

In another embodiment, the invention provides a method for promoting weight loss, preventing or treating obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis) in a mammal by administering a probiotic or a prebiotic composition or a combination thereof, that lowers the levels of Butyryl CoA transferase (BCoAT) enzyme in the intestinal microbiota of the mammal. In a related embodiment, the invention provides a method for promoting weight loss, preventing or treating obesity and associated conditions in a mammal by administering a probiotic or a prebiotic composition or a combination thereof, that lowers the ratio of the total number of Butyryl CoA transferase (BCoAT)-encoding genes to copies of Bacteroidetes 16S rRNA in the intestinal microbiota of the mammal. In another related embodiment, the invention provides a method for promoting weight loss, preventing or treating obesity and associated conditions in a mammal by administering a probiotic or a prebiotic composition or a combination thereof, that lowers the levels of butyrate (e.g., measured using chromatographic methods [see, e.g., Renom et al., Clin. Chem. Lab. Med., 2001, 39(1): 15-19]) in the intestinal microbiota of the mammal.

Probiotic and Prebiotic Compositions, Dosages and Administration

In conjunction with the above-identified therapeutic methods, the present invention provides probiotic and prebiotic compositions or combinations of prebiotics and probiotics useful for promoting weight loss and/or treating obesity and associated conditions (e.g., metabolic syndrome, diabetes mellitus, insulin-deficiency or insulin-resistance related disorders, glucose intolerance, non-alcoholic fatty liver, abnormal lipid metabolism, and atherosclerosis).

Probiotics useful in the methods of the present invention can comprise live bacterial strains and/or spores. In a preferred embodiment, such live bacterial strains and/or spores are from the genus *Coprobacillus, Sporacetigenium, Holdemania*, Erysipelotrichaceae Incertae Sedis (EIS), *Clostridium cocleatum*, or Peptosteptococcaceae Incertae Sedis (PIS). In certain embodiments, the bacteria administered in the therapeutic methods of the invention comprise one or more of *Coprobacillus, Sporacetigenium, Holdemania*, Erysipelotrichaceae Incertae Sedis (EIS), *Clostridium cocleatum*, and Peptosteptococcaceae Incertae Sedis (PIS) and one or more additional bacterial strains (such as, e.g., *Oxalobacter* species, *Lactobacillus* species, etc.).

One or several different bacterial inoculants can be administered simultaneously or sequentially (including administering at different times). Such bacteria can be isolated from microbiota and grown in culture using known techniques. However, many bacterial species are very difficult to culture and administration of others may lead to various undesirable side-effects. The present invention therefore also comprises administering "bacterial analogues", such as recombinant carrier strains expressing one or more heterologous genes derived from the bacteria affected in a disease. The use of such recombinant bacteria may allow the use of lower therapeutic amounts due to higher protein expression and may simultaneously minimize any potential harmful side-effects associated with reintroduction of specific bacterial strains. Non-limiting examples of recombinant carrier strains useful in the methods of the present invention include *E. coli* and *Lactobacillus, Bacteroides* and *Oxalobacter*. Methods describing the use of bacteria for heterologous protein delivery are described, e.g., in U.S. Pat. No. 6,803,231.

In certain embodiments, a conditional lethal bacterial strain can be utilized as the inoculant or to deliver a recombinant construct. Such a conditional lethal bacteria survives for a limited time typically when provided certain nutritional supplements. It is contemplated that such a supplement could be a liquid, formulated to contain the nutritional component necessary to keep the bacteria alive. It is further contemplated that a patient/subject would drink such a supplement in intervals to keep the bacteria alive. Once the supplement is depleted, the conditional lethal bacteria dies. Methods relating to conditional lethal strains of *H. pylori* are described in U.S. Pat. No. 6,570,004.

In certain embodiments, the bacterial inoculant used in the methods of the invention further comprises a buffering agent. Examples of useful buffering agents include sodium bicarbonate, juice, milk, yogurt, infant formula, and other dairy products.

Administration of a bacterial inoculant can be accomplished by any method likely to introduce the organisms into the desired location. In a preferred embodiment, bacteria are administered orally. Alternatively, bacteria can be administered rectally, by enema, by esophagogastroduodenoscopy, colonoscopy, nasogastric tube, or orogastric tube.

The bacteria can be mixed with an excipient, diluent or carrier selected with regard to the intended route of administration and standard pharmaceutical practice. For easier delivery to the digestive tract, bacteria can be applied to liquid or solid food, or feed or to drinking water. For oral administration, bacteria can be also formulated in a capsule. The excipient, diluent and/or carrier must be "acceptable" in the sense of being compatible with the other ingredients of the formulation and should be non-toxic to the bacteria and the subject/patient. Preferably, the excipient, diluent and/or carrier contains an ingredient that promotes viability of the bacteria during storage. The formulation can include added ingredients to improve palatability, improve shelf-life, impart nutritional benefits, and the like. Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

The dosage of the bacterial inoculant or compound of the invention will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve colonization of the intestinal tract with the desired bacterial inoculant, e.g. $10^6$, $10^7$, $10^8$, $10^9$, and $10^{10}$ CFU for example, can be administered in a single dose. Lower doses can also be effective, e.g., $10^4$, and $10^5$ CFU.

Non-limiting examples of prebiotics useful in the methods of the present invention include xylose, arabinose, ribose, galactose, rhamnose, cellobiose, fructose, lactose, salicin, sucrose, glucose, esculin, tween 80, trehalose, maltose, mannose, mellibiose, raffinose, fructooligosaccharides (e.g., oligofructose, inulin, inulin-type fructans), galactooligosaccharides, amino acids, alcohols, water-soluble cellulose derivatives (most preferably, methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methyl- cellulose, and carboxymethyl cellulose), water-insoluble cellulose derivatives (most preferably, ethyl cellulose), unprocessed oatmeal, metamucil, all-bran, and any combinations thereof.

Table 1 provides a chart of prebiotics useful for stimulating growth and metabolic activity (by acting as substrate for fermentation) of *Coprobacillus, Sporacetigenium, Holdemania*, or *Clostridium cocleatum* based on information from Kageyama et al., Microbiol. Immunol., 2000, 44:23-28; Chen et al., Int J Syst Evol Microbiol, 2006, 56:721-725; Moore et al., Int J Syst Bact, 1997, 47(4):1201-1204, Willems et al., Int J Syst Bact, 1995, 45:855-857; Lino et al., Int J Syst Evol Microbiol, 2007, 57:1840-1845; Kaneuchi et al., Int J Syst Bact, 1979, 29, 1. As follows from Table 1, trehalose, cellobiose, lactose, maltose, mannose, sucrose, fructose, galactose, salicin, mellibiose, and raffinose stimulate growth and metabolic activity of two or more genera selected from *Coprobacillus, Sporacetigenium, Holdemania*, or *Clostridium cocleatum*, but not of *Johnsonella and Oscillibacter*.

TABLE 1

| | Coprobacillus | Holdemania | Sporacetegenium | Clostridium cocleatum | Johnsonella | Oscillibacter |
|---|---|---|---|---|---|---|
| Arabinose | − | w | + | − | − | +/−[a] |
| Cellobiose | + | w | w | + | − | − |
| Esculin | − | + | | | − | |
| Fructose | + | + | + | + | − | − |
| Galactose | + | | w | + | − | − |
| Glucose | + | + | + | + | + | + |
| Inulin | | | | + | | |
| Lactose | + | + | w | + | − | − |
| Maltose | + | + | + | + | − | − |
| Mannose | + | w | w | + | − | − |
| Mellibiose | | w | w | + | − | − |
| Raffinose | − | w | w | + | − | − |
| Rhamnose | − | w | w | − | − | − |
| Ribose | − | w | +/− | − | − | + |
| Salicin | + | + | − | w | − | − |
| Sucrose | + | + | w | + | − | − |
| Trehalose | + | w | w | − | − | − |
| Xylose | − | w | + | − | − | + |

+ facilitates growth, w weak growth promotion,
+/− growth variable dependent on strain,
− no growth effect.
Bold facilitates growth in ≥2 CSH organisms.
[a] + for L-arabinose; − for D-arabinose.

Preferred water-soluble cellulose derivatives for use in the present invention are water-soluble cellulose esters and cellulose ethers. Preferred cellulose ethers are water-soluble carboxy-$C_1$-$C_3$-alkyl celluloses, such as carboxymethyl celluloses; water-soluble carboxy-$C_1$-$C_3$-alkyl hydroxy-$C_1$-$C_3$-alkyl celluloses, such as carboxymethyl hydroxyethyl celluloses; water-soluble $C_1$-$C_3$-alkyl celluloses, such as methylcelluloses; water-soluble $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; water-soluble hydroxy-$C_{1-3}$-alkyl celluloses, such as hydroxyethyl celluloses or hydroxypropyl celluloses; water-soluble mixed hydroxy-$C_1$-$C_3$-alkyl celluloses, such as hydroxyethyl hydroxypropyl celluloses, water-soluble mixed $C_1$-$C_3$-alkyl celluloses, such as methyl ethyl celluloses, or water-soluble alkoxy hydroxyethyl hydroxypropyl celluloses, the alkoxy group being straight-chain or branched and containing 2 to 8 carbon atoms. The more preferred cellulose ethers are methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose, which are classified as water-soluble cellulose ethers by the skilled artisans. The most preferred water-soluble cellulose ethers are methylcelluloses with a methyl molar substitution $DS_{methoxyl}$ of from 0.5 to 3.0, preferably from 1 to 2.5, and hydroxypropyl methylcelluloses with a $DS_{methoxyl}$ of from 0.9 to 2.2, preferably from 1.1 to 2.0, and a $MS_{hydroxypropoxyl}$ of from 0.02 to 2.0, preferably from 0.1 to 1.2. The methoxyl content of methyl cellulose can be determined according to ASTM method D 1347-72 (reapproved 1995). The methoxyl and hydroxypropoxyl content of hydroxypropyl methylcellulose can be determined by ASTM method D-2363-79 (reapproved 1989). Methyl celluloses and hydroxypropyl methylcelluloses, such as K250M, K100M, K4M, K1M, F220M, F4M and J4M hydroxypropyl methylcellulose are commercially available from The Dow Chemical Company).

Preferred cationic hydroxyethyl celluloses are those described in U.S. Pat. No. 3,472,840. Preferably the cationic hydroxyethyl celluloses have groups of the formula $[R^1R^2R^3R^4N^+]$ $(A^{z-})_{1/z}$, (II), wherein $R^1$, $R^2$ and $R^3$ each independently are $C_{1-6}$-alkyl, preferably —$CH_3$ or —$C_2H_5$, $R^4$ is —$CH_2$—CHOH—$CH_2$— or —$CH_2CH(OH)$—, $A^{z-}$ is an anion, and z is 1, 2 or 3. The cationic degree of substitution (often referred to as the CS orcationic substitution) of the cationic hydroxyethyl cellulose is in a range from about 0.075 to about 0.8, preferably about 0.15 to about 0.60. A range of about 0.15 to about 0.60 corresponds to a Kjeldahl nitrogen content of about 0.8% to about 2.5%. More preferably, the cationic hydroxyethyl cellulose has a Kjeldahl nitrogen content between 1.5 and 2.2%, which corresponds to a CS of about 0.3 to about 0.5. In one embodiment, the cationic hydroxyethylcellulose has a Brookfield LVT determined solution viscosity of from about 5 cP (=mPa·s) to about 10,000 cP, preferably from about 5 cP to about 3,000 cP, measured as a one weight percent aqueous solution at 25° C.

Combinations of two or more water-soluble cellulose derivatives are also useful. The water-soluble cellulose derivative generally has a viscosity of from 5 to 2,000,000 cps (=mPa·s), preferably from 50 cps to 1,000,000 cps, more preferably from 1,000 to 300,000 cps, measured as a two weight percent aqueous solution at 20° C. The viscosity can be measured in a rotational viscometer.

Preferred water-insoluble cellulose derivatives for use in the present invention are water-insoluble cellulose ethers, particularly ethyl cellulose, propyl cellulose or butyl cellulose. Other useful water-insoluble cellulose derivatives are cellulose derivatives which have been chemically, preferably hydrophobically, modified to provide water insolubility. Chemical modification can be achieved with hydrophobic long chain branched or non-branched alkyl, arylalkyl or alkylaryl groups. "Long chain" typically means at least 5, more typically at least 10, particulary at least 12 carbon atoms. Others type of water-insoluble cellulose are crosslinked cellulose, when various crosslinking agents are used. Chemically modified, including the hydrophobically modified, water-insoluble cellulose derivatives are known in the art. They are useful provided that they have a solubility in water of less than 2 grams, preferably less than 1 gram, in 100 grams of distilled water at 25° C. and 1 atmosphere. The most preferred cellulose derivative is ethyl cellulose. The ethyl cellulose preferably has an ethoxyl substitution of from 40 to 55 percent, more preferably from 43 to 53 percent, most preferably from 44 to 51 percent. The percent ethoxyl substitution is based on the weight of the substituted product and determined according to a Zeisel gas chromatographic technique as described in ASTM D4794-94 (2003). The molecular weight of the ethyl cellulose is expressed as the viscosity of a 5 weight percent solution of the ethyl cellulose measured at 25° C. in a mixture of 80 volume percent toluene and 20 volume percent ethanol. The ethyl cellulose concentration is based on the total weight of toluene, ethanol and ethyl cellulose. The viscosity is measured using Ubbelohde tubes as outlined in ASTM D914-00 and as further described in ASTM D446-04, which is referenced in ASTM D914-00. The ethyl cellulose generally has a viscosity of up to 400 mPa's, preferably up to 300 mPa's, more preferably up to 100 mPa's, measured as a 5 weight percent solution at 25° C. in a mixture of 80 volume percent toluene and 20 volume percent ethanol. The preferred ethyl celluloses are premium grades ETHOCEL ethyl cellulose which are commercially available from The Dow Chemical Company of Midland, Mich. Combinations of two or more water-insoluble cellulose derivatives are also useful. Preferably the water-insoluble cellulose derivative has an average particle size of less than 0.1 millimeter, more preferably less than 0.05 millimeter, most preferably less than 0.02 millimeter. Preferably the water-insoluble cellulose derivative is exposed to an edible fat or oil before being administered to an individual so that the cellulose derivative imbibes the fat or oil. Advantageously the water-insoluble cellulose derivative is exposed to an excess of the fat or oil at about 40 to 60° C.

In certain other specific embodiments, the therapeutic methods of the invention rely on the administration of a therapeutically effective amount of a naturally or recombinantly produced bacterial protein or a combination of such proteins which (i) increase the number and/or activity of one or more bacteria which are under-represented in a disease and/or (ii) decrease the number and/or activity of one or more bacteria which are over-represented in a disease. The proteins according to this embodiment may be produced by the same strain of bacteria which is intended to be regulated or by a different strain.

Prior to administering to humans, the effectiveness of the novel therapeutic compositions of the present invention can be studied in animal models of obesity, such as, e.g., sub-therapeutic antibiotic treatment (STAT) mice (Cho et al., Gastroenterology, 2009, 136(5) Supplement 1: A-102), ob/ob mice (Ley et al., Proc. Natl. Acad. Sci. USA 2005; 102: 11070-5; Turnbaugh et al., Nature 2006; 444:1027-31), db/db mice (Kobayashi et al., Metabolism, 2000, 48(1):22-31), diet-induced obesity (DIO) mice (Petro et al., Metabolism, 2004, 53(4):454-457), NOD mice (Wen et al., Nature, 2008; 455 (7216):1109-1113), etc.

Combination Treatments

For an enhanced therapeutic effect, the probiotics and/or prebiotics as described herein can be administered in combination with other therapeutic agents or regimes as discussed. The choice of therapeutic agents that can be co-administered with the probiotics and/or prebiotics of the invention depends, in part, on the condition being treated.

Non-limiting examples of additional pharmaceutically active compounds useful for treatment of obesity, metabolic syndrome, insulin-deficiency or insulin-resistance related disorders, glucose intolerance, diabetes mellitus, non-alcoholic fatty liver, abnormal lipid metabolism, atherosclerosis, and related disorders include anti-inflammatory agents, antioxidants, antiarrhythmics, cytokines, analgesics, vasodilators, antihypertensive agents including beta-blockers, angiotensin converting enzyme inhibitors (ACE inhibitors), and calcium channel blockers, inhibitors of cholesterol synthesis, cholesterol binding agents, antithrombotic agents, central modulators of appetite, and diabetes drugs. Examples of inhibitors of cholesterol synthesis or absorption which are useful in the combination therapies of the present invention include Hmg-CoA reductase inhibitors and their bio-active metabolites, such as, e.g., simvastatin, lovastatin, pravastatin, compactin, fluvastatin, dalvastatin, atorvastatin, HR-780, GR-95030, CI-981, BMY 22089, and BMY 22566. See, e.g., U.S. Pat. Nos. 4,346,227; 4,444,784; 4,857,522; 5,190,970; 5,316,765, and 5,461,039; PCT Publ. No. WO84/02131; GB Pat. No. 2,202,846. As used in the methods or compositions of the present invention, any one or several of the Hmg-CoA reductase inhibitor compounds may be mixed with L-arginine or a substrate precursor to endogenous nitric oxide, as described in U.S. Pat. Nos. 6,425,881 and 6,239,172, and 5,968,983, to provide a therapeutically effective mixture for use in conjunction with probiotics and/or prebiotics of the present invention.

Non-limiting examples of diabetes drugs useful in the combination therapies of the present invention include insulin, proinsulin, insulin analogs, activin, glucagon, somatostatin, amylin, actos (pioglitazone), amaryl (glimepiride), glipizide, avandia (rosiglitazone), glucophage, glucotrol, glucovance (a combination of glyburide and metformin), and the like. See, e.g., U.S. Pat. No. 6,610,272. The term "insulin" encompasses natural extracted human insulin, recombinantly produced human insulin, insulin extracted from bovine and/or porcine sources, recombinantly produced porcine and bovine insulin and mixtures of any of these insulin products. In accordance with the present invention, administering probiotics and/or prebiotics of the present invention in combination with insulin is expected to lower the dose of insulin required to manage the diabetic patient, while also alleviating the symptoms of metabolic syndrome.

In accordance with the present invention there may be numerous tools and techniques within the skill of the art, such as those commonly used in molecular immunology, cellular immunology, pharmacology, and microbiology. Such tools and techniques are describe in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc. Hoboken, N.J.; and Enna et al. eds. (2005) Current Protocols in Pharmacology, John Wiley and Sons, Inc.: Hoboken, N.J.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Analysis of Diet-Associated Changes in Intestinal Microbiota of Mice

Materials and Methods

1. Animals and Diets

Thirty (30) obese male C57/B16J mice (from Jackson Laboratories, Bar Harbor, Me.) were studied. All mice were fed a high fat (60% fat) diet (also termed diet-induced obesity [DIO] diet; supplied by Research Diets Inc., New Brunswick, N.J.) and water ad libitum for at least two months. Then baseline fecal samples were obtained and animals were divided in three groups of ten (10) mice each. One group was maintained on the high-fat (60% fat) diet, one group was converted to a low fat (10% fat) diet (also supplied by Research Diets Inc., New Brunswick, N.J.), and the third group was fed a 60% fat diet+HPMC. Hydroxypropyl methylcellulose (HPMC) was present at 8 percent weight level in the treatment diet. It was mixed with the powdered components of the diet. The HPMC had a methoxyl content of 19-24 percent, a hydroxypropoxyl content of 7-12 percent and a viscosity of about 250,000 mPa's, measured as a 2 wt. % aqueous solution at 20° C., and is commercially available from The Dow Chemical Company under the Trademark METHOCEL K250M hypromellose. Animals were weighted periodically. A fresh fecal pellet was collected from each individual mouse at baseline, after 2 and 4 weeks, and shortly after sacrifice and frozen at −80° C. At the time of sacrifice, the cecal and ileal contents were also frozen and stored at −80° C. for future study.

2. DNA Extraction

Approximately 10 mg each of the fecal, cecal, and ileal samples were extracted using the MoBio Powersoil 2 DNA Isolation kit (MoBio Laboratories, Carlsbad, Calif.) as per the manufacturer's instructions. This extraction method uses a combination of mechanical disruption using bead-beating and spin filtration using silica filter tubes to extract bacterial genomic DNA from each of the samples.

3. qPCR, Sequencing and Taxonomic Analysis

DNA extracted from cecal, ileal, and fecal specimens was subjected to PCR using barcoded universal primers interrogating regions V3-V5 of the 16S rRNA gene followed by 454 sequencing and taxonomic analysis.

Total eubacterial levels were determined by a standardized quantitative PCR (qPCR) using primers Eub519F: 5'-CAGCAGCCGCGGTRATA-3' (SEQ ID NO: 1) and Eu785R: 5'-GGACTACCVGGGTATCTAAKCC-3' (SEQ ID NO: 2) directed to conserved 16S rRNA fragments.

PCR reaction mixture and program (Power SYBR Green) were as follows:

| Reagents | Stock | Vol/Reac(μl) | Final |
|---|---|---|---|
| PCR Master Mix | 2x | 12.5 | 1x |
| F. primer | 10 μM | 1 | 0.4 μM |

| Reagents | Stock | Vol/Reac(μl) | Final |
|---|---|---|---|
| R. primer | 10 μM | 1 | 0.4 μM |
| BSA | 20 ng/μl | 0.125 | 0.1 ng/μl |
| Template | | 1 | |
| Total | | 25 | |

Program:
50° C. 2 min, 95° C. 10 min
95° C. 15 Seconds and
56° C. 60 Seconds 40 cycles Firmicutes levels were determined by qPCR using primers Firm934F: 5'-GGAGYATGTGGTTTAATTCGAAGCA-3' (SEQ ID NO: 3) and Firm1060R: 5'-AGCTGACGACAAC-CATGCAC-3' (SEQ ID NO: 4) directed to conserved 16S rRNA fragments.
PCR reaction and Program (Power SYBR Green) were as follows:

| Reagents | Stock | Vol/Reac(μl) | Final |
|---|---|---|---|
| PCR Master Mix | 2x | 12.5 | 1x |
| F. primer | 10 μM | 1 | 0.4 μM |
| R. primer | 10 μM | 1 | 0.4 μM |
| BSA | 20 ng/μl | 0.125 | 0.1 ng/μl |
| Template | | 1 | |
| Total | | 25 | |

Program:
50° C. 2 min, 95° C. 10 min
95° C. 15 Seconds and
60° C. 60 Seconds 40 cycles Bacteroidetes levels were determined by qPCR using primers Bact934F: 5'-GGARCATGTGGTTTAATTCGATGAT-3' (SEQ ID NO: 5) and Bact1060R: 5'-AGCTGACGACAAC-CATGCAG-3' (SEQ ID NO: 6) directed to conserved 16S rRNA fragments.
PCR reaction and Program (Power SYBR Green) were as follows:

| Reagents | Stock | Vol/Reac(μl) | Final |
|---|---|---|---|
| PCR Master Mix | 2x | 12.5 | 1x |
| F. primer | 10 μM | 1 | 0.4 μM |
| R. primer | 10 μM | 1 | 0.4 μM |
| BSA | 20 ng/μl | 0.125 | 0.1 ng/μl |
| Template | | 1 | |
| Total | | 25 | |

Program:
50° C. 2 min, 95° C. 10 min
95° C. 15 Seconds and
60° C. 60 seconds 40 cycles The samples then underwent 454 pyrosequencing (Roche) using barcoded primers designed to interrogate the 16S rRNA regions V3-V5. The average number of sequence reads obtained from fecal pellets were 5671±1981 reads, while the average number of sequence reads obtained from cecal and ileal samples were 4901±2271 and 6662±2438, respectively. The total amount of data generated in the sequencing experiment was about 0.18 Gb (180 Mb). Sequence data were summated to the phylum, class, order, family and genus levels and analyzed.

Total fungal levels were determined by qPCR using primers directed to the conserved ITS2 region in the fungal rrn operon ITS1F CTYGGTCATTTAGAGGAAGTAA (SEQ ID NO: 7) and ITS2 RCTGCGTTCTTCATCGWTG (SEQ ID NO: 8) and probe TCYGTAGGTGAACCTGCRG (SEQ ID NO: 9).

The total number of genes encoding Butyryl CoA transferase (BCoAT), regardless of the taxonomic origin of the gene, were determined by qPCR using primers BCoATscrF GCIGAICATTTCACITGGAAYWSITGGCAYATG (SEQ ID NO: 10) and BCoATscrR CCTGCCTTTGCAATRTCIA-CRAANGC (SEQ ID NO: 11). BCoAT gene number was determined by quantitative PCR using FastStart SYBR Green Master Mix (Roche) with primer concentration at 500 nM. Samples were run at the following temperature profile: 50° C. for 2 minutes, 95° C. for 10 minutes, then cycle 40 times at 95° C. for 15 seconds, 53° C. for 30 seconds, and 72° C. for 30 seconds. Positive samples were confirmed by melting curve analysis.

Bioinformatic Pipeline 1.

Figure 4:
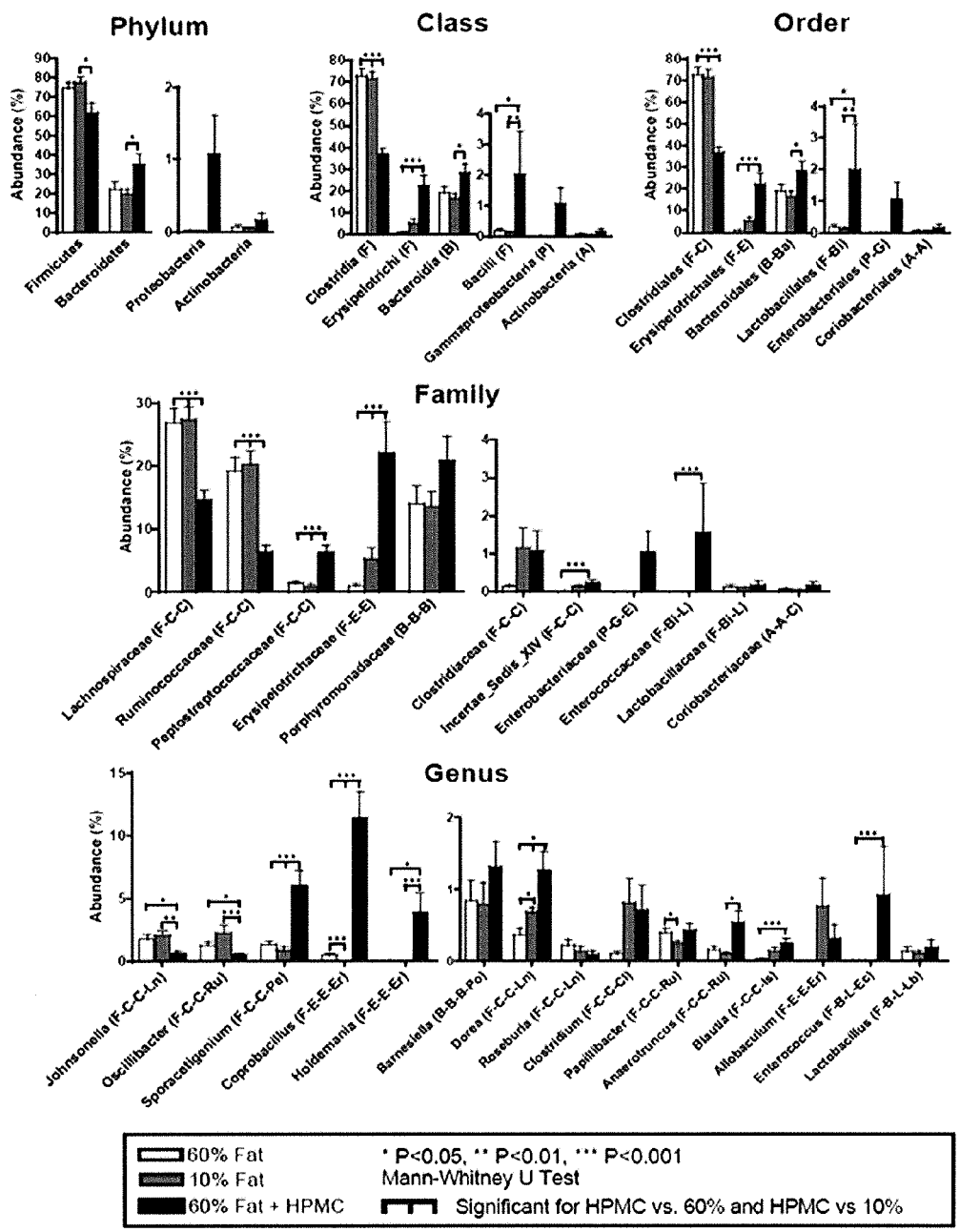
FIG. 4A is a bar diagram demonstrating that HPMC exposure significantly alters the composition of the cecal microbiome compared to mice maintained on a 60% diet or those switched to a 10% diet. Mice exposed to a 60% fat diet, then switched to a diet of 60% fat+HPMC had significant changes in cecal microbiota compared to the control mice maintained on the 60% fat diet alone. Notably, there were marked increases in populations of *Coprobacillus, Sporacetigenium, Holdemania, Dorea, Enterococcus*, and *Blautia*, as well as marked decreases in *Johnsonella*, and *Oscillibacter*. Little change in cecal microbiota was observed in mice switched from a 60% fat diet to a 10% fat diet, compared to the control mice maintained on a 60% fat diet. Observed changes include an increase in *Dorea*, and a decrease in *Coprobacillus* and *Papillibacter*. Note that at each level of taxa, there are two scales for abundances.
FIG. 4B is a summary table of significant changes in the cecal microbiome seen in FIG. 6 at different taxonomic levels.
Figure 5:
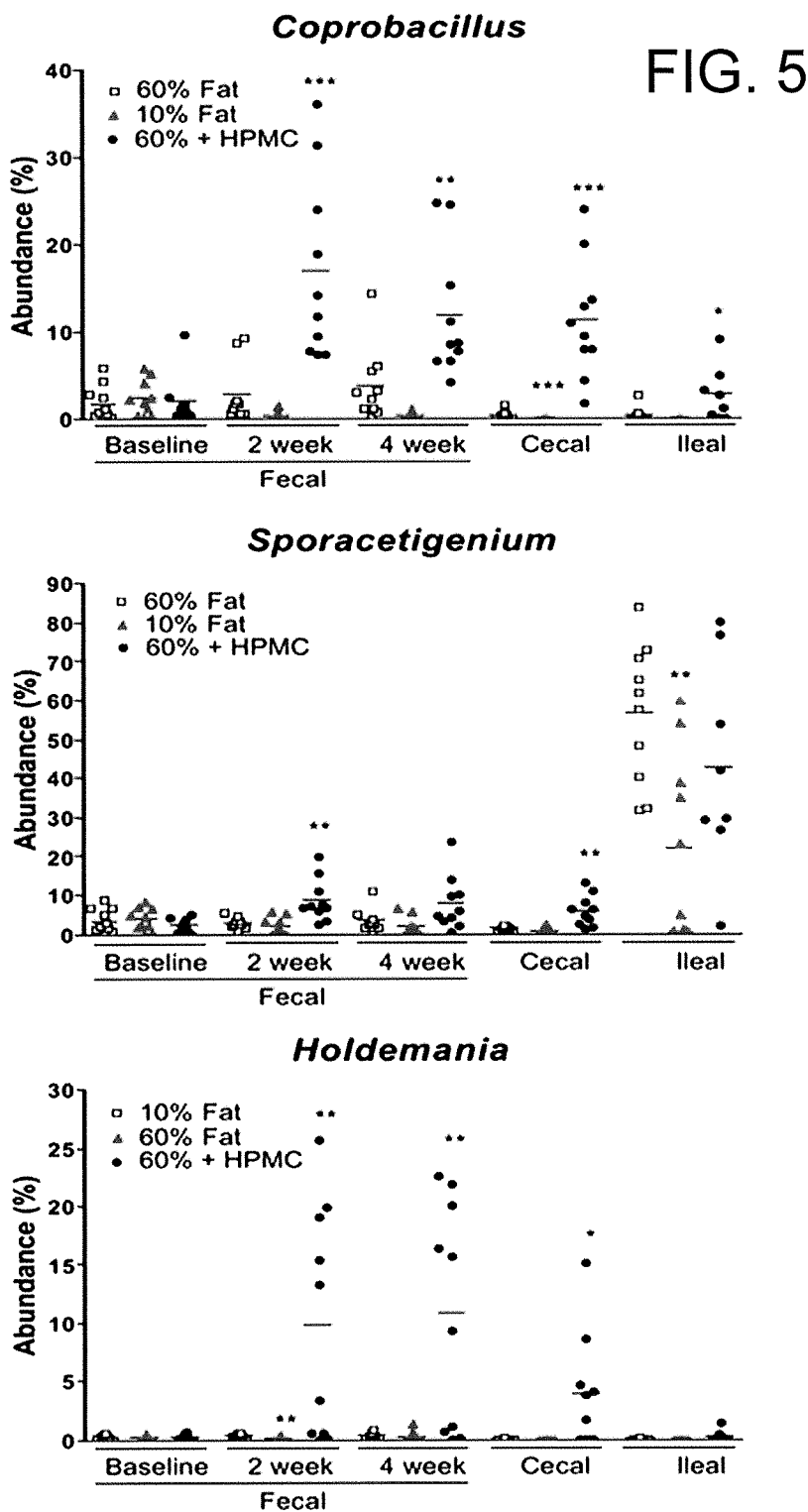
FIG. 5 represents scatterplots showing relative abundance of *Coprobacillus, Sporacetigenium* and *Holdemania* in fecal, cecal, and ileal samples from C57B6 mice on diets consisting of 60% fat 10% fat, or 60% fat+HPMC. The figure demonstrates that HPMC exposure significantly increases *Coprobacillus, Sporacetigenium*, and *Holdemania* abundance. The effects of HPMC on *Coprobacillus* and *Holdemania* are seen primarily in the cecum and are noted in the 2 and 4 fecal specimens as well. *Sporacetigenium* census was higher in the ileum than in the cecum or in fecal pellets for all groups. * $P<0.05$,  $P<0.01$, * $P<0.001$.

After the completion of sequencing, a read processing pipeline consisting of a set of modular scripts designed at the JCVI were employed for deconvolution, trimming, and quality filtering. First reads were deconvoluted or assigned to samples based on their unique 10 nt barcode allowing no more than a one nt mismatch to the barcode. After deconvolution, barcode and 16S primer sequences were removed allowing a maximum of 6 mismatches to the 16S primer and a maximum primer to barcode distance of 3 nt. Reads with an average length of <100 nt, and reads with 'Ns' were removed. A Blastn quality check was performed against an internal data set of 16S reads to remove any sample reads not consistent with 16S gene sequences in which at least 30% of the query must be covered by the alignment (60 nt minimum). Passing reads were subsequently checked for chimeras using a modified version of the RDP Chimera Check, using a reference data set maintained in-house. Remaining reads were then classified to lowest taxonomic level possible using the RDP Classifier with 80% confidence. Taxonomic results were then converted to relative abundance or ratios for each sample, and the difference between was calculated with the Mann-Whitney U test (means± and ratios depicted in FIGS. 4-6).

Results

Correlations between Diets and Weight Gain

In the group which was continuously fed high fat (60% fat) diet, animals gained weight. In the group where HPMC was added to the high fat (60% fat) diet, animals stopped gaining weight as soon as HPMC was added. And animals switched to the low fat (10% fat) diet lost weight. These observations were consistent with prior observations of the role of HPMC in controlling metabolic syndrome, diabetes mellitus and obesity, and in promotion of weight loss or maintenance of the desired body weight (see the Background section, above).

Intestinal Populations of Microorganisms

The present inventors set to investigate whether weight gain associated with high fat (60% fat) diet and the absence of such weight gain upon the addition of HPMC to the same diet correlates with changes in intestinal microbiota.

Eubacteria

Figure 3:
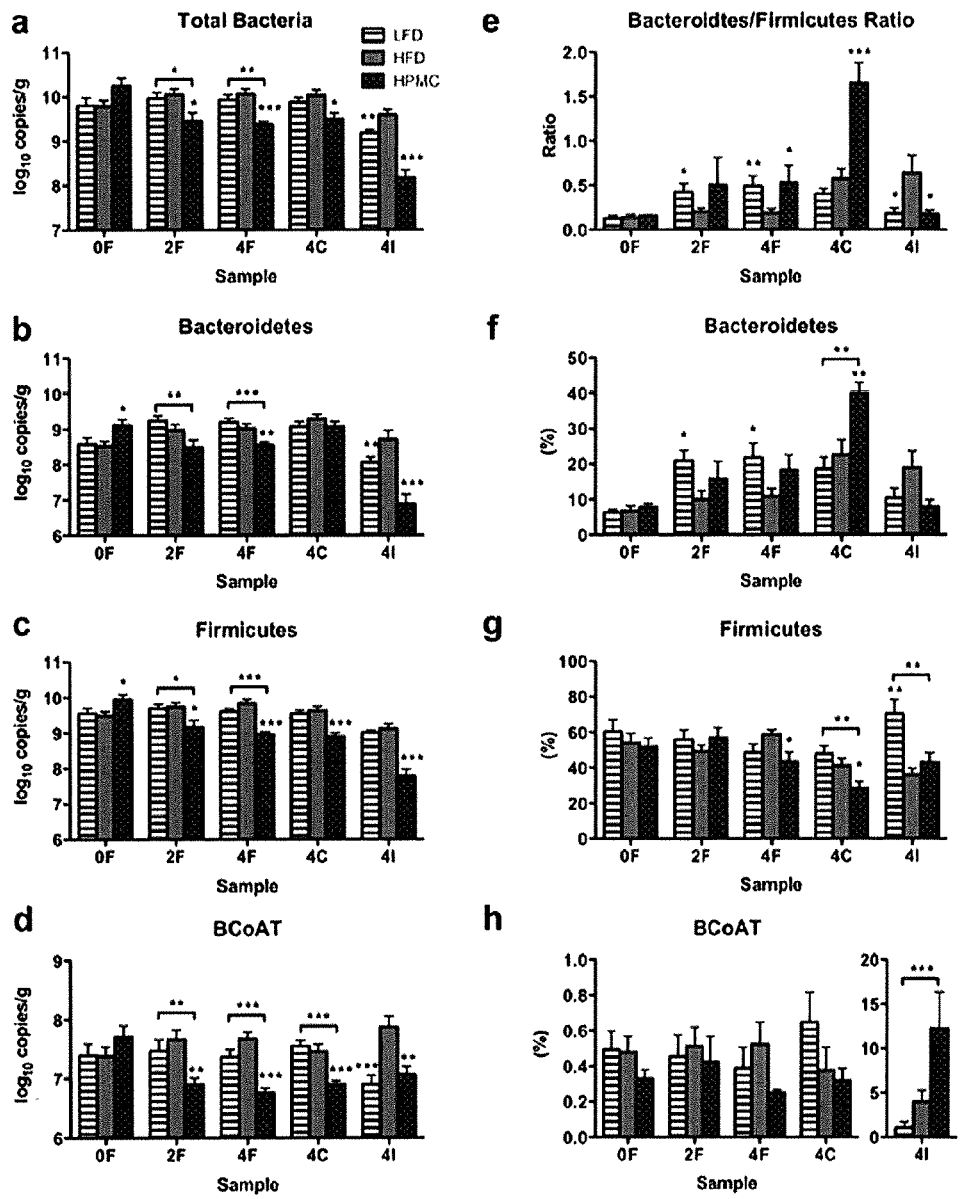
FIGS. 3*a*-3*h* are plots of quantitative PCR analysis of the intestinal microbiota. Analysis of fecal, cecal, and ileal samples measuring population copy number per gram of sample of a) total bacteria, b) Bactoidetes, c) Firmicutes, d) BcoAT, e) ratio of Bacteroidetes/Firmicutes, and relative abundance (%) of 0 Bacteroidetes, g) Firmicutes, h) BcoAT, * $p<0.05$,  $p<0.01$, * $p<0.001$, Mann-Whitney U test.

As demonstrated in FIG. 3a, at baseline, mice had 9-10 log 16S copies/g of fecal pellet without significant differences between the three groups. At 2 weeks, Eubacterial (total bacteria) counts rose slightly in the 10% fat and 60% fat groups, and fell in the 60% fat+HPMC group, but none of the changes were statistically significant. By 4 weeks, levels in the 10% fat and 60% fat groups were unchanged, but the 60% fat+HPMC group was significantly lower. The levels in the cecum at sacrifice were very similar to the 4 week results, as expected, with the same lower trends for the 60% fat+HPMC group. The ileal samples at sacrifice were lower, especially in the 60% fat+HPMC group. Thus, there is consistency in the decrease observed in the 60% fat+HPMC group with respect to the baseline, in the 2-week, 4-week, cecal, and ileal samples. These data provide evidence that adding HPMC to the diet lowers total Eubacterial populations with reference to the other two groups.

The Eubacterial populations within each group of 10 mice were also analyzed over the study period. For the mice maintained on the 60% fat diet, and the mice converted to the low fat (10% fat) diet, there were no significant differences over time (comparing Basline, 2-week, and 4-week samples). However, for the mice converted from the 60% fat diet to the 60% fat+HPMC diet, there was a progressive and significant decline between Basline and 4-week samples. In all 3 diet groups, ileal levels were 0.5-1.0 $\log_{10}$ lower than in cecum.

Firmicutes

As demonstrated in FIG. 3c, results for Firmicutes were generally similar to those for all Eubacteria. This internal consistency is not surprising since Firmicutes represent the major population within Eubacteria in the mammalian intestinal tract. At baseline, the Firmicutes populations of all three groups were similar, as expected, but by the second week, the population in the 60% fat+HPMC group was trending lower, and, in the 4-week sample, cecal and ileal samples were significantly lower than in the two other diet groups.

There were no differences over time in the group of mice maintained on the 60% fat diet, or changed to the 10% fat diet, but there was a progressive and significant decrease in the 60% fat+HPMC group. Ileal populations also were significantly lower (0.5-1.0) than in the cecal samples.

Bacteroidetes

As demonstrated in FIG. 3b, Bacteroidetes populations were not substantially different in mice on the 3 diets at baseline or at 2 weeks, however, by 4 weeks, and in the ileal samples, levels were lower in the 60% fat+HPMC group than in the other two groups. After mice were switched from the 60% fat diet to the 10% fat diet, Bacteroidetes levels rose significantly. Thus, changing from the 60% fat diet to a low fat (10%) diet or adding HPMC to the 60% fat diet perturbed the Bacteroidetes numbers, but in apparently opposite directions.

Fungal Populations

Fungal concentrations were much lower than were measures for Eubacteria, with a median of 4.0-5.0 $\log_{10}$ 16S copies/g. There were no significant differences between the groups fed different diets or over time. Ileal concentrations were higher than cecal, opposite to the Eubacterial concentrations, but the differences were not significant.

Ratios Between Populations

Firmicutes/Eubacteria (F/E)

Firmicutes represented a median of 40% to 60% of the total bacterial population in the fecal specimens. As shown in FIG. 3g, no trends over time in the Firmicutes/Eubacteria (F/E) ratios were present comparing the three groups of mice put on different diets. However, the mice who switched to the low (10%) fat diet had ratios that were significantly lower in the cecal samples than mice fed the 60% fat+HPMC diet, and higher in the ileal samples than mice fed the 60% fat diet. The intragroup comparisons did not show any significant differences for the fecal specimens over time.

Bacteroidetes/Eubacteria (B/E)

Inversely from the Firmicutes/Eubacteria (F/E) ratio, the Bacteroidetes/Eubacteria (B/E) ratios in the cecal specimens were significantly higher for animals fed the 60% fat+HPMC diet than for mice fed either the 10% fat or 60% fat diet (FIG. 3f). Changing the diet from 60% fat at baseline to 10% fat also was accompanied by a significant increase in the B/E ratio over 4 weeks, with the major increase occurring by 2 weeks.

BCoAT Studies

Microbes can contribute to obesity through fermentation of non-digestible carbohydrates in the colon to short chain fatty acids, such as acetate, butyrate, and propionate. See Bergman, Physiol Rev 1990; 70:567-90; Wong et al., J Clin Gastroenterol 2006; 40:235-43; Pryde et al., FEMS Microbiol Lett 2002; 217:133-9; Wolfe, Microbiol Mol Biol Rev 2005; 69:12-50. This process represents a 75% energy conversion to a product that is readily absorbed in the intestine, contributing 10% of host caloric intake. Butyrate is the preferred energy source for colonocytes. Butyryl CoA transferase (BCoAT) is critical for butyrate synthesis. See, e.g., Charrier et al., Microbiol., 2006, 152:179-85; Duncan et al., Appl. Environ. Microbiol., 2002, 68:5186-90; Louis and Flint, Appl. Environ. Microbiol., 2007, 73:2009-12. The BCoAT-encoding gene is widely conserved in intestinal bacteria.

The present inventors have hypothesized that the change in diet, and, specifically, the addition of HPMC, affects intestinal energy metabolism. This hypothesis was tested by examining the number of copies of BCoAT genes, as well as the ratio of BCoAT genes, relative to major taxonomic groups (FIGS. 3d and h).

Inter-Group Comparisons of BCoAT Copy Number

As shown in FIGS. 3d and h, at baseline, most fecal samples had between 7 and 8 $\log_{in}$ BCoAT copies detected, and, as expected, there were no significant differences between the three diet groups. After 2 weeks, the number of BCoAT copies in feces was significantly lower in the 60% fat+HPMC group versus the 60% fat group. After 4 weeks, the BCoAT numbers in feces were significantly lower than in both of the other groups, which also was found in the cecal samples at sacrifice. Thus, in 3 different groups of specimens, BCoAT populations were significantly different after HPMC was added to the diet. In the ileal samples, the highest BCoAT levels were in the 60% fat group, with significantly lower levels in the 10% fat and 60% fat+HPMC groups. Thus, these studies confirm the hypothesis that addition of HPMC lowers BCoAT levels in relation to the other groups, in a manner predicted to lower butyrate availability and energy production.

Intra-Group Comparisons of BCoAT Copy Number

There were no significant differences from baseline over 4 weeks in the 10% fat and 60% fat groups. However, in the 60% fat+HPMC group, there was a progressive and significant decline in BCoAT levels of about 1 $\log_{10}$ (90% reduction). This is both statistically and biologically significant.

Relationship of BCoAT Copy Number to Taxonomic Findings-Inter-Group Analyses

There were no significant differences in the ratio of BCoAT genes to numbers of total bacteria, Firmicutes, or Bacteroidetes, with three exceptions. In the ileal samples, the BCoAT/total bacteria ratios and the BCoAT/Firmicutes ratios were significantly higher in the 60% fat+HPMC group compared with the 10% fat group. In both cases, the 60% fat group was intermediate, but the differences were not significant. The BCoAT/Bacteroidetes ratios rose significantly from the 10% fat group to the 60% fat+HPMC group. These results provide evidence that the energy metabolism in proportion to the numbers of Firmicutes and Bacteroidetes changed in the ileum depending on diet. No other changes were significant.

Relationship of BCoAT Copy Number to Taxonomic Findings-Intra-Group Analyses

There were no significant differences between the baseline, 2 week, or 4 week samples with only a single exception. Mice fed the 10% fat diet had a progressive and significant decrease in the BCoAT/Bacteroidetes ratios over four weeks.

Comparison of Sequence Data at Baseline, 2 Weeks, and 4 Weeks

Figure 16:
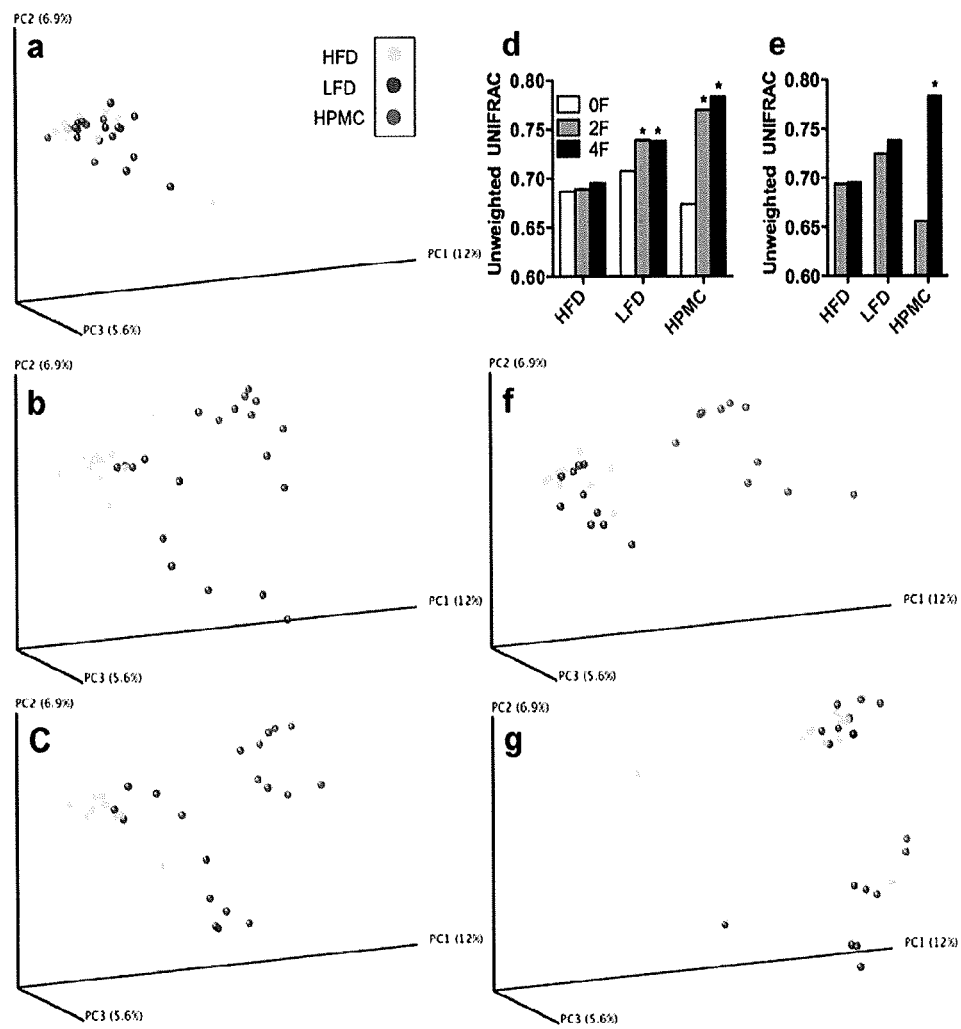
FIGS. 16a-16g show the effect of diet and fiber on microbial community structure. PCA analysis of the unweighted UniFrac distances of microbial 16S rDNA sequences from the V3-5 region in fecal samples at week 0 (baseline) (a), week 2 (b), and week 4 (c), cecal samples at sacrifice (f), and ileal samples at sacrifice (g). Unweighted UniFrac distances in LFD, HFD, and HPMC mouse fecal samples comparing community distance from 0 weeks (d) and from 2 weeks (e), * p<0.001. Three principal components were plotted by KiNG Kinetic Image, Next Generation version 2.16 with each sample represented as a circle.
Figure 18:
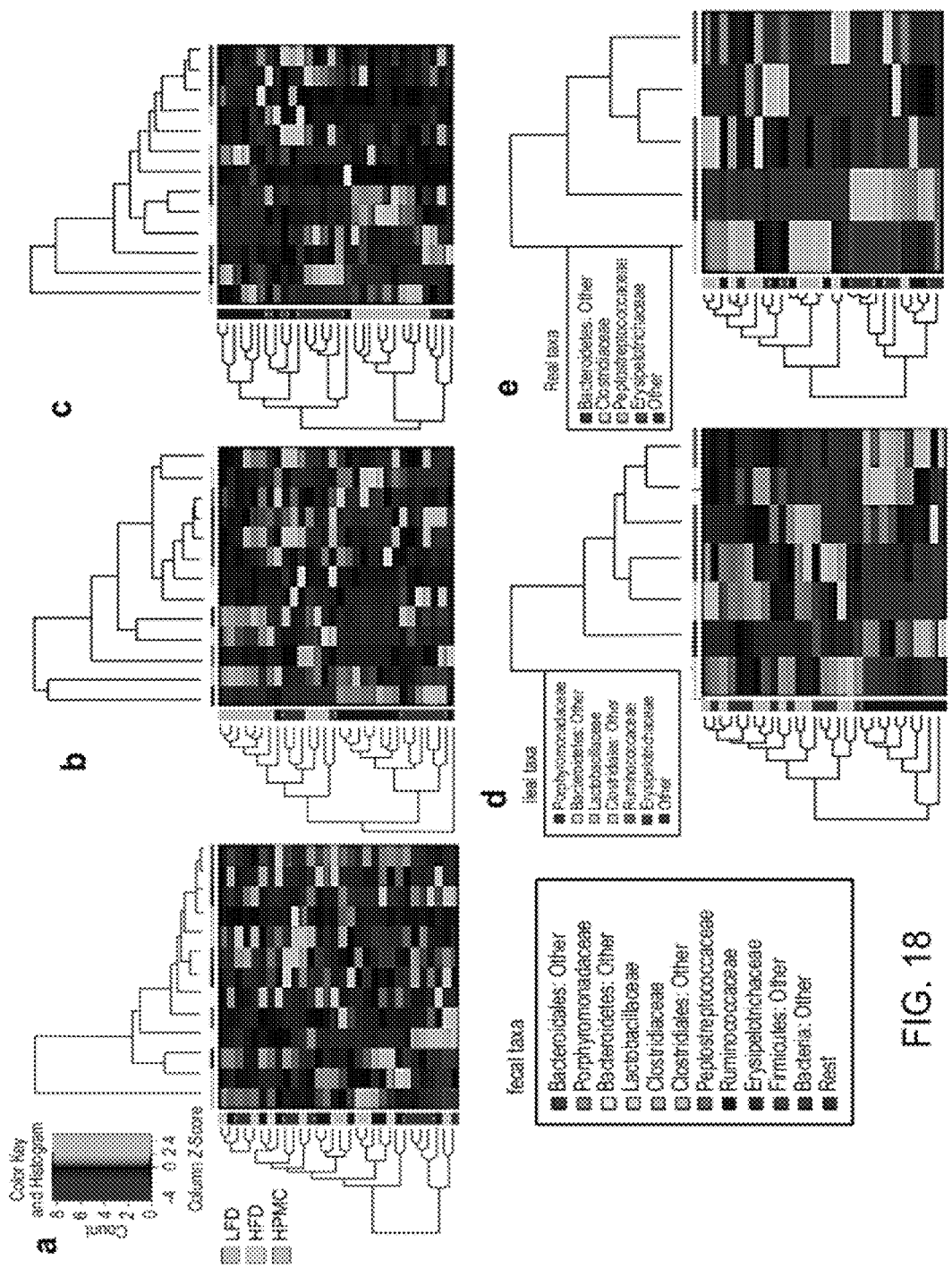
FIGS. 18a-18e show phylogenetic differences between treatment groups. Heat map of intestinal microbiome. Representation of relative abundance of predominant taxa classified at the family level (columns) for 30 individual mice on the three different diets (rows) in (a) week-0 fecal, (b) week-2 fecal, (c) 4-week fecal, (d) cecal, and (e) ileal samples.

Sequence data extracted from fecal pellets obtained from study mice at baseline, 2 weeks, and 4 weeks was compared using heat map (FIG. 18) and principal component analysis (PCA) plots (FIG. 16). At baseline, the distribution of the mice based on the genus level microbial composition of their fecal pellets was random. This was corroborated by unsupervised hierarchical clustering analysis at the same taxonomic level in an NMDS analysis. This was an expected result because all mice to this point had been raised and fed under identical conditions (60% fat diet). After 2 weeks of intervention, mice in each of the 3 study groups began to cluster, although the clustering was not statistically significant at this intermediate time point. By 4 weeks, there was significant clustering of the mice into their respective study groups. In a heat map analysis, there were three distinct deep branch points (termed I, II, and III). In branch I, 7 of the 10 mice were from the 60% fat+HPMC group. In branch II, 9 of the 10 mice were from the 60% fat group. In branch III, 7 of the 10 mice were from the 10% fat group. The clustering was corroborated in NMDS plots, in which all the 60% fat+HPMC mice were adjacent, and most of the 60% fat mice also were contiguous. These data demonstrate that there are significant and consistent effects of the diets on the intestinal microbiota of mice that are observable within 4 weeks of initiation.

Comparison of Cecal and Ileal Samples

Comparison of the sequencing data obtained from ileal and cecal samples also was accomplished by heat map analysis. Ileal samples generated 2 deep branch points containing 18 and 10 mice. In the larger branch of 18 mice, 14 were exposed to the 60% fat diet (9 on 60% fat and 5 mice on 60% fat+HPMC) while the branch of 10 mice was primarily composed of mice exposed to the 10% fat diet. The data obtained from the cecal samples generated three branch points (termed I, II, and III). The most notable finding is in branch III, in which 10 of 10 mice were exposed to the 60% fat+HPMC diet. Branch I consisted primarily of the 10% fat group (6/10 mice) and branch II consisted of the 60% fat group (5/9 mice). These findings suggest that HPMC exposure has a more significant effect on the microbiome found in the cecum than in the ileum. This is consistent with the fact that the microbial numbers in the cecum and thus their metabolic contributions are likely greater than anywhere else in the gastrointestinal tract (see, e.g., Turnbaugh et al., Nature 2006, 444(7122):1027; Qu et al., PLoS One 2008, 3(38):e2945).

Alterations of the Taxonomic Composition Caused by Exposure to HPMC

Comparison of microbial abundance in the cecal samples obtained from 10% fat, 60% fat, and 60% fat+HPMC groups is shown in FIG. 4a and is summarized in FIG. 4b. In comparing the three study groups, the differences between the 10% fat and 60% fat groups were relatively modest, with the most notable changes at the genus level, an increase in *Dorea*, and decrease in *Coprobacillus* and *Papillibacter* was observed. No changes were found at higher taxonomic levels. However, when comparing the 60% fat+HPMC group to the other two diets, there were marked and significant differences at multiple taxonomic levels. Notable changes in genera are seen in the decrease of *Oscillibacter* (Iino et al., Int. J. Syst. Evol. Microbiol., 2007, 57:1840-1845; Walker at al., ISME J., 2010, 1-11) and *Johnsonella* (Moore and Moore, Int. J. Syst. Bacteriol., 1994, 44(2):187-192) as well as in the marked increase in *Coprobacillus* (Kageyama and Benno, Microbiol. Immunol., 2000, 44(1):23-28), *Sporacetigenium* (Chen et al., Int. J. Systematic Evol. Microbiol., 2006, 56:721-725), and *Holdemania* (Willems et al., Int. J. Systematic Bacteriol., 1997, 47(4):1201-1204) (FIG. 5) and slight increase in *Dorea, Blautia*, and *Enterococcus*.

By 454-pyrosequencing, at the family level, 60% fat+HPMC groups showed a marked increase in Erysipelotrichaeceae and Peptostreptococcaceae, a slight increase in Clostridiales Insertae Sedis XIV, and Enterococcaceae, and a decrease in Lachnospiraceae and Ruminococcaceae when compared to the 60% fat control mice. At the order level, there was an increase in Erysipelotrichales and Lactobacillales, and a decrease in Clostridiales. At the Class level, there was an increase in Erysipelotriche and Bacilli, and a decrease in Clostridia. There was a downward trend in Firmicutes relative abundance (P=0.065 by Mann-Whitney U) and an upward trend in Bacteroidetes relative abundance (P=0.076). There were no statistically significant changes between 60% fat+HPMC and the 60% treatment groups at the phylum level, although the decrease in Firmicutes neared significance (p=0.065).

When cecal microbiota abundance in mice on 60% fat+HPMC diet is compared to mice on the 10% fat diet, the changes in taxa are similar to the comparison between 60% fat+HPMC and 60% fat with the following exceptions. There is a significant increase in Bacteroidetes (phylum), Bacteroidia (class), Bacteroidales (order), and Anaerotruncus (genus) in the 60%+HPMC group. There is no significant difference in Clostridiales Insertae Sedis XIV, Enterococcaceae (family), *Blautia*, or *Enterococcus* (genus).

Summary of 454 Sequencing Data

These data provide strong evidence that adding HPMC to a 60% diet changes the population composition of the intestinal microbiota. Clustering of the groups based on sequence data demonstrates that the dietary interventions, both of 60% fat diet and 60% fat+HPMC diet, caused consistent and significant changes at the genus level in the composition of the gut microbiome. The data also show that the primary effect of the HPMC may be in the cecum, rather than in the ileum. Finally, the addition of HPMC to the diet caused significant shifts in the composition of the gut microbiome, more than simply diet alone.

Conclusions

The above data provide evidence that adding HPMC to a 60% fat diet changes the population size and composition of the intestinal microbiota. The data are internally consistent and show reductions in total bacterial populations, primarily reflecting reduction in Firmicutes. Diet change also affects Bacteroidetes populations. The fact that the changes were in the same direction and to a similar degree supports the hypothesis that adding HPMC affects the microbiota in ways equivalent to lowering dietary fat content. The 454 sequencing data confirmed the consistency of the findings.

Figure 6A:
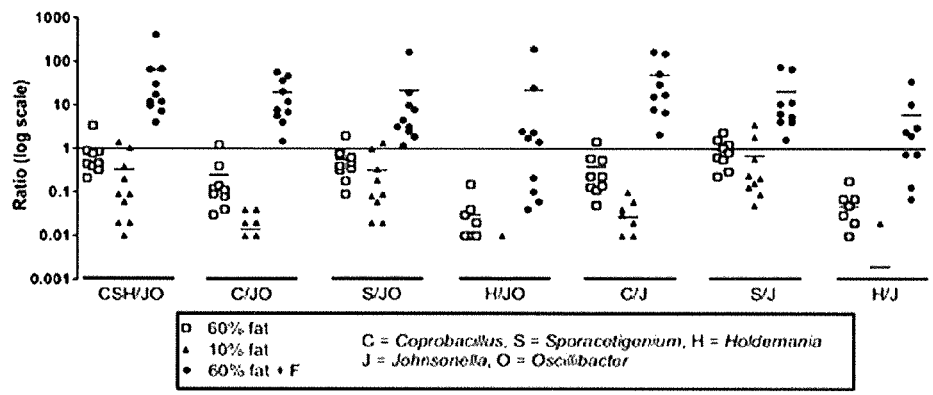
FIG. 6 is a scatter plot of ratios that represent diagnostic criteria for predicting predisposition to weight gain on a high fat diet and effectiveness of fiber treatment for weight loss or weight gain prevention. C57B6 mice were maintained on a 60% fat diet for 2 months, then 1 group was switched to a 10% fat diet, another switched to a 60% fat+HPMC diet, and a $3^{rd}$ group was maintained on the 60% fat diet. A. Ratios at the genus level are calculated by dividing the sum of any combination of *Coprobacillus, Sporacetigenium*, and/or *Holdemania* (CSH) by any combination of *Johnsonella* and/or *Oscillibacter*. A ratio below 1 indicates a state that is predisposed to weight gain while a ratio above 3 indicates a state that has a high propensity to prevent weight gain. A ratio between 1 and 3 is intermediate. B. Additional ratios for CSH are calculated by dividing the sum of any combination of *Coprobacillus, Sporacetigenium*, and/or *Holdemania* by the phylum Firmicutes to measure the relative abundance. A ratio below 0.1 indicates a state that is predisposed to weight gain while a ratio above 0.1 indicates a state that has a high propensity to prevent weight gain. C. Ratios at the family level are calculated by dividing the sum of any combination of Erysipelotrichaceae and/or Peptostreptococcacea by Lachnospiraceae and/or Ruminococcaceae. A ratio below 0.1 indicates a state that is predisposed to weight gain while a ratio above 0.1 indicates a state that has a high propensity to prevent weight gain.
Figure 6B:
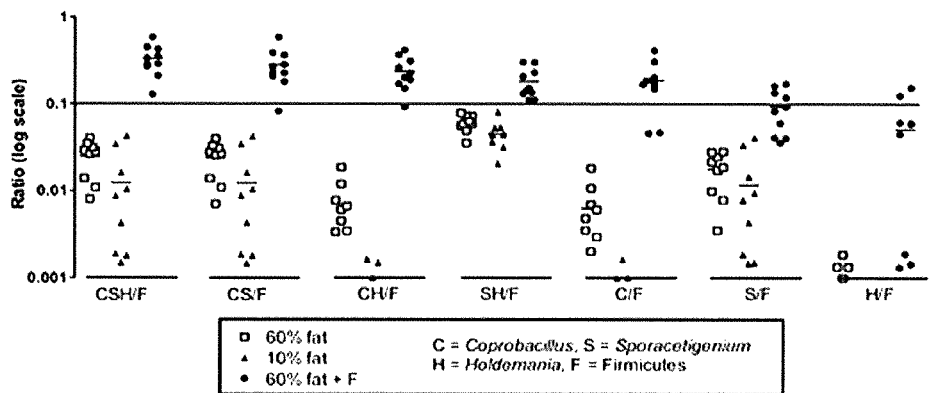
Figure 6C:
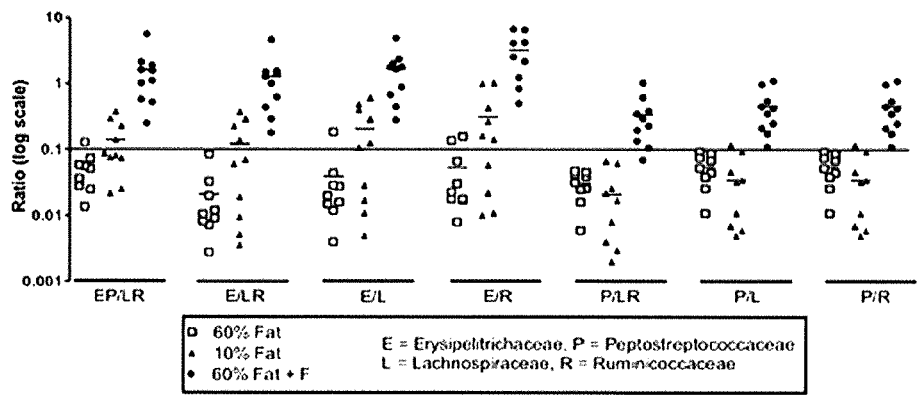

The data provided herein with respect to specific changes also allows to develop various diagnostic methods for predicting predisposition to weight gain on a high fat diet and effectiveness of fiber (e.g., HPMC) treatment for weight loss or weight gain prevention. As shown in FIGS. 6A-B, a useful diagnostic ratio at the genus level can be developed by dividing the sum of any combination of *Coprobacillus, Sporacetigenium*, and/or *Holdemania* (i.e., C+S+H or C+H or C+S or S+H or C or S or H) by any combination of *Johnsonella* and/or *Oscillibacter* (i.e., J+O or J or O), wherein a ratio below 1 indicates a state that is predisposed to weight gain while a ratio above 3 indicates a state that has a high propensity to prevent weight gain. Additional diagnostic ratios can be developed by dividing the sum of any combination of *Coprobacillus, Sporacetigenium*, and/or *Holdemania* (i.e., C+S+H or C+H or C+S or S+H or C or S or H) by the phylum Firmicutes (F), wherein a ratio below 0.1 indicates a state that is predisposed to weight gain while a ratio above 0.1 indicates a state that has a high propensity to prevent weight gain. As shown in FIG. 6C, useful diagnostic ratios can be also developed by dividing the sum of any combination of Erysipelotrichaceae and/or Peptostreptococcacea by Lachnospiraceae and/or Ruminococcaceae, wherein a ratio below 0.1 indicates a state that is predisposed to weight gain while a ratio above 0.1 indicates a state that has a high propensity to prevent weight gain.

Example 2

A Cholesterol-Lowering Dietary Fiber Perturbs the Murine Intestinal Microbiota

Materials and Methods

Animals and Diets were the same as in Example 1, supra.
Hepatic Lipid Analysis.

Lyophilized liver samples were extracted using an accelerated solvent extractor (Dionex ASE, Sunnyvale, Calif.) at 100° C., ~13.8 MPa with 75/25 hexane/2-propanol, dried and weighed to determine the percentage of total hepatic lipids, and hepatic total cholesterol, free cholesterol, and triglyceride levels (Roche Diagnostic/Hitachi 914 clinical analyzer).

Fecal Lipid Analysis.

Fecal lipids were extracted on a Dionex ASE system using a mixture of hexane and 2-propanol (3:2, v/v, 2% acetic acid) at 15 MPa and 60° C. for 30 min, then divided into two aliquots. The first sample was analyzed for saturated and unsaturated fatty acid composition by GC separation. Briefly, the fatty acids in the lipid extract were methylated using boron trifluoride methanol27, and the derivatized samples analyzed by gas chromatography Agilent 6890 series GC, with a flame ionization detector and a DB-23 analytical column (Agilent, Santa Clara, Calif.). The initial oven temperature was 200° C. for 5 min, then increased to 250° C. at 5° C./min and held for 5 min. A calibration solution was prepared to contain 2 mg/mL of methyl palmitate (C16:0), methyl stearate (C18:0), methyloleate (C18:1), methyl linoleate (C18:2), and methyl linolenate (C18:3), and 11 µg/mL methyl erucate (Nu-chek, Elysian, Minn.) in heptane. The second aliquot was analyzed for total bile acids and sterols using a modified chromatographic method28. Briefly, using a 1200RR HPLC system (Agilent) with an Acquity BEH C18 column [1.7 µm, 2.1×100 mm; (Waters)], a reversed-phase separation was performed with a gradient of two mobile solvent phases: (A) methanol/acetonitrile/water (53:23:24, v/v/v) and (B) 2-propanol (100%). Crystalline ammonium acetate was added to each phase to form a 30 mM solution. Solvent A was acidified by adding 2.4% (v/v) glacial acetic acid. A linear gradient at a flow rate of 0.25 mL/min was performed as follows: 0-6 min, 4-36% B; 6-8 min, 36-48% B; 8-17 min, 48-51% B; 17-18 min, 51-73% B; 18-31 min, 73-85% B; and 31-34 min, 85-96% B. In all experiments, the columns were re-equilibrated between injections with the initial mobile phase (10 mL). The LC effluent was monitored using a Corona Plus charged aerosol detection apparatus (CAD; ESA Biosciences, Chelmsford, Mass.) with a nebulizer temperature at 30° C.

Plasma Biomarker Analysis.

Total cholesterol, free cholesterol, and triglycerides in plasma were determined by enzymatic colorimetric assays using a Roche Diagnostics/Hitachi 914 Clinical Analyzer with assay kits from Roche Diagnostics (Indianapolis, Ind.) and Diagnostic Chemicals, Ltd. (Oxford, Conn.). The concentrations of plasma, LDL-cholesterol and HDL-cholesterol were determined using L-type LDL-cholesterol (Roche Diagnostics) and L-type HDL-cholesterol [Wako Chemicals (Richmond, Va.)] assay kits. The VLDL-cholesterol levels were calculated by subtracting HDL-cholesterol and LDL-cholesterol from total cholesterol levels. Plasma concentrations of adiponectin, leptin, and insulin of 12 h-fasted mice were determined using mouse adiponectin (B-Bridge International, Sunnyvale, Calif.), leptin (Assay Designs, Ann Arbor, Mich.), and insulin (Mercodia Inc., Winston Salem, N.C.) immunoassay kits, as described15. Fasting glucose levels were measured by collecting blood from each mouse by the tail-prick approach. A drop of blood collected by a sterile needle was analyzed using a OneTouch®Ultra® meter with FastDraw™ test strips (Johnson & Johnson, Milpitas, Calif.).

PCR Amplifcation.

After genomic DNA extraction and quantification, samples were prepared for amplification and sequencing at the JCVI Joint Technology Center (JTC). Genomic DNA sample concentrations were normalized to ~2-6 ng/µl. The V3-V5 region of the 16S rRNA gene was amplified using forward primer 341F (5'-CCTACGGGAGGCAGCAG-3' (SEQ ID NO: 12)) and reverse primer 926R (5'-CCGTCAATTCMTTTRAGT-3' (SEQ ID NO: 13)). A barcoded primer design was completed using a set of algorithms developed at the JCVI. The 'A' and 'B' adapters for 454 library construction were included as a part of the PCR primers. To the 926R primer, 10 nt barcodes were included as part of the primer design (5'-A-adapter-N (10)+16S primer-3'). This design allowed for the inclusion of a unique barcode to each sample at the time of PCR so that the tagged samples could be multiplexed for sequencing. Every effort was made to prevent contamination of PCR reactions with exogenous DNA including a set of reactions in a laminar flow hood. PCR reactions were completed as follows (per reaction): 2 µL of gDNA, 1× final concentration of Accuprime PCR Buffer II (Invitrogen, Carlsbad, Calif., USA), 200 nM forward and reverse primers, 0.75 units of Accuprime Taq DNA Polymerase High Fidelity (Invitrogen, Carlsbad, Calif., USA), and nuclease-free water to bring the final volume to 204. PCR cycling conditions were: initial denaturation of 2 minutes at 95° C. followed by 30 cycles of 20 seconds at 95° C., 30 seconds at 50° C., and 5 minutes at 72° C. A negative control (water blank) reaction also was included and examined after 35 cycles. PCR reactions were visualized on 1% agarose gels and quantified using a Tecan SpectraFluor Plus (Tecan Group Ltd., Mannedorf, Switzerland). Each reaction was cleaned individually using the Agencourt AMPure system (Beckman Coulter Genomics, Danvers Mass., USA) prior to normalization and pooling of samples for sequencing.

Sequencing.

The pooled samples were further cleaned using the Agencourt AMPure system (Beckman Coulter Genomics, Danvers Mass., USA) prior to emulsification (em)PCR. Steps for emPCR, enrichment and 454 sequencing were performed by following the vendor's standard operating procedures with some modifications. Specifically, qPCR was used to accurately estimate the number of molecules needed for emPCR. We also utilized automation (BioMek FX) to "break" the emulsions after emPCR, and we used butanol to enable easier sample handling during the breaking process.

Bioinformatic Pipeline 2.

The Qiime pipeline (Caporaso et al., Nat Methods 7, 335-336, 2010) was used to further process the sequences. The sequences were first grouped into operational taxonomic units (OTUs) with a sequence similarity threshold of 97%, then taxonomic assignment was generated using the RDP database and Qiime algorithm. This data was used to produce the operational taxonomic unit (OTU) absolute abundance table and weighted UniFrac beta-diversity matrix (Lozupone et al., UniFrac: an effective distance metric for microbial community comparison. ISME J 2010; Lozupone et al., Appl Environ Microbiol 71, 8228-8235, 2005). Principle component analysis (PCA) plots were produced based on unweighted UniFrac distances. The rarefactions for richness and Shannon diversity indices were calculated in R statistical programming environment (R: A Language and Environment for Statistical Computing, in R Foundation for Statistical Computing, Vol. 1, 2009; Gentleman et al., Genome Biol 5, R80, 2004) using Community Ecology Package vegan. Comparison of unweighted and weighted UniFrac distances was performed using two-sided t-test. The OTU absolute abundances were converted to relative abundances by normalizing to total sequence count per sample analyzed. The resulting relative abundance matrix was used to produce heatmaps for major (relative abundance >1%) taxa.

Comparison of Bioinformatic Pipeline 2 to Bioinformatic Pipeline 1 Used in Example 1.

The taxonomic data in Example 1 was derived from a bioinformatic pipeline that matched the 16S sequence reads to sequences in the Ribosomal Database Project (RDP) (Wang et al., Applied and Environmental Microbiology 73, 5261-5267, 2007) using the RDP classifier with an 80% confidence. In bioinformatics pipeline 2 analysis (FIGS. 7-12), the same sequence data was first grouped into OTU's at a 97% sequence similarity, then assigned a taxonomic name using the Qiime pipeline and RDP database. The taxonomic data varies between the two data sets generated by the automated RDP classifier (Example 1, FIGS. 4-6) and generated by the automated Qiime taxonomic assignment tool, because they represent two independent algorithms that aim to assign microbial taxonomic names to sequence data. Diet-mediated alterations varied by pipeline at the genus level, but were conserved at the family and higher levels of classification. Significance testing was done by the Mann Whitney U test, however the second data set was corrected for false discovery rate. This more stringent analysis explains why fewer taxa are revealed as significant changes.

Statistical Analysis.

All biochemical data are expressed as Scatter plots with means. Differences between dietary groups were evaluated using Mann-Whitney U test. Significance was corrected for false discovery (Benjamini et al., Journal of the Royal Statistical Society. Series B (Methodological), 289-300, 1995).

Bioinformatic Analysis.

The Qiime pipeline29 was used to further process the sequences and produce the operational taxonomic unit (OTU) absolute abundance table and weighted UniFrac beta-diversity matrix 30,31. Principle component analysis (PCA) plots were produced based on weighted UniFrac distances. The rarefactions for richness and Shannon diversity indices were calculated in R statistical programming environment 32,33 using Community Ecology Package vegan. Comparison of weighted UniFrac distances was performed using two-sided t-test. The OTU absolute abundances were converted to relative abundances by normalizing to total sequence count per sample analyzed. The resulting relative abundance matrix was used to produce heatmaps for major (relative abundance >1%) taxa.

Results

All C57BL/6J mice were fed a high fat diet (HFD, 60% kcal from fat) for 2 weeks prior to the study and then randomized to continue the HFD, to receive the HFD supplemented with HPMC (HPMC diet), or to receive a low fat diet (LFD, 10% kcal from fat). Over the course of the 4-week study, the mice on the HFD continued to gain weight, while HPMC supplementation reduced weight gain (FIG. 1*a*), despite isocaloric food intake (FIG. 1*b*). Mice receiving the LFD had significantly lower energy intake and lost weight (FIGS. 1*a-b*). Weight change and energy intake were correlated in both the individual HFD and LFD mice (R=0.84 and 0.65, p=0.003 and 0.042, respectively); when combined, the correlation strengthened (R=0.98) (FIG. 1*c*). Based on this best-fit line, the actual weight of the HPMC mice was 4.7 g±2.2 lower than predicted (FIG. 1*d*), with no significant correlation with energy intake. Thus, the HPMC diet disrupted the energy intake/weight gain relationships observed for the two other dietary groups.

After 4 weeks, mice on the LFD and HPMC diets had significantly reduced total cholesterol, HDL, LDL, and VLDL, compared to the HFD mice (FIGS. 2*a-d*). The LFD mice also had decreased fasting blood glucose, and free-fatty acids (FIGS. 2*e, g*). Leptin levels were decreased in both the LFD and HPMC mice, consistent with the lowered weights (FIG. 2*i*), as were liver triglycerides (FIG. 2*l*). Insulin was decreased in HPMC mice (FIG. 2*h*). Compared to both the LFD and HFD mice, HPMC supplementation increased fecal fat excretion, including saturated, unsaturated, and trans-unsaturated fats, and bile acids, but decreased sterol excretion (FIGS. 2*m-q*). HPMC increased fecal excretion of mono- but not di- or triacylglycerides (FIGS. 2*r-t*). Thus, in the setting of a high-fat, high-calorie diet, HPMC improved metabolic biomarkers to an extent similar to that of the LFD, but with increased fecal loss of specific metabolites.

Microbial Population Sizes.

Figure 7:
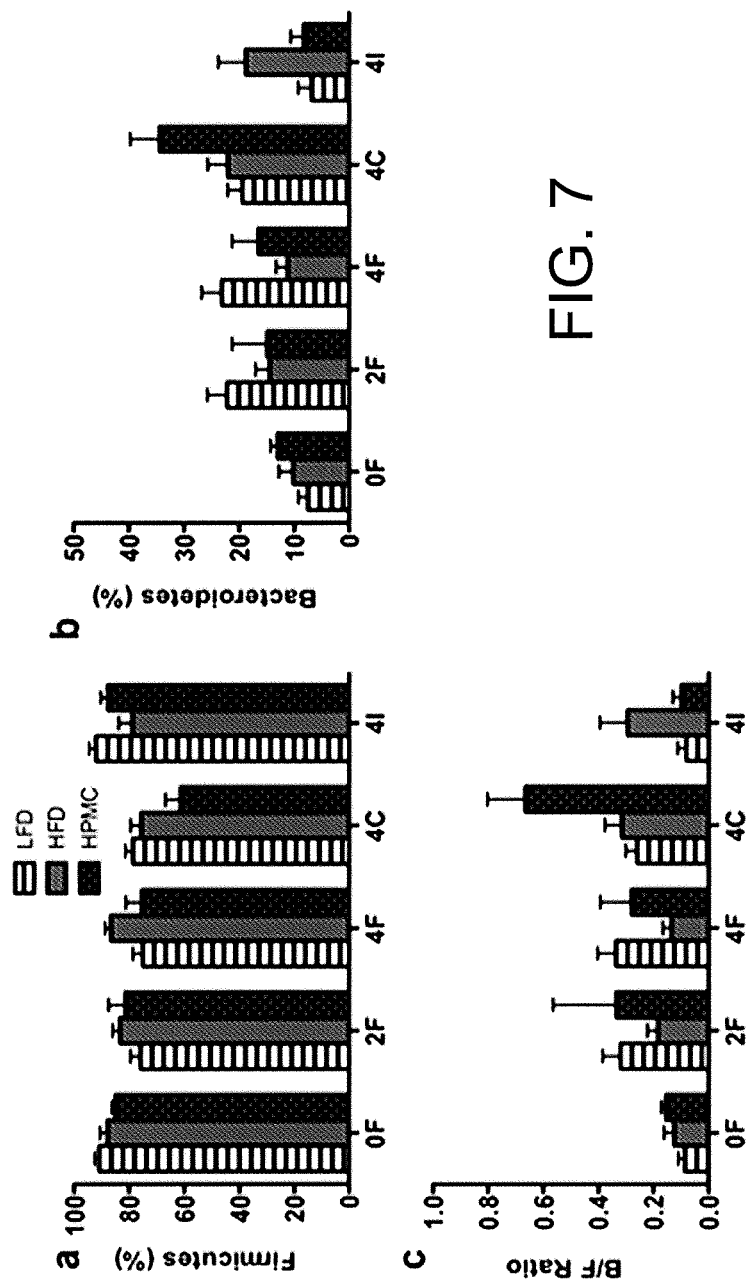
FIGS. 7a-7c are graphs showing the relative abundance (%) of 454-pyrosequencing reads classified at the phylum level for a) Firmicutes, b) Bacteroidetes, and c) the ratio of Bacteroidetes to Firmicutes.
Figure 8:
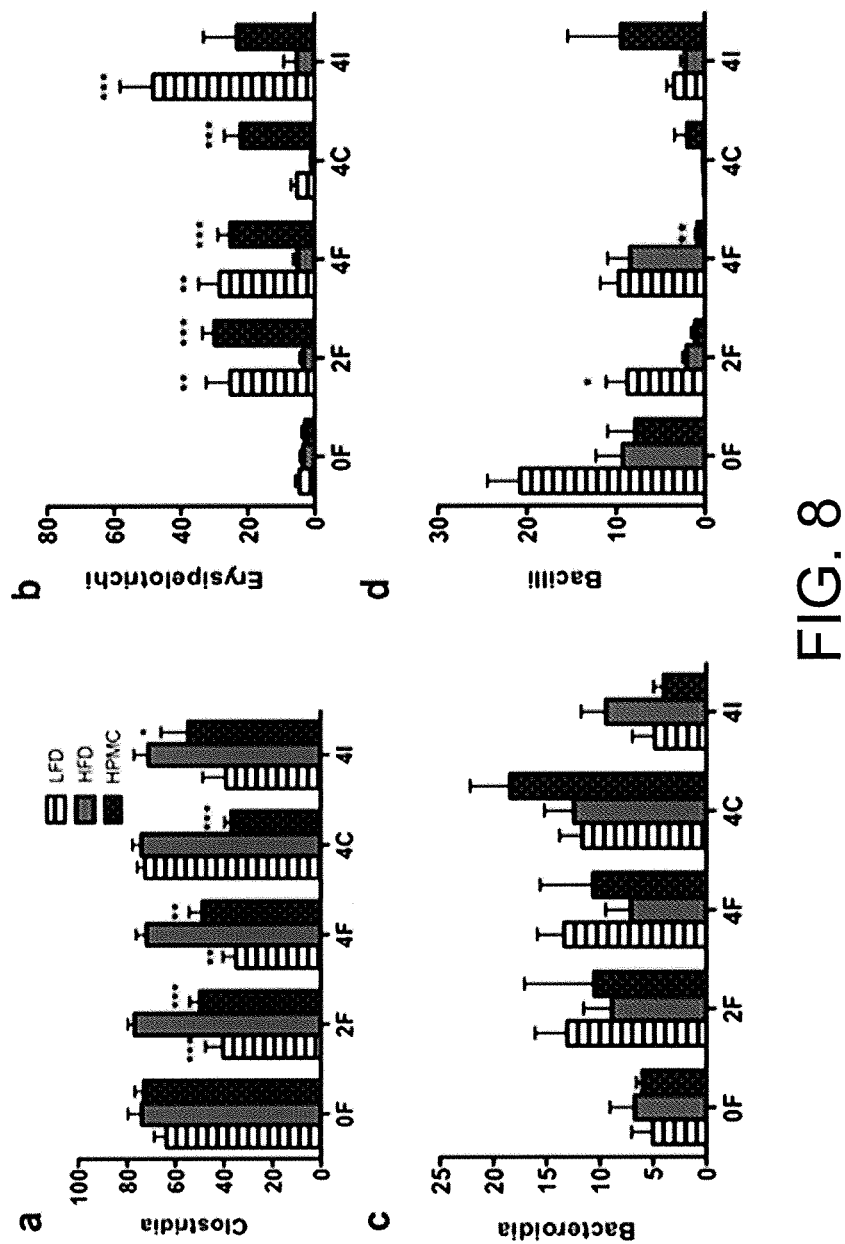
FIGS. 8a-8d are graphs showing the relative abundance (%) of 454-pyrosequencing reads classified at the class level for a) Clostridia, b) Erysipelotrichi, c) Bacteroidia, and d) Bacilli. *P<0.05, P<0.01, *P<0.001 for FDR-corrected Mann-Whitney-U.
Figure 9:
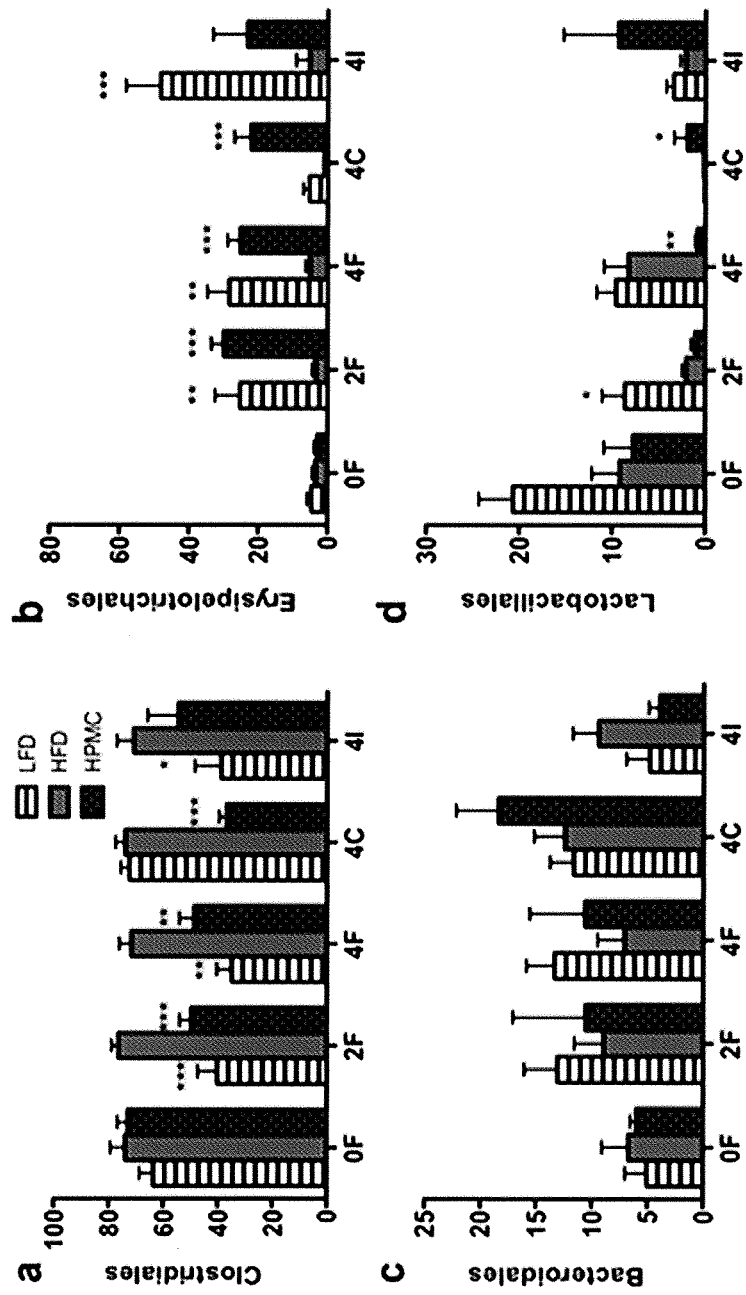
FIGS. 9a-9d are graphs showing the relative abundance (%) of 454-pyrosequencing reads classified at the order level for a) Clostridiales, b) Erysipelotrichales, c) Bacteroidales, and d) Lactobacillales, ***P<0.001 for FDR-corrected Mann-Whitney-U.

To assess quantitative changes in microbial populations, total bacteria were enumerated and the two predominant phyla: Bacteroidetes and Firmicutes, using quantitative PCR of 16S rRNA genes. At baseline, as expected, there were no significant differences in total fecal bacteria or B/F ratio between the mice about to be randomized into the three treatment groups (FIG. 7). Total bacteria levels were significantly decreased in fecal, cecal, and ileal samples from HPMC mice compared to the two other groups. The Bacteroidetes/Firmicutes (B/F) ratio in fecal samples was unchanged as expected in the HFD mice, but increased in LFD and HPMC mice and in cecal samples from HPMC mice. In contrast, in ileal samples, the B/F ratios were decreased in LFD and HPMC mice (FIG. 7*c*). These data indicate that the dietary changes, especially adding HPMC, affected the size and composition of the intestinal microbiota.

Microbial Community Composition.

Figure 14A:
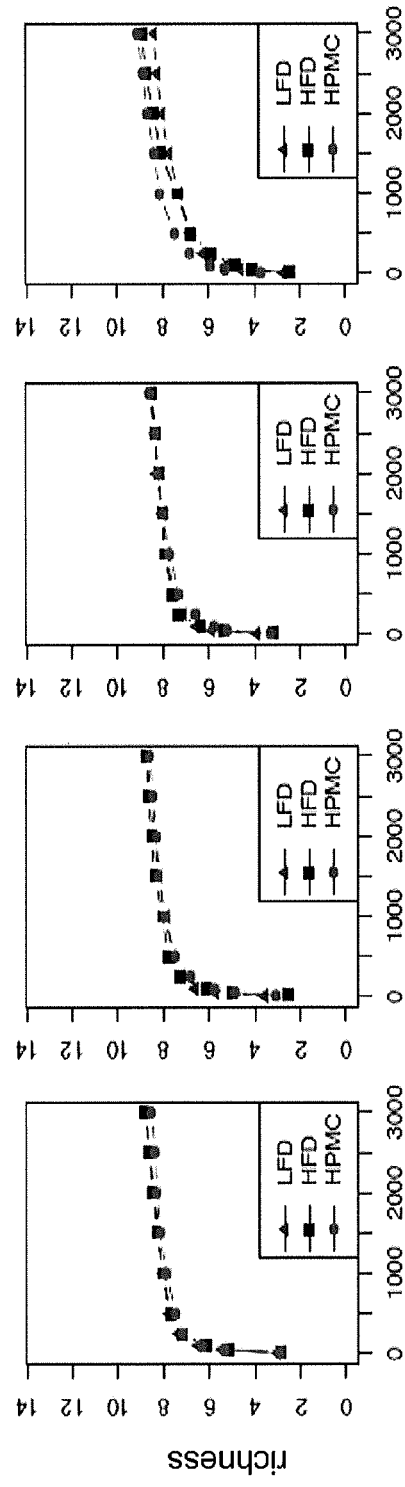
FIGS. 14a and 14b are graphs showing diversity of the bacterial populations in the fecal and cecal microbiota at the class level. Rarefaction curves for class richness and Shannon diversity index for evenness are shown at the class level.
Figure 14B:
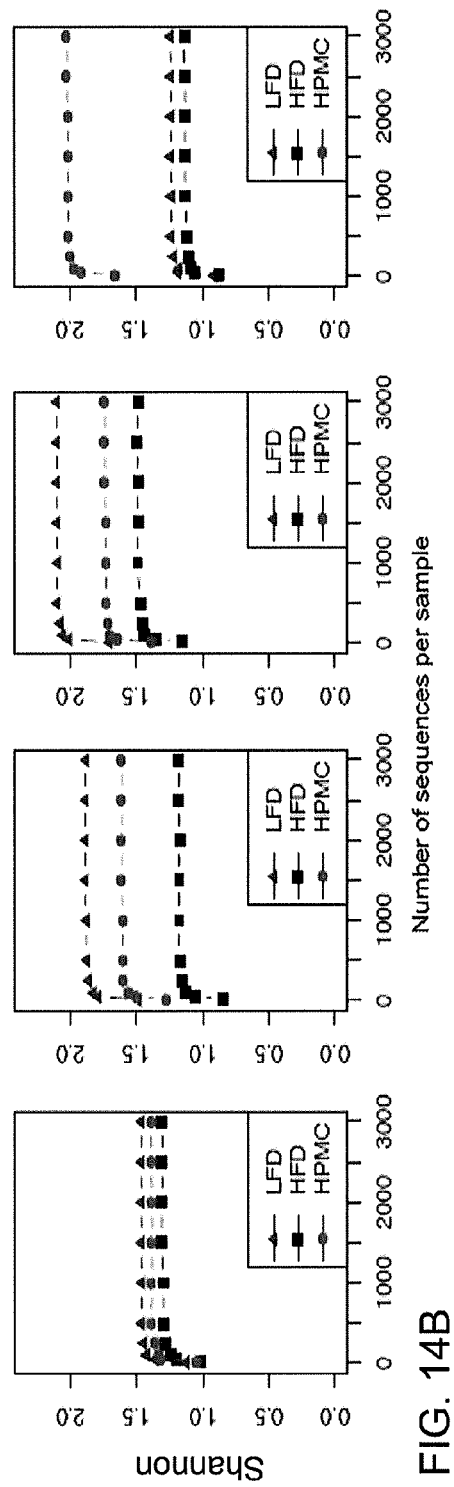
Figures 15A, 15B:
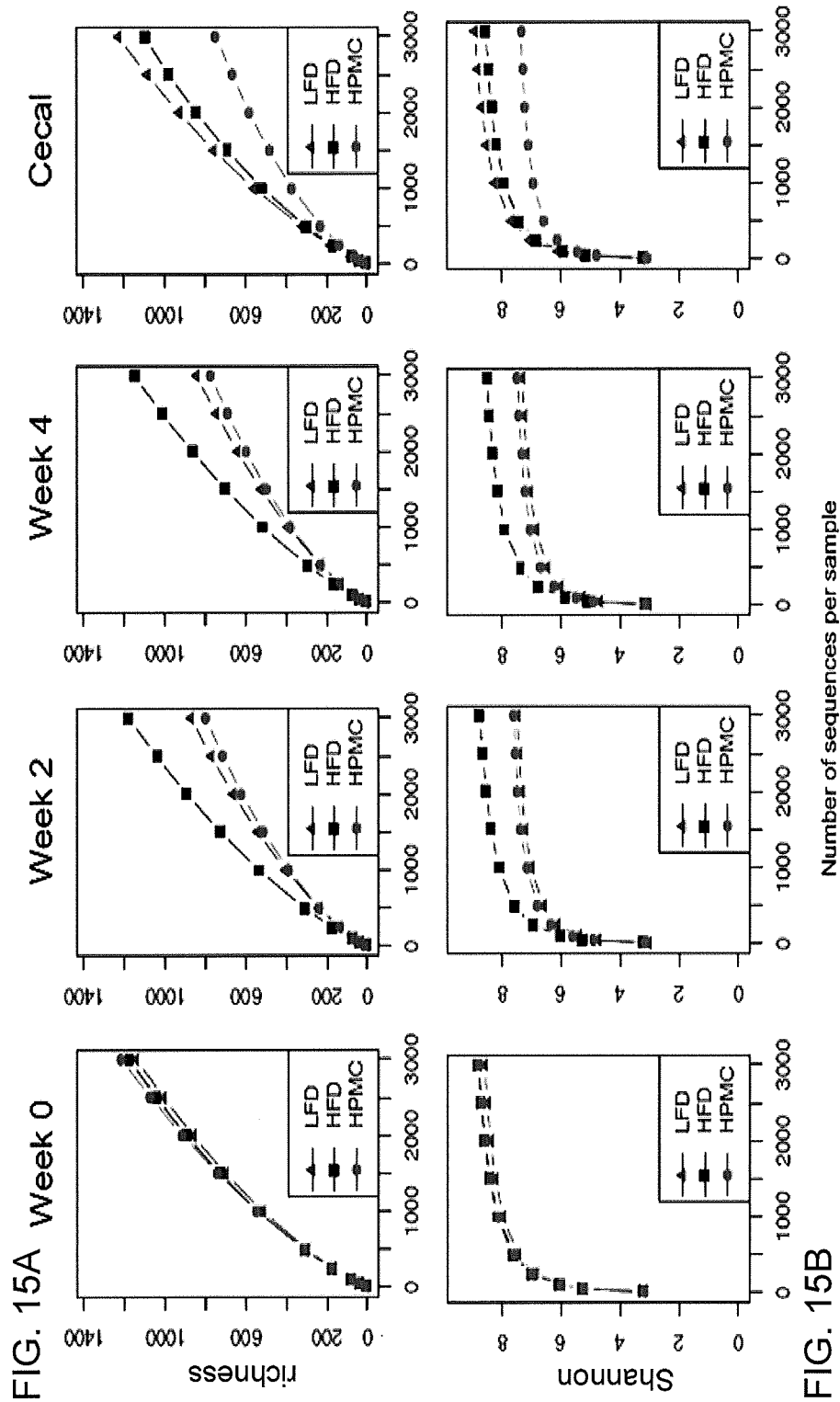
FIGS. 15a and 15b demonstrate assessment of microbial diversity in relation to treatments. Top. Rarefaction curves at the OTU level for a) taxonomic richness and b) Shannon index for evenness of the intestinal microbiome in fecal (week 0, 2, and 4) and cecal (week 4) microbiota, according to dietary treatment.

To assess changes in murine intestinal microbial community structure induced by the dietary changes, measures of richness and diversity were calculated for microbial 16S rDNA V3-V5 sequences in fecal and cecal samples. At the class level, richness in the fecal and cecal communities from the three groups were similar (FIG. 14*a*), but at the OTU level, the LFD and HPMC mice had decreased fecal community richness compared to HFD, and the HPMC mice had reduced richness in cecal samples as well (FIG. 15*a*). Thus, although population structure was conserved at the higher (class) taxonomic level, the dietary changes diminished diversity at the more specific (OTU) taxonomic level. Evenness at the class level as measured by Shannon score, increased in the LFD and HPMC mouse fecal samples, and in cecal samples for HPMC mice (FIG. 14*b*), but decreased in the same groups at the OTU level (FIG. 15b). These findings suggest that the dietary interventions favored a relatively small number of specialist organisms within larger taxonomic units that became more balanced.

Figures 17A, 17B:
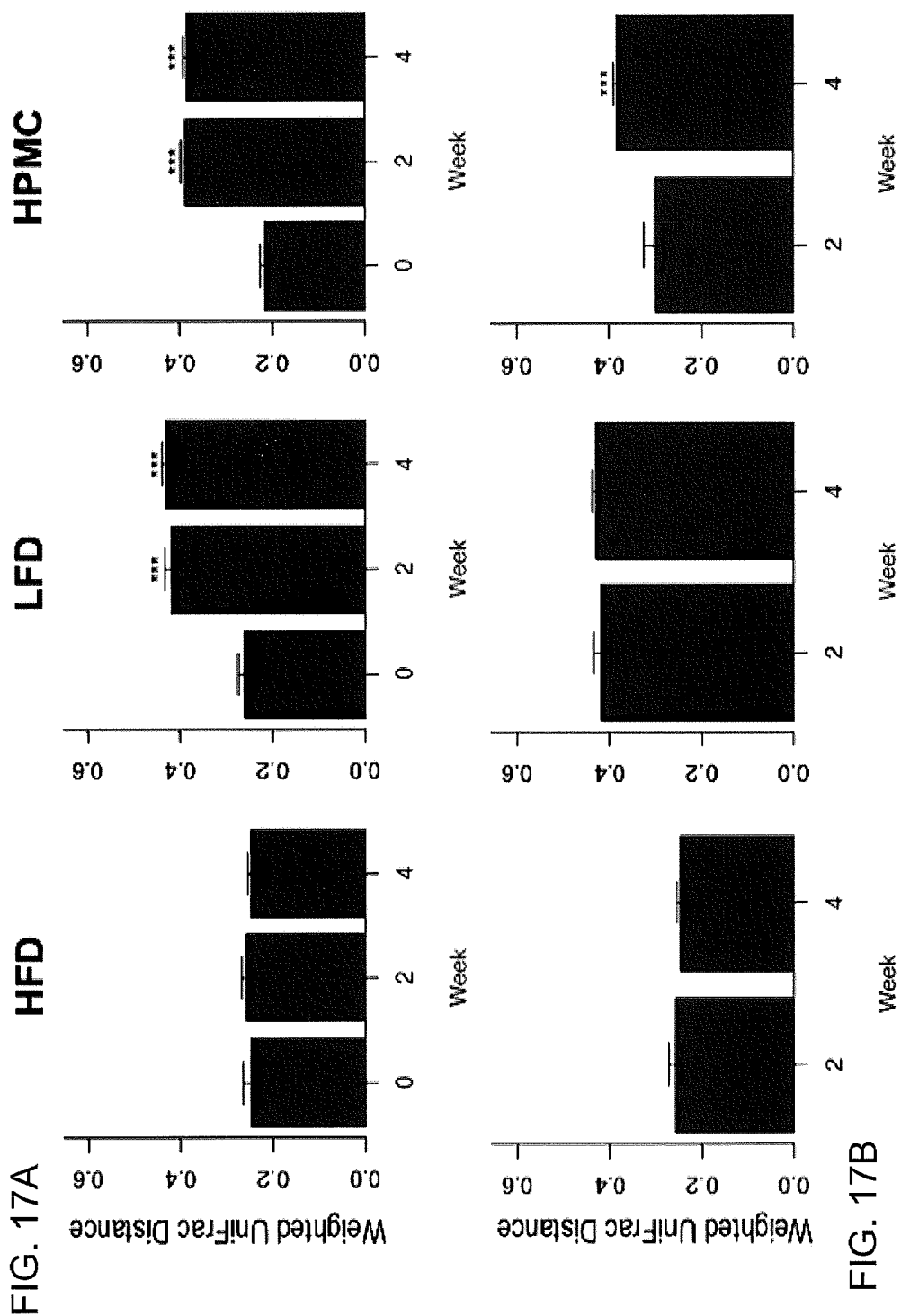
FIGS. 17a and 17b show weighted UniFrac distance of the fecal microbiome at the OTU level. Distance (mean±95% CI) are shown from baseline (panel a), or from week 2 (panel b). *** p<0.001. As with unweighted UniFrac distances, there were no differences for the HFD mice over the course of the experiment, as expected. In the HPMC mice, there were progressive difference in the community structure at weeks 2 and 4, whereas for the LFD mice, the communities stabilized after week 2.

The phylogenetic differences between the three treatment groups also were assessed by principal component analysis (PCA) based on unweighted Unifrac values (FIG. 16). At week 0 (baseline), all samples cluster together (panel a), while at week 2 (panel b) and week 4 (panel c), the HFD samples were little different from baseline, whereas the LFD and HPMC communities had shifted in separate directions forming distinct clusters (panels d,e). There was no significant change in pairwise UniFrac distances over time for any of the HFD fecal samples. For the LFD samples, pairwise distances increased from weeks 0 to 2, but not from 2 to 4. For the HPMC fecal samples, pairwise distances increased from weeks 0 to 2, and from 2 to 4. Analysis of the weighted UniFrac distances showed similar trends (FIG. 17). The PCA of the cecal specimens obtained at sacrifice is similar to the week 4 fecal specimens, but the LFD and HFD samples are well-mixed, with HPMC forming a distinct cluster (panel f). The ileal specimens at sacrifice show no distinctive clustering by treatment group (panel g). In total, the data indicate stability of the microbial community structure in the mice continued on HFD, as expected, whereas there was an early and persisting shift for the mice given the LFD, and progressive changes for the microbiota of the mice given HPMC.

Population Changes Induced by Dietary Intervention.

Hierarchical clustering by heat map analysis (FIG. 18) for the most abundant taxons (>1%) at the family level in cecal specimens showed clear separation ($p<0.001$) of the HPMC samples from the HFD and LFD, which were not distinguishable (subpanel a). The fecal samples at week 0 (baseline) were well-mixed between the three groups, as expected, (subpanel b), but composition gradually (subpanels c,d) moved toward three clusters, with each treatment group individuating.

To assess specific changes in intestinal microbiota, the raw pyrosequencing counts were converted to relative abundance, and false discovery rate (FDR)-corrected pair-wise comparisons for each predominant (≥1%) taxon from the phylum through genus level were made for HFD vs LFD (to assess for the effects of fat % dietary change) and HFD vs. HPMC (to assess for the effects of fiber addition) (Table 2). No significant differences were seen in week 0 fecal samples, as expected, since at baseline all mice were receiving the same (HFD) diet. Over the course of the experiment, there were no significant differences at the phylum level. All differences at lower taxonomic levels were within the phylum Firmicutes, involving members of class Bacilli, Clostridia, and Erysipelotrichi (and order Lactobacillates, Clostridiates, and Erysipelotrichales).

Figure 10:
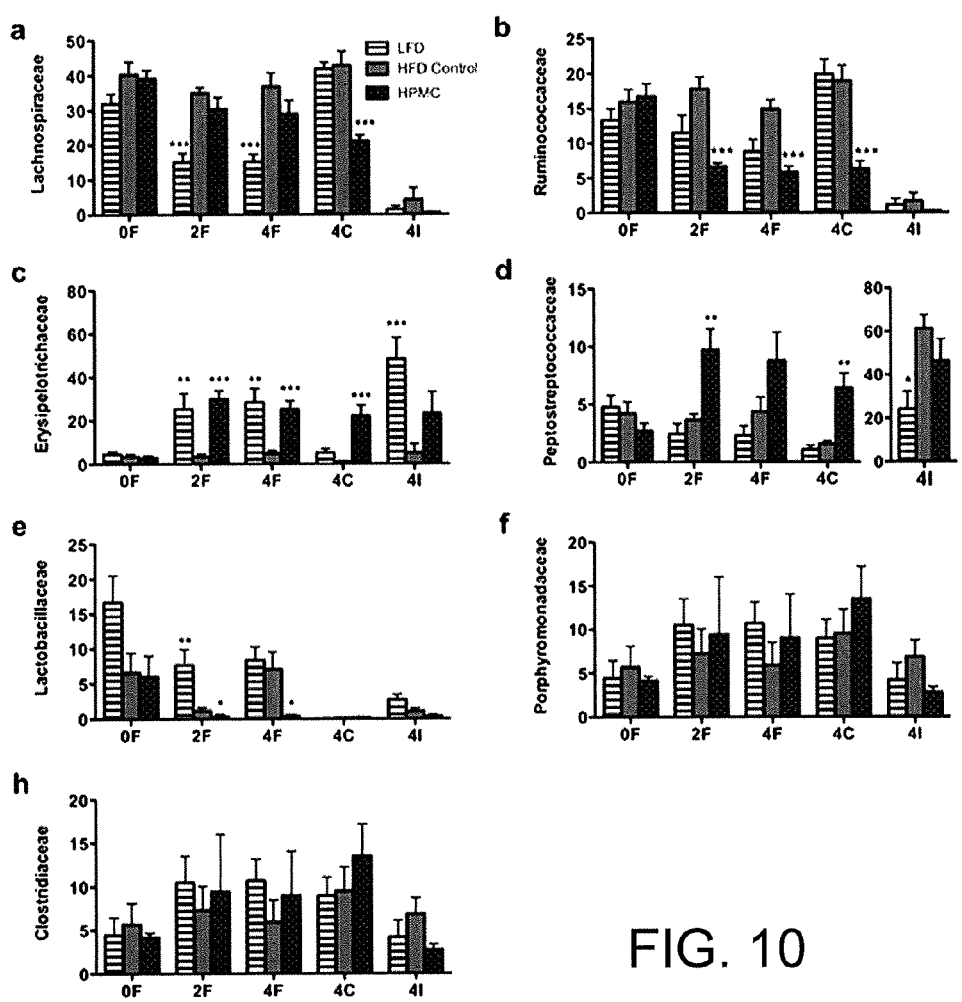
FIGS. 10a-10h are graphs showing the relative abundance (%) of 454-pyrosequencing reads classified at the family level for a) Lachnospiraceae, b) Ruminococcaceae, c) Erysipelotrichaeceae, d) Peptostreptococcaceae, e) Lactobacillaceae, f) Porphyromonadaceae, h) Clostridiaceae. ***P<0.001 for FDR-corrected Mann-Whitney-U.
Figure 11:
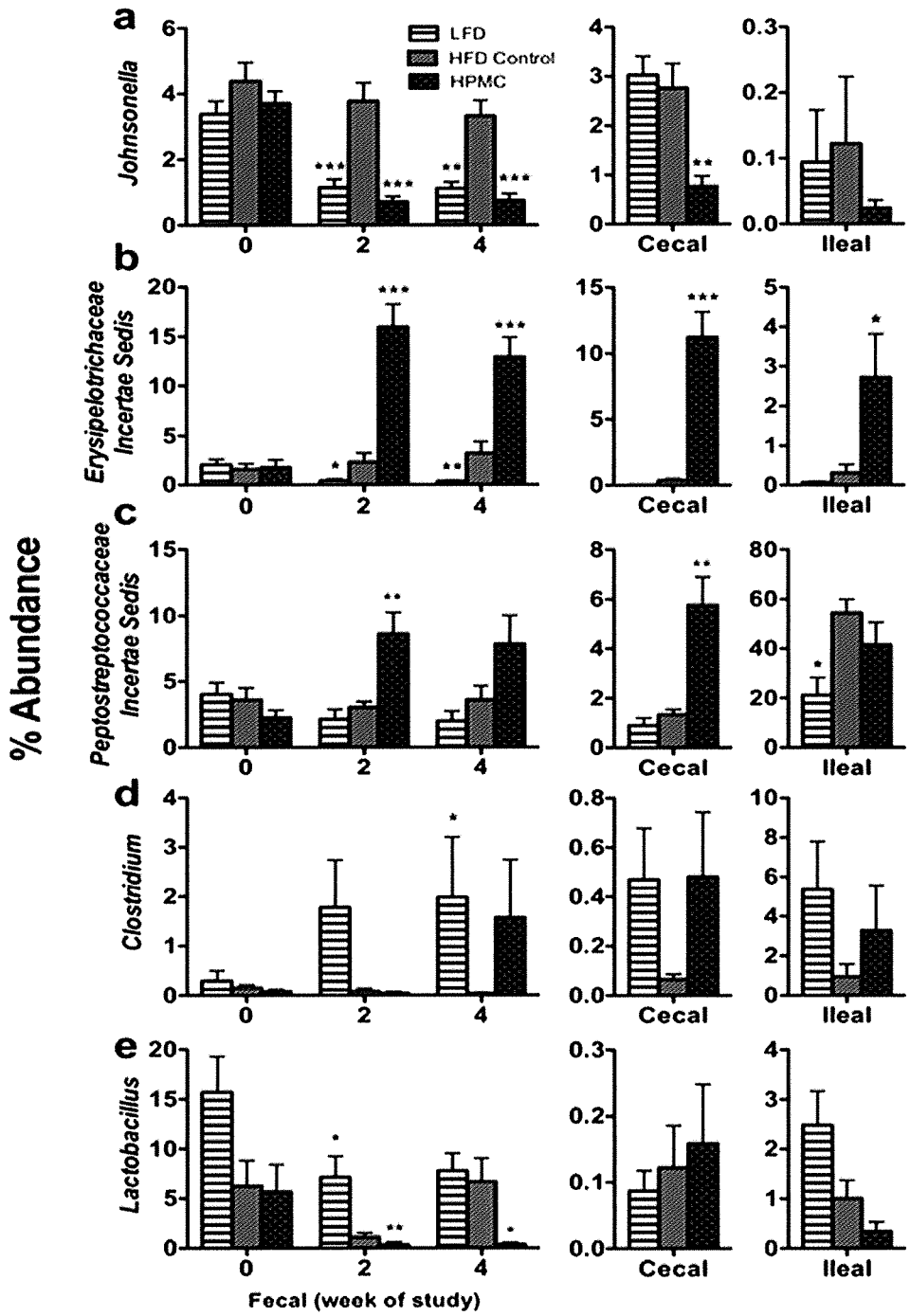
FIGS. 11a-11e are graphs showing the relative abundance (%) of 454-pyrosequencing reads classified at the genus level for a) *Johnsonella*, b) Erysipelotrichaceae incertae sedis, c) Peptostreptococcaceae incertae sedis, d) *Clostridium*, e) *Lactobacillus*.***P<0.001 for FDR-corrected Mann-Whitney-U.

At the family level, there were seven predominant taxa (FIG. 10. Lachnospiraceae populations in LFD and HPMC mice became decreased (FIG. 10a) and Ruminococcaceae levels became reduced in HPMC mice (FIG. 10b), while Erysipelotrichaceae levels increased in both LFD and HPMC treated mice (FIG. 10c), and Peptostreptococcaceae levels were consistently increased in HPMC mice (FIG. 10d). Differences in cecal and ileal populations were limited to HPMC and LFD mice, respectively. At the genus level, there also were significant changes in community structure (FIG. 11).

The HPMC treatment led to significant decreases in *Jonsonella* and *Lactobacillus*, and significant increases in Erysipelotrichaceae Insertae Sedis and Peptostreptococcus Insertae Sedis. Thus, the dietary changes selected for different compositions within Firmicutes, with reproducible compositional effects at the family level.

TABLE 2

Composition of the three experimental diets

| Component | Low-Fat gm % | Low-Fat kcal % | High-Fat gm % | High-Fat kcal % | High-Fat/10% HPMC gm % | High-Fat/10% HPMC kcal % |
|---|---|---|---|---|---|---|
| Protein | 19.2 | 20 | 26.2 | 20 | 23.6 | 20 |
| Carbohydrate | 67.3 | 70 | 26.3 | 20 | 23.6 | 20 |
| Fat | 4.3 | 10 | 34.9 | 60 | 31.3 | 60 |
| Total | | 100 | | 100 | | 100 |
| kcal/gm | 3.85 | | 5.24 | | 4.71 | |

| Ingredient | gm | kcal | gm | kcal | gm | kcal |
|---|---|---|---|---|---|---|
| Casein, 80 Mesh | 200 | 800 | 200 | 800 | 200 | 800 |
| L-Cystine | 3 | 12 | 3 | 12 | 3 | 12 |
| Corn starch | 315 | 1260 | 0 | 0 | 0 | 0 |
| Maltodextrin 10 | 35 | 140 | 125 | 500 | 125 | 500 |
| Sucrose | 350 | 1400 | 68.8 | 275.2 | 68.8 | 275.2 |
| Cellulose, BW200 | 50 | 0 | 50 | 0 | 50 | 0 |
| Soybean Oil | 25 | 225 | 25 | 225 | 25 | 225 |
| Lard | 20 | 180 | 245 | 2205 | 245 | 2205 |
| Mineral Mix S10026 | 10 | 0 | 10 | 0 | 10 | 0 |
| Dicalcium Phosphate | 13 | 0 | 13 | 0 | 13 | 0 |
| Calcium Carbonate | 5.5 | 0 | 5.5 | 0 | 5.5 | 0 |
| Potassium Citrate, 1 H2O | 16.5 | 0 | 16.5 | 0 | 16.5 | 0 |
| Vitamin Mix V10001 | 10 | 40 | 10 | 40 | 10 | 40 |
| Choline Bitartrate | 2 | 0 | 2 | 0 | 2 | 0 |
| HPMC[a] | 0 | 0 | 0 | 0 | 88 | 0 |
| FD&C Yellow Dye #5 | 0.05 | 0 | 0 | 0 | 0.025 | 0 |
| FD&C Blue Dye #1 | 0 | 0 | 0.05 | 0 | 0.025 | 0 |

[a]HPMC, hydroxyl-methyl cellulose (K250M)

Correlation Network Analysis.

Figure 20:
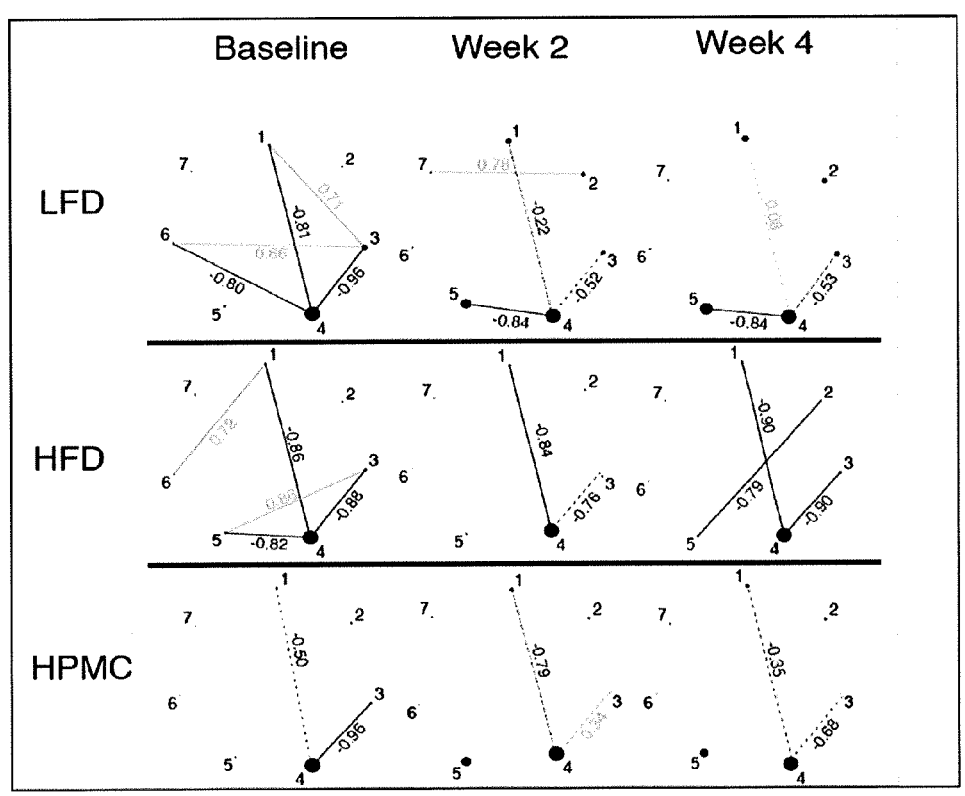
FIG. 20 shows associations between predominant taxa in fecal specimens. Specimens were obtained at baseline (week 0) and at weeks 2 and 4 from the three experimental groups of mice (LFD, HFD, and HPMC). A circle indicates that Order level taxon is present at ≥1% in all specimens and the circle size corresponds to relative abundance. Taxa classified at the Order level are: 1, Bacteroidales; 2, Bacteroidetes: unclassified; 3, Lactobacillales; 4, Clostridiales; 5, Erysipelotrichales; 6, Firmicutes: unclassified; 7, Bacteria: unclassified. A solid line indicates a significant (p<0.05) correlation between two Orders, whereas a dashed line is not significant (p>0.05). The numerical values indicate the strength of the correlation and the directionality (positive or negative).

To understand the dynamic relationships between intestinal microbiota under differing dietary conditions, a correlation network was constructed at the order level (FIG. 20). At baseline (week 0), Clostridiales significantly negatively correlated with Lactobacillales in all three groups of mice and with Bacteroidales in two of the three groups. The negative correlations between these three taxa persisted in the HFD mice over the 4-week study. However, both dietary interventions (LFD and HPMC) eliminated the stable link between Bacteroidales-Clostridiales-Lactobacillales. LFD mice showed a stable negative correlation between Clostridiales and Erysipelotrichales, whereas no significant correlations emerged in the HPMC mice. Thus, the major bacterial networks established under HFD conditions were not conserved after dietary change.

Conditional Correlation Analysis.

The results show that HPMC or LFD treatments altered both host metabolism and intestinal microbiota. To detect individual taxa that may be responsible for metabolic effects, conditional correlation analysis was performed, to remove the effect of the treatment condition (either presence of fiber or fat percent) from the two linked variables: host phenotype and taxa. Significant FDR-corrected p-values for each pairwise comparison of taxa in particular samples with each metabolic variable are indicated (Tables 3-4) and regression analysis was used to avoid reporting correlations influenced by outlier samples (FIG. 21. Weight change in HFD mice was positively correlated with cecal Firmicutes and cecal Erysipelotrichaceae *Insectae Sedis* (I.S.) and negatively associated with cecal Bacteroidetes (panels a-c). For the HPMC mice, weight changes and fecal saturated fat were positively associated with cecal Erysipelotrichaceae I.S, and cecal Erisipelotrichales, respectively (c, f). Four-week fecal abundances of Lachnospiraceae negatively correlated with energy intake in the HFD and HPMC mice (panel d and FIG. 23) and cecal Porphyromonadaceae correlated positively with liver free cholesterol in HFD and HPMC mice (panel e). In total, there were no significant correlations between taxa and host metabolic phenotype for the LFD group, however, the HPMC treatment-induced host phenotypes correlated with altered representation of particular taxa.

TABLE 3

Significant differences in relative abundance in HFD vs. HPMC mice (effect of fiber in diet) and HFD vs LFD mice (effect of fat % in diet) for all taxa >1% classified at levels from phylum to genus.

| | Effect of Fiber in Diet | | | | | Effect of Fat % in Diet | | | | |
|---|---|---|---|---|---|---|---|---|---|---|
| Phylum | 0 F fiber | 2 F fiber | 4 F fiber | 4 C fiber | 4 I fiber | 0 F diet | 2 F diet | 4 F diet | 4 C diet | 4 I diet |
| *Bacteroidetes* | 0.2482 | 0.5787 | 0.6842 | 0.1183 | 0.4114 | 0.6842 | 0.1338 | 0.0532 | 0.5490 | 0.0786 |
| *Firmicutes* | 0.2482 | 0.5787 | 0.6527 | 0.1183 | 0.4114 | 0.6842 | 0.1338 | 0.0532 | 0.5490 | 0.0786 |
| Other | 0.3527 | 0.5787 | 0.6842 | 0.5490 | 0.8968 | 0.1573 | 0.8534 | 0.3527 | 0.3999 | 0.2475 |
| Class | | | | | | | | | | |
| *Bacteroidia* | 0.8229 | 0.4938 | 0.4410 | 0.4156 | 0.2846 | 0.7959 | 0.1670 | 0.0917 | 0.8421 | 0.1054 |
| *Bacteroidetes*; Other | 0.0625 | 0.5085 | 0.6752 | 0.2190 | 0.4800 | 0.7356 | 0.1670 | 0.0917 | 0.8421 | 0.0621 |
| *Bacilli* | 0.8534 | 0.0621 | 0.0091 | 0.0514 | 0.5364 | 0.1298 | 0.0156 | 0.5288 | 0.8421 | 0.3930 |
| *Clostridia* | 0.8534 | 0.0002 | 0.0091 | 0.0001 | 0.5364 | 0.1470 | 0.0003 | 0.0023 | 0.8421 | 0.0343 |
| *Erysipelotrichi* | 0.8534 | 0.0002 | 0.0003 | 0.0001 | 0.2400 | 0.7356 | 0.0049 | 0.0037 | 0.3110 | 0.0005 |
| *Firmicutes*; Other | 0.8534 | 0.0067 | 0.0091 | 0.2190 | 0.2846 | 0.1561 | 0.0049 | 0.2004 | 0.3110 | 0.0002 |
| Other | 0.8229 | 0.5787 | 0.6842 | 0.5490 | 0.8968 | 0.1470 | 0.8534 | 0.4115 | 0.3110 | 0.2887 |
| Order | | | | | | | | | | |
| *Bacteroidales* | 0.8229 | 0.4938 | 0.4410 | 0.4156 | 0.2846 | 0.7959 | 0.1670 | 0.0917 | 0.8421 | 0.1054 |
| *Bacteroidetes*; Other | 0.0625 | 0.5085 | 0.6752 | 0.2190 | 0.4800 | 0.7356 | 0.1670 | 0.0917 | 0.8421 | 0.0621 |
| *Lactobacillales* | 0.8534 | 0.0621 | 0.0091 | 0.0402 | 0.5364 | 0.1298 | 0.0166 | 0.5288 | 0.8421 | 0.3930 |
| *Clostridiales* | 0.8534 | 0.0002 | 0.0091 | 0.0001 | 0.5364 | 0.1561 | 0.0003 | 0.0023 | 0.8421 | 0.0343 |
| *Erysipelotrichales* | 0.8534 | 0.0002 | 0.0003 | 0.0001 | 0.2400 | 0.7356 | 0.0049 | 0.0037 | 0.3110 | 0.0005 |
| *Firmicutes*; Other | 0.8534 | 0.0067 | 0.0091 | 0.2190 | 0.2846 | 0.1561 | 0.0049 | 0.2004 | 0.3110 | 0.0002 |
| Other | 0.8229 | 0.5787 | 0.6842 | 0.5490 | 0.8968 | 0.1561 | 0.8534 | 0.4115 | 0.3110 | 0.2887 |
| Family | | | | | | | | | | |
| *Bacteroidales*; Other | 0.1394 | 0.4702 | 0.5632 | 0.2735 | 0.5517 | 0.3972 | 0.1986 | 0.0672 | 1.0000 | 0.0697 |
| *Porphyromonadaceae* | 0.8717 | 0.4717 | 0.2855 | 0.5366 | 0.2928 | 0.9705 | 0.1802 | 0.0672 | 1.0000 | 0.2460 |
| *Bacteroidetes*; Other | 0.1072 | 0.4755 | 0.6314 | 0.2666 | 0.3657 | 0.8407 | 0.1909 | 0.0672 | 1.0000 | 0.0851 |
| *Lactobacillaceae* | 1.0000 | 0.0103 | 0.0174 | 0.8368 | 0.2963 | 0.2676 | 0.0086 | 0.5288 | 1.0000 | 0.2699 |
| *Clostridiaceae* | 0.8717 | 0.2701 | 0.5632 | 0.8368 | 0.6817 | 0.9271 | 0.1802 | 0.0672 | 0.3199 | 0.6305 |
| *Lachnospiraceae* | 1.0000 | 0.2454 | 0.2837 | 0.0005 | 0.2963 | 0.2676 | 0.0001 | 0.0008 | 1.0000 | 0.2699 |
| *Clostridiales*; Other | 1.0000 | 0.0001 | 0.0001 | 0.0001 | 0.0104 | 0.8872 | 0.0093 | 0.0003 | 0.3199 | 0.2699 |
| *Peptostreptococcaceae* | 0.8717 | 0.0003 | 0.1784 | 0.0023 | 0.3657 | 0.8407 | 0.2373 | 0.1402 | 0.3646 | 0.0155 |
| *Ruminococcaceae* | 1.0000 | 0.0005 | 0.0002 | 0.0003 | 0.2736 | 0.5597 | 0.1845 | 0.0556 | 1.0000 | 0.2699 |
| *Erysipelotrichaceae* | 1.0000 | 0.0003 | 0.0002 | 0.0001 | 0.2057 | 0.8407 | 0.0084 | 0.0042 | 0.3199 | 0.0008 |
| *Firmicutes*; Other | 1.0000 | 0.0069 | 0.0117 | 0.2681 | 0.2928 | 0.2676 | 0.0084 | 0.1718 | 0.3199 | 0.0003 |
| Other | 0.8717 | 0.5787 | 0.6842 | 0.6588 | 0.8968 | 0.2676 | 0.8534 | 0.3847 | 0.3199 | 0.2699 |
| Genus | | | | | | | | | | |
| *Bacteroidales*; Other | 0.1742 | 0.4535 | 0.5866 | 0.2486 | 0.5747 | 0.4965 | 0.1910 | 0.0672 | 1.0000 | 0.0871 |
| *Porphyromonadaceae*; Other | 0.8173 | 0.4535 | 0.3263 | 0.3469 | 0.3050 | 0.9118 | 0.1845 | 0.0672 | 1.0000 | 0.3075 |
| *Bacteroidetes*; Other | 0.1340 | 0.4670 | 0.6678 | 0.2222 | 0.3740 | 0.8531 | 0.1910 | 0.0672 | 1.0000 | 0.1064 |
| *Lactobacillus* | 0.9705 | 0.0097 | 0.0297 | 0.8683 | 0.3240 | 0.3345 | 0.0108 | 0.4961 | 1.0000 | 0.3093 |
| *Clostridiaceae 1* | 0.8173 | 0.2701 | 0.5866 | 0.8683 | 0.7210 | 0.9106 | 0.1845 | 0.0672 | 0.3910 | 0.6842 |
| *Johnsonella* | 0.8173 | 0.0001 | 0.0005 | 0.0089 | 0.7290 | 0.5439 | 0.0010 | 0.0016 | 1.0000 | 0.4343 |
| *Lachnospiraceae*; Other | 0.9705 | 0.4535 | 0.3263 | 0.0008 | 0.3240 | 0.3345 | 0.0002 | 0.0015 | 1.0000 | 0.3093 |
| *Clostridiales*; Other | 0.9705 | 0.0001 | 0.0002 | 0.0002 | 0.0130 | 0.8531 | 0.0117 | 0.0003 | 0.3910 | 0.3093 |
| *Peptostreptococcaceae*; Other | 0.9705 | 0.0245 | 1.0000 | 0.0323 | 0.3385 | 0.7265 | 0.1350 | 0.0672 | 0.7503 | 0.0575 |
| *Peptostreptococcaceae I.S.* | 0.8173 | 0.0026 | 0.1411 | 0.0016 | 0.3740 | 0.8531 | 0.1990 | 0.1514 | 0.3910 | 0.0291 |
| *Ruminococcaceae*; Other | 0.9705 | 0.0004 | 0.0003 | 0.0004 | 0.1376 | 0.7265 | 0.1845 | 0.0556 | 1.0000 | 0.3093 |
| *Erysipelotrichaceae I.S.* | 0.9705 | 0.0002 | 0.0010 | 0.0002 | 0.0154 | 0.8531 | 0.0171 | 0.0056 | 0.0540 | 0.3324 |
| *Erysipelotrichaceae*;Other | 0.8173 | 0.0001 | 0.0006 | 0.0008 | 0.1376 | 0.7265 | 0.1910 | 0.1216 | 0.7503 | 0.3093 |
| *Firmicutes*; Other | 0.9705 | 0.0062 | 0.0097 | 0.2346 | 0.3050 | 0.3345 | 0.0104 | 0.1652 | 0.3910 | 0.0003 |
| Other | 0.8173 | 0.5787 | 0.7331 | 0.6334 | 0.8968 | 0.3345 | 0.8534 | 0.3779 | 0.3910 | 0.3093 |

Table 3 shows p-values calculated for false-discovery corrections from Mann Whitney U-pair comparisons of relative abundance. Sample types included week 0 fecal (baseline, 0F), week 2 fecal (2F), week 4 fecal (4F), wee 4 cecal (4C), week 4 ileal (4I). p-values <0.05 are shaded in grey.

TABLE 4

Significant correlations between taxa and phenotype, removing the condition of presence or absence of fiber in the diet.

| | | | FDR-correct p-values* | | | | | |
|---|---|---|---|---|---|---|---|---|
| Sample | Level | Taxa | Fecal fat (saturated) | Liver cholesterol (free) | LDL cholesterol | Adiponectin | Weight gain | Energy intake |
| 4W Cecal | Phylum | Bacteroidetes | 0.184 | 0.055 | 0.226 | 0.734 | 0.038 | 0.905 |
| 4W Cecal | Phylum | Firmicutes | 0.184 | 0.076 | 0.226 | 0.842 | 0.038 | 0.905 |
| 4W Cecal | Class | Bacteroidia | 0.279 | 0.005 | 0.112 | 0.735 | 0.214 | 0.977 |
| 4W Cecal | Class | Erysipelotrichi | 0.049 | 0.659 | 0.252 | 0.735 | 0.084 | 0.977 |
| 4W Ileal | Class | Bacilli | 0.744 | 0.809 | 0.346 | 0.049 | 0.703 | 0.091 |
| 4W Ileal | Class | Erysipelotrichi | 0.744 | 0.809 | 0.011 | 0.759 | 0.287 | 0.433 |
| 4W Cecal | Order | Bacteroidales | 0.279 | 0.005 | 0.112 | 0.735 | 0.214 | 0.977 |
| 4W Cecal | Order | Erysipelotrichales | 0.049 | 0.659 | 0.252 | 0.735 | 0.084 | 0.977 |
| 4W Ileal | Order | Lactobacillales | 0.744 | 0.809 | 0.346 | 0.049 | 0.703 | 0.091 |
| 4W Ileal | Order | Erysipelotrichales | 0.744 | 0.809 | 0.011 | 0.759 | 0.287 | 0.433 |
| 4W Fecal | Family | Lachnospiraceae | 0.938 | 0.927 | 0.795 | 0.715 | 0.943 | 0.017 |
| 4W Cecal | Family | Porphyromonadaceae | 0.301 | 0.009 | 0.454 | 0.881 | 0.268 | 0.837 |
| 4W Ileal | Family | Erysipelotrichaceae | 0.985 | 0.848 | 0.023 | 0.866 | 0.381 | 0.554 |
| 4W Fecal | Genus | Lachnospiraceae; Other | 0.988 | 0.966 | 0.950 | 0.670 | 0.896 | 0.018 |
| 4W Cecal | Genus | Porphyromonadaceae; Other | 0.348 | 0.023 | 0.559 | 0.893 | 0.395 | 0.891 |
| 4W Cecal | Genus | Erysipelotrichaceae Incertae Sedis | 0.257 | 0.685 | 0.559 | 0.893 | 0.002 | 0.891 |

*p-values <0.05 are shaded in grey

TABLE 5

Significant correlations between taxa and phenotype removing the condition of the percent fat in the diet.

| | | | FDR-correct p-values* | | | | | |
|---|---|---|---|---|---|---|---|---|
| Sample | Level | Taxa | Fecal triacylglycerides | Liver cholesterol (free) | Liver chloesterol (total) | Triglycerides | LDL Cholesterol | Insulin |
| 4W Ileal | Phylum | Bacteroidetes | 0.049 | 0.645 | 0.993 | 0.461 | 0.314 | 0.139 |
| 4W Ileal | Phylum | Firmicutes | 0.049 | 0.645 | 0.993 | 0.461 | 0.314 | 0.139 |
| 0W Fecal | Class | Clostridia | 0.950 | 0.142 | 0.772 | 0.199 | 0.949 | 0.049 |
| 2W Fecal | Class | Bacteroidetes; Other | 0.686 | 0.771 | 0.857 | 0.012 | 0.953 | 0.484 |
| 2W Fecal | Class | Firmicutes; Other | 0.686 | 0.493 | 0.569 | 0.663 | 0.012 | 0.827 |
| 4W Fecal | Class | Bacteroidetes; Other | 0.989 | 0.739 | 0.946 | 0.010 | 0.573 | 0.869 |
| 4W Cecal | Class | Bacteroidia | 0.821 | 0.046 | 0.879 | 0.769 | 0.858 | 0.524 |
| 0W Fecal | Order | Clostridiales | 0.950 | 0.142 | 0.775 | 0.199 | 0.966 | 0.033 |
| 2W Fecal | Order | Bacteroidetes; Other | 0.686 | 0.771 | 0.857 | 0.012 | 0.953 | 0.484 |
| 2W Fecal | Order | Firmicutes; Other | 0.686 | 0.493 | 0.635 | 0.663 | 0.012 | 0.827 |
| 4W Fecal | Order | Bacteroidetes; Other | 0.989 | 0.844 | 0.946 | 0.010 | 0.573 | 0.869 |
| 4W Cecal | Order | Bacteroidales | 0.821 | 0.046 | 0.879 | 0.769 | 0.858 | 0.524 |
| 4W Cecal | Order | Bacteroidales; Other | 0.759 | 0.762 | 0.883 | 0.011 | 0.988 | 0.461 |
| 4W Cecal | Order | Bacteroidetes; Other | 0.736 | 0.925 | 0.883 | 0.011 | 0.980 | 0.461 |
| 4W Cecal | Order | Firmicutes; Other | 0.736 | 0.635 | 0.650 | 0.764 | 0.021 | 0.827 |
| 4W Fecal | Family | Bacteroidetes; Other | 0.953 | 0.995 | 0.946 | 0.037 | 0.532 | 0.972 |
| 4W Fecal | Family | Bacteroidetes; Other | 0.989 | 0.914 | 0.946 | 0.016 | 0.532 | 0.972 |
| 4W Fecal | Family | Clostridiaceae | 0.749 | 0.494 | 0.010 | 0.805 | 0.656 | 0.972 |
| 2W Fecal | Genus | Bacteroidales; Other | 0.889 | 0.785 | 0.895 | 0.015 | 0.933 | 0.535 |
| 2W Fecal | Genus | Bacteroidetes; Other | 0.889 | 0.873 | 0.895 | 0.015 | 0.933 | 0.535 |
| 2W Fecal | Genus | Firmicutes; Other | 0.889 | 0.785 | 0.812 | 0.784 | 0.029 | 0.877 |
| 4W Fecal | Genus | Bacteroidetes; Other | 0.989 | 0.928 | 0.955 | 0.022 | 0.695 | 0.972 |
| 4W Fecal | Genus | Clostridiaceae 1 | 0.804 | 0.521 | 0.014 | 0.812 | 0.726 | 0.972 |
| 4W Fecal | Genus | Turicibacter | 0.804 | 0.521 | 0.024 | 0.131 | 0.726 | 0.866 |

*p-values <0.05 are shaded in grey

Analysis of Erysipelotrichaceae Incertae Sedis

Sequences that are categorized at the genus level within Erysipelotrichaceae incertae sedis (EIS) account for 4.5% of all microbial 16S rRNA sequences in the present study. Incertae sedis in latin means uncertain seat and notates a placeholder for a potential new genus in which defined species and sequences of uncultivated organisms are placed. A list of cultured and named species in unclassified Erysipelotrichaceae, according to NCBI taxonomy is shown below:

> *Clostridium cocleatum*
> *Clostridium innocuum*
> *Clostridium ramosum*
> *Clostridium spiraforme*
> *Eubacterium bioforme*
> *Eubacterium cylindroides*
> *Eubacterium dolichum*
> *Eubacterium tortuosum*
> *Lactobacillus catenaformis*
> *Lactobacillus vitulinus*
> *Streptococcus pleomorphus* minimum percent identity was set at 75%. There were 24 unique organisms identified as closest matches.

59 of the 109 EIS OTUs had a closest match to *Clostridium cocleatum* str. DSM 1551, accounting for 62.1% of the EIS sequences and 2.8% of the total taxonomic sequences from the 454-pyrosequencing run. *C. cocleatum* had an average sequence identity of 95.5% (±0.28% S.E., min 89.4%, max 98.6%) over an average sequence length of 367 nucleotides (±11.3 S.E, min 108, max 489). One OTU comprised 20.0% of the EIS sequences, and 0.9% of the total taxonomic sequences, and had a closest match to uranium-contaminated aquifer clone 1013-28-CG45 (UCAC), classified in RDP as Firmicutes; Clostridia; Clostridiales; Peptococcaceae; Peptococcaceae 1; Desulfosporosinus, with a sequence identity of 93.7% over a length of 270 nucleotides. All other closest matches accounted for less than 0.2% of the total taxonomic sequences, and less than 4% of the EIS sequences (Table 5). Due to the high relative abundance (FIG. 24) and high percent identity of OTUs to *Clostridium cocleatum*, this organism is a promising candidate.

TABLE 6

Identity of closest matches of OTUs classified as Erysipelotrichaceae incertae sedis (EIS) determined by sequence BLAST using GreenGenes. The first column indicates relative abundance in all 147 samples from the Diet/Fiber study and the second column is % of sequences classified as EIS.

| % of total sequences | % of Erysipelotrichaceae incertae sedis | Average BLAST percent identity to template | #OTUs | Closest Match |
|---|---|---|---|---|
| 2.77 | 62.14 | 95.5 | 59 | *Clostridium cocleatum* str. DSM 1551 |
| 0.89 | 20.00 | 93.7 | 1 | uranium-contaminated aquifer clone 1013-28-CG45 |
| 0.14 | 3.16 | 81.6 | 1 | marine bone clone boneC3C9 |
| 0.12 | 2.68 | 86.3 | 5 | human fecal clone RL305aal86g01 |
| 0.12 | 2.65 | 88.9 | 7 | culturable kangaroo *Macropus giganteus* Eastern grey Kangaroo forestomach contents |
| 0.10 | 2.35 | 84.6 | 2 | *Caminicella sporogenes* str. AM1114 |
| 0.10 | 2.16 | 90.5 | 5 | *Coprobacillus cateniformis* str. JCM 10605 |
| 0.08 | 1.73 | 83.8 | 1 | mouse cecum clone SWPT19_aaa04g11 |
| 0.03 | 0.74 | 82.7 | 2 | human fecal clone RL197_aah85c11 |
| 0.02 | 0.50 | 88.3 | 2 | swine intestine clone p-2772-24E5 |
| 0.02 | 0.38 | 80.4 | 1 | *Eubacterium cylindroides* str. JCM 7786 |
| 0.01 | 0.26 | 87.1 | 2 | *Spiroplasma insolitum* str. ATCC 33502; M55 |
| 0.01 | 0.25 | 89.2 | 3 | human fecal clone RL117_aae92d08 |
| 0.01 | 0.21 | 94.0 | 7 | *Eubacterium* sp. Pei061 |
| 0.01 | 0.18 | 82.0 | 1 | sediment-free PCB-dechlorinating enrichment culture clone JN18_A14_H |
| 0.01 | 0.16 | 88.2 | 2 | mesophilic anaerobic digester clone G35_D8_H_B_E07 |
| 0.004 | 0.10 | 84.7 | 1 | human fecal clone RL179aan75d04 |
| 0.004 | 0.09 | 86.0 | 1 | *Catenibacterium mitsuokai* str. JCM 10609 |
| 0.003 | 0.08 | 87.0 | 1 | human fecal clone RL200_aai60f02 |
| 0.003 | 0.07 | 84.2 | 1 | Electricigen Enrichment MFC full-scale anaerobic bioreactor sludge treating brewery waste clone 31a07 |
| 0.003 | 0.06 | 86.2 | 1 | Inhibition nitrate reduction chromium (VI) microcosms heavy metal contaminated anaerobic soil microcosm isolate GNCr-2GNCr-2 str. GNCr-2 |
| 0.002 | 0.04 | 87.2 | 1 | *Enterococcus mundtii* str. NFRI 7393 |
| 0.001 | 0.02 | 91.7 | 1 | human fecal clone RL176_aan58b04 |
| 0.004 | 0.02 | 88.8 | 1 | mouse cecum clone M2_d06 |
| 4.46 | 100.00 | | 109 | ← Total |

Figure 12:
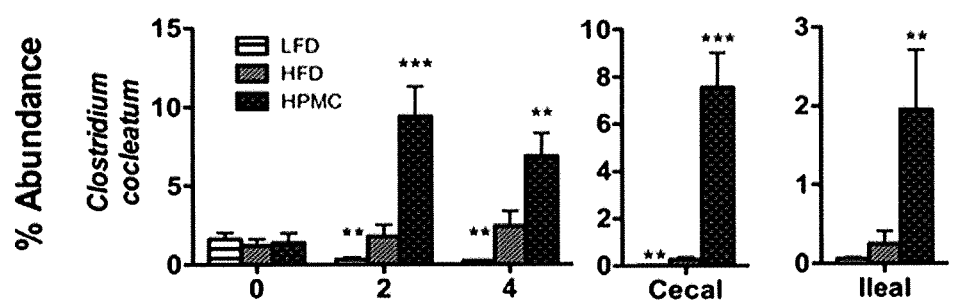
FIG. 12 shows mean relative abundance of the combined 59 OTUs with a closest match to *Clostridium cocleatum* in fecal 0 week, 2 week, 4 week, and 4-week cecal and ileal samples. * p<0.05,  p<0.01, * p<0.001. Mann-Whitney U Test.
Figure 13:
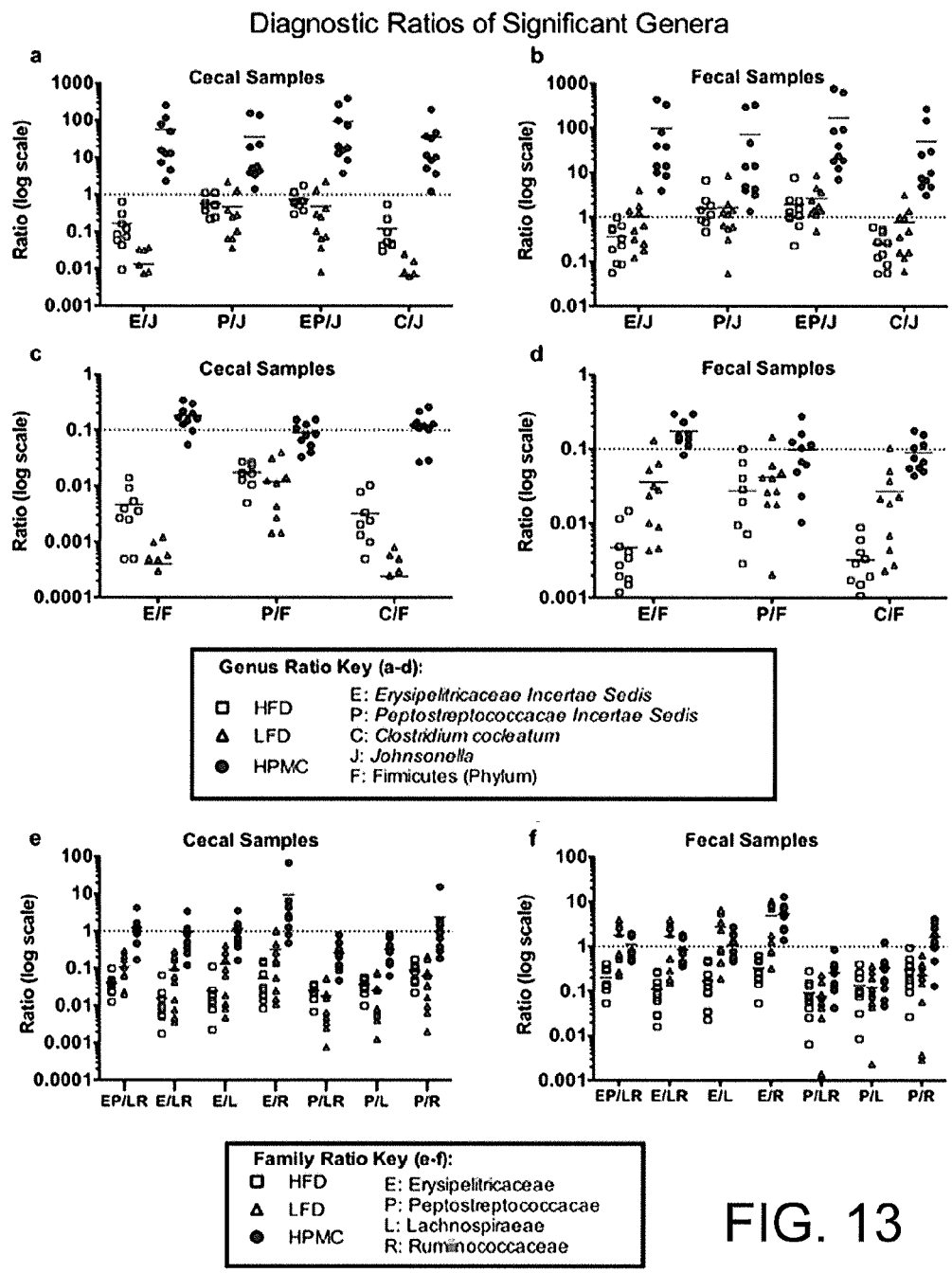
FIGS. 13a-13f is a scatter plot of ratios based on Qiime bioinformatic pipeline that represent diagnostic criteria for predicting predisposition to weight gain on a high fat diet and effectiveness of fiber treatment for weight loss or weight gain prevention for 4-week cecal (a, c, e) and 4-week fecal (b, d, f). a-b). Ratios at the genus level are calculated by dividing the sum of any combination of Erysipelotrichaceae Incertae Sedis, Peptostreptococcaceae Incertae Sedis, and/or *Clostridium cocleatum* by *Johnsonella*. A ratio below 1 indicates a state that is predisposed to weight gain while a ratio above 1 indicates a state that has a high propensity to prevent weight gain. c-d). Additional ratios are calculated by dividing the sum of any combination of Erysipelotrichaceae Incertae Sedis, Peptostreptococcaceae Incertae Sedis, and/or *Clostridium cocleatum* by the phylum Firmicutes to measure the relative abundance. A ratio below 0.1 indicates a state that is predisposed to weight gain while a ratio above 0.1 indicates a state that has a high propensity to prevent weight gain. e-f). Ratios at the family level are calculated by dividing the sum of any combination of Erysipelotrichaceae and/or Peptostreptococcacea by Lachnospiraceae and/or Ruminococcaceae. A ratio below 0.1 indicates a state that is predisposed to weight gain while a ratio above 0.1 indicates a state that has a high propensity to prevent weight gain.

Erysipelotricaceae Incertae Sedis (EIS) is a taxon of interest because it is increased significantly in the HPMC-treated mice (FIG. 12). To investigate the potential identity of members of EIS, the 109 unique sequences assigned to EIS at the OTU level were aligned using Greengenes to find the nearest neighbor. Minimum length was set at 100 nucleotides and Conclusions The present study demonstrates that reducing dietary fat, or adding dietary fiber improves markers of metabolic health in mice receiving a high-calorie/high-fat diet. In particular, this study shows that adding HPMC disrupts a strong relationship between energy intake and weight change. One explanation for the observed deviation may be the increased excretion of bile salts and fats in the feces induced by HPMC, representing a form of energy wasting. As shown herein, changing from HFD to a LFD, or adding 10% HPMC to HFD resulted in marked shifts in the intestinal microbiota over a 4-week period, providing evidence that HPMC alters the intestinal microbiota. The results are highly consistent within the experimental groups and show progressive changes in the microbiota sampled in the feces, with consistent shifts in the cecal and ileal samples collected at sacrifice.

HPMC and LFD both improve metabolic health and shape the microbiome, however linkages between specific microbial taxa and host metabolic phenotypes could only be identified in HPMC treated mice and not in LFD mice. This dichotomy suggests that the improvement in health by HPMC is mediated by the intestinal microbiota, while health benefits achieved by LFD are independent of gut microbes. Since HPMC is assumed to be inert, and not acted on by intestinal microbiota, how could this be achieved?

One possible mechanism of action related to HPMC effects on the gut microbiome could be the reduction in microbial load. Although changing from HFD to LFD did not affect total bacterial densities, adding HPMC clearly had a lowering effect and modulated overall composition as observed in essentially every analysis. Although ecological richness showed no changes at higher taxonomic orders, richness of the HPMC-impacted intestinal community and evenness at the OTU (species) level declined. Such dynamics are consistent with HPMC selection for a small group of specialist organisms that are over-represented at the expense of the usual community members.

The extent of the dynamics swings, as detailed in studies of community structure that are based on phylogenetic relationships among the taxa and shown by PCA presentations of the Unifrac analyses (FIGS. 16-17) and by heat map (FIG. 18) indicate HPMC-induced progressive shifts in community structure in fecal, as well as in cecal, populations. Changing from HFD to LFD also produces shifts in community composition, but in ways that differ from the HPMC-induced shifts.

All of the major HPMC-induced shifts involve families within Firmicutes, with major decreases in Lachnospiraceae and Ruminococcaceae, and increases in Erysipelotrichaceae and Peptostreptococcaceae (FIG. 10). That Firmicutes but not Bacteroidetes are affected indicates differences in their functional or anatomic niches worth future exploration; in this sense, HPMC treatment is a probe of intestinal microbiome population structure. Based on the multiple specimens obtained from mice receiving the HFD, there are conserved numerical relationships among order-level taxa (FIG. 20) that are disrupted after HPMC is added. Informatic analysis indicated conserved patterns of co-variance among major taxa in the baseline and continuing HFD mice. Importantly, change to HMPC and LFD diet ablated the prior co-variances, and a new relationship was established in LFD mice.

Figure 21:
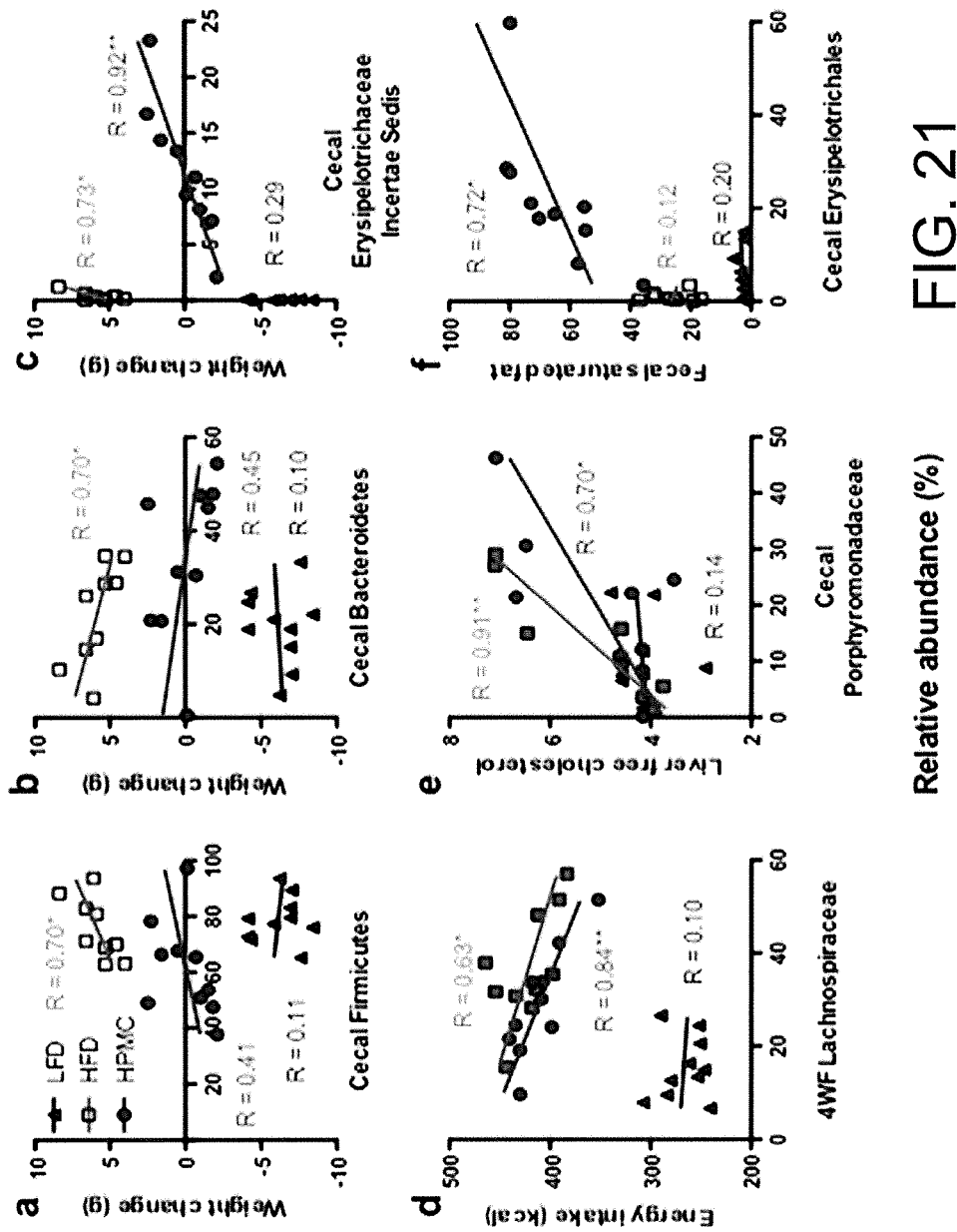
FIGS. 21a-21f show significant relationships between taxa and host phenotype, conditioned on dietary intervention. Metabolic parameters for mice on the three different diets, LFD (triangle), HFD (square), and HPMC (circle) were examined with respect to relative abundance of taxa, and the correlation constant (R) from linear regression analysis shown. Top panels represent weight change vs. cecal Firmicutes (a), cecal Bacteroidetes (b), and cecal Erysipelotrichaceae Incertae Sedis (c). Bottom panels represent energy intake vs. 4 week fecal Lachnospiraceae (d), liver free cholesterol vs. cecal Porphyromonadaceae (e), and fecal saturated fat vs. cecal Erysipelotrichaceae (f). * p<0.05,  p<0.01, * p<0.001 for a non-zero slope.

Importantly from this work, we now identify specific taxa that are associated with weight gain (e.g. Erysipelotrichaceae Incertae Sedis (EIS)), and with other metabolic phenotypes (FIG. 21 Tables 4-5).

Without wishing to be bound by a specific theory, HPMC could alter the microbial ecosystem in several ways: (i) HPMC may bind to mucus glycoproteins22-24 and swell in the large intestine, potentially displacing mucosa-associated microbiota. (ii) HPMC may sequester glycoside hydrolases or other catalytic enzymes, by mimicking the carbohydrate structures to which they bind, decreasing microbiome capacity for energy harvest from complex carbohydrates (for example, HPMC, resembling the structural subunit of amylase, has been used to trap and recover (3-amylase from *Clostridium* thermosulfurongenes25), and (iii) such sequestration may affect the balance between bile salt excretion and reabsorption affecting cholesterol and fat excretion. (iv) HPMC may be partially fermented in the intestine, stimulating the growth of organisms that digest cellulose or secondary metabolites from HPMC.

Example 3

Testing of Probiotic Compositions of the Invention in Mouse Models

Methods and Abbreviations

Abbreviations.
All abbreviations also apply to FIGS. 22-24. CSHEPCc=at least one of *Coprobacillus, Sporacetigenium, Holdemania*. JO=at least one of *Johnsonella, Oscillibacter*. Prebiotic=at least one of trehalose, cellobose, maltose, mannose, sucrose, lactose, salicin, mellibiose, raffinose, galactose, and fructose. C57B6 mice=C57/B16J mice (approximately 2 months old in the beginning of the experiment).

Figure 22:
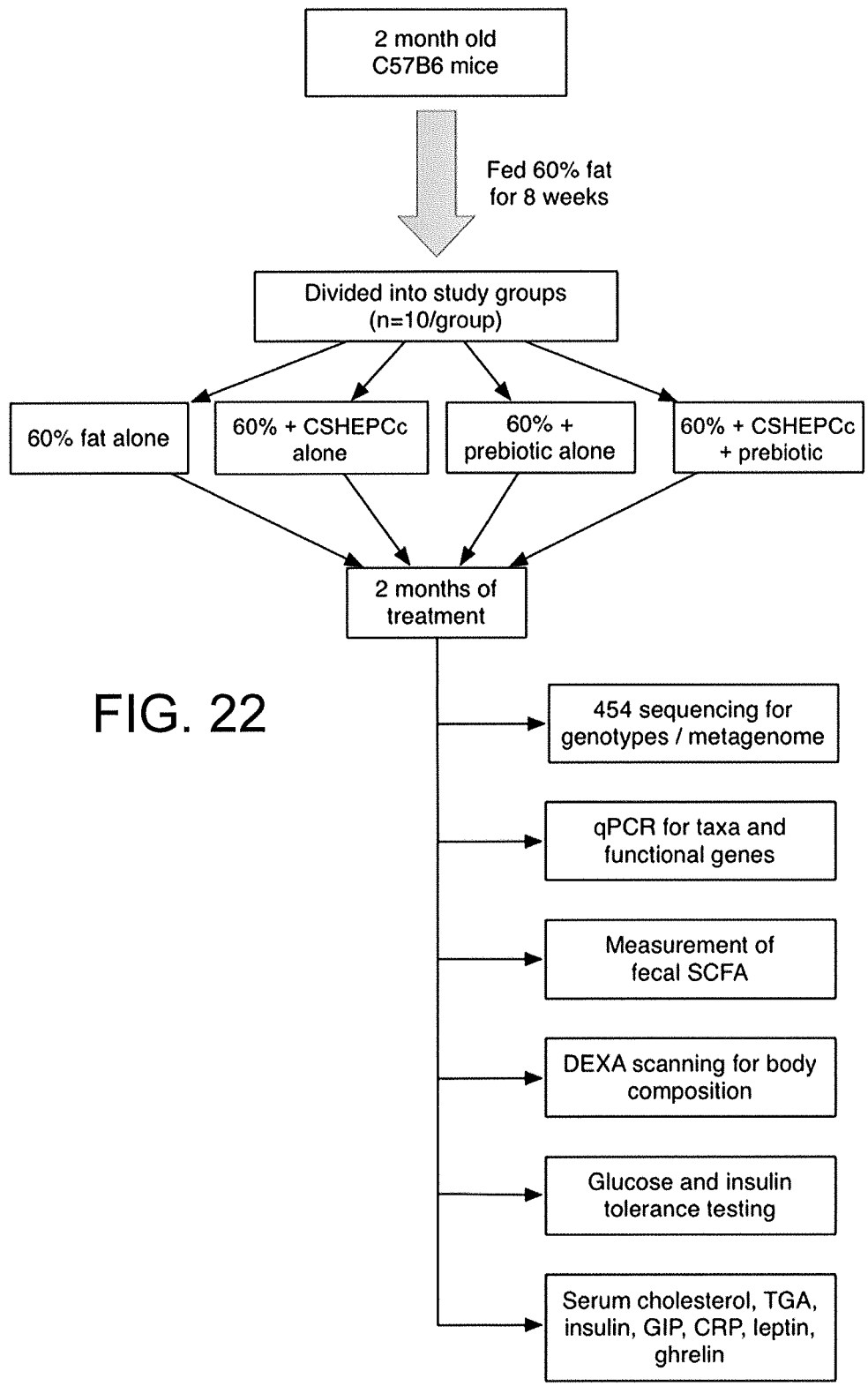
FIG. 22 is an outline of experiments directed to comparing the effect of diet-induced obesity (DIO) diet on control mice, mice exposed to at least one of *Coprobacillus, Sporacetigenium, Holdemania*, Erysipelotrichaceae Incertae Sedis, Peptostreptococaceae Incertae Sedis, and *Clostridium cocleatum* (CSHEPCc) or prebiotics alone, or mice exposed to CSHEPCc and prebiotics simultaneously.

3.1 Determination of the Effect of CSHEPCc and/or Prebiotic Treatment on Weight Gain in a DIO Mouse Model As schematically shown in FIG. 22, four groups of C57/B16J mice (at least 10 mice in each group) are fed 60% fat (DIO) diet from two months to four months of age. At four months of age, group 1 is kept untreated (control), group 2 gets CSHEPCc delivered by gastric gavage (*Coprobacillus, Holdemania*, and Peptostreptococcacea Incertae Sedis are delivered as live cells, *Sporacetigenium*, Erysipelotrichaceae Incertae Sedis, and *Clostridium cocleatum* are delivered as spores; at a dose of $10^9$ cells each week), group 3 gets prebiotic only (at a dose of 10 g/L in the drinking water every day), group 4 gets CSHEPCc+Prebiotic.

Measurements:
Genotype: qPCRs for Eubacteria, Firmicutes, Bacteroidetes, BCoAT, and individual qPCRs for C, S, H, E, P, Cc, J, O
Phenotype: weight every week, fasting glucose, oral glucose tolerance test, insulin tolerance test, total cholesterol, LDL, HDL, triglycerides (TGA), dual emission X-ray absorptiometry (DEXA) every 2 weeks to examine total weight, lean composition, bone mineral density, and fat composition (and percent fat); fecal short-chain fatty acids (SCFA), including butyrate and acetate); fasting serum leptin, ghrelin, insulin, GIP (glucose-dependent insulinotropic peptide), CRP (C-Reactive Protein).

Figure 23:
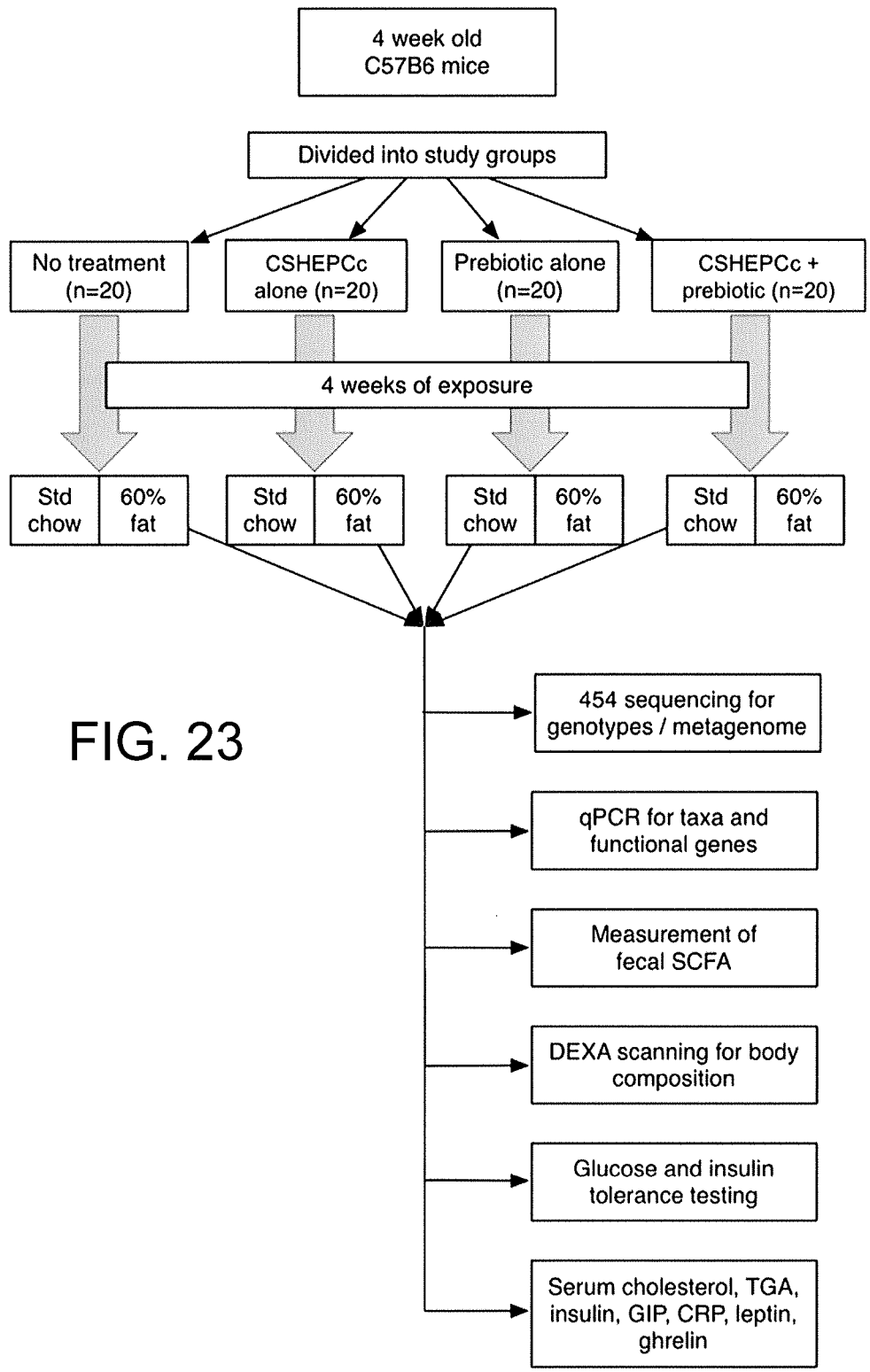
FIG. 23 is an outline of experiments directed to evaluating the effects of prophylactic exposure to *Coprobacillus, Sporacetigenium, Holdemania*, Erysipelotrichaceae Incertae Sedis, Peptostreptococaceae Incertae Sedis, and *Clostridium cocleatum* (CSHEPCc), and/or prebiotics. In this experiment, the mice are exposed to nothing (controls), CSHEPCc or prebiotics alone, or CSHEPCc and prebiotics upon weaning. After 4 weeks, they are given either high fat or regular chow to see the effects of the prophylactic exposure.

3.2 Determination of the Effect of CSHEPCc and/or Prebiotic Treatment on Preventing Obesity in a DIO Mouse Model As shown in FIG. 23, in this experiment, eighty (80) C57/B16J mice are fed 10% fat diet until they are two months old. At four weeks of age (while on 10% diet), mice are divided into four treatment groups: group 1 is kept untreated (control), group 2 gets CSH delivered by gastric gavage (*Coprobacillus, Holdemania*, and Peptostreptococcaceae are delivered as live cells, *Sporacetigenium*, Erysipelotrichaceae Incertae Sedis, and *Clostridium cocleatum* are delivered as spores; at a dose of $10^9$ cells of each every week), group 3 gets prebiotic only (at a dose of 10 g/L in the drinking water every day), group 4 gets CSHEPCc+Prebiotic. At two months of life, half of the mice (10 mice) in each treatment group are switched to 60% DIO diet, and half of the mice (10 mice) are kept on 10% diet. The same genotypes and phenotype parameters are measured as specified in section 3.1, above.

Figure 24:
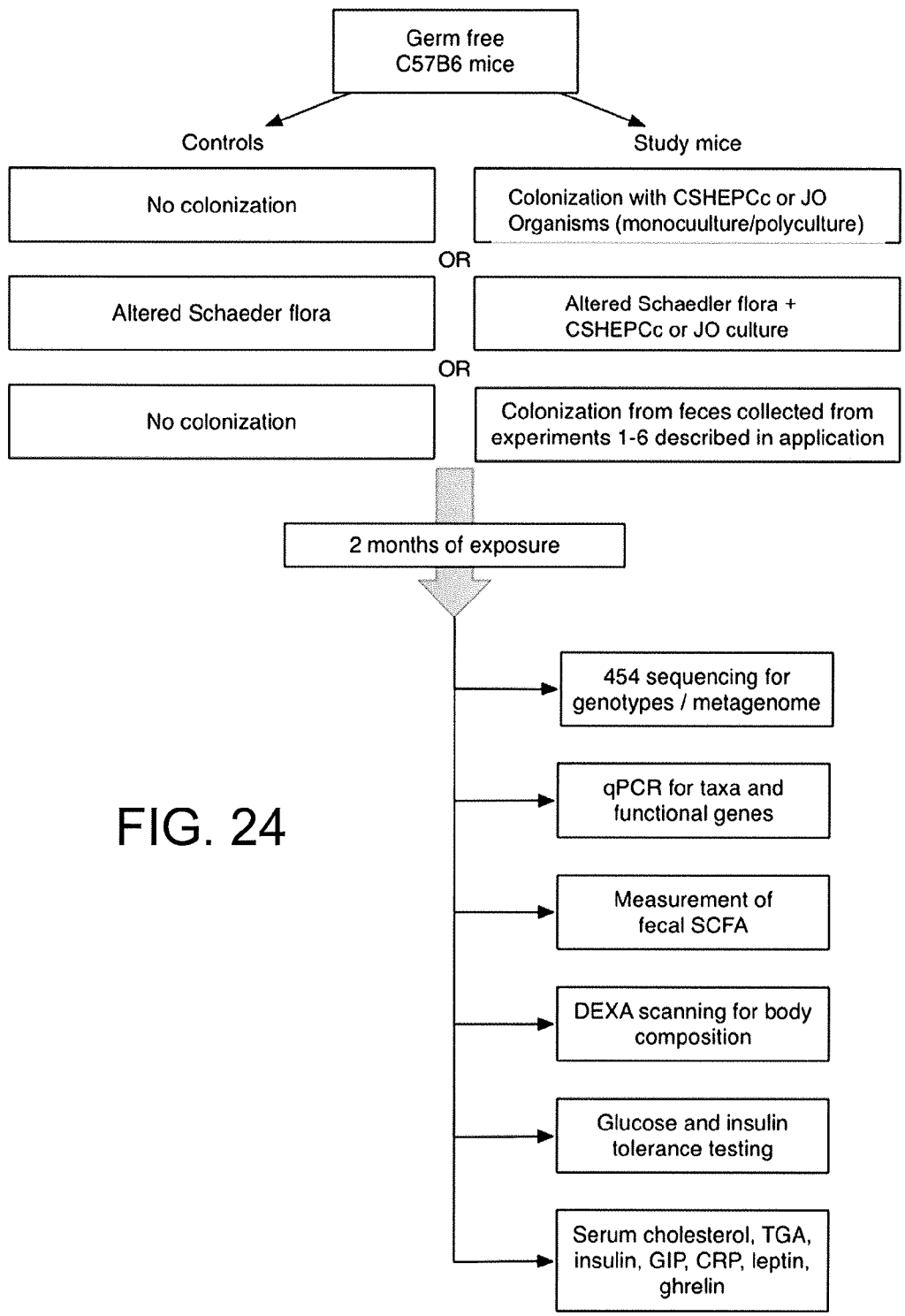
FIG. 24 is an outline of experiments directed to determining the effects of specific colonizations in germ-free mice. There are three potential types of studies summarized here, comparing different control and study groups. JO is at least one of *Johnsonella* and *Oscillibacter*; CSHEPCc is at least one of *Coprobacillus, Sporacetigenium, Holdemania*, Erysipelotrichaceae Incertae Sedis, Peptostreptococaceae Incertae Sedis, and *Clostridium cocleatum*.

3.3 Determination of the Effect of JO and/or CSHEPCc Treatment on Weight Gain and Prevention of Obesity in a Germ-Free Mouse Model As shown in FIG. 24, in this experiment, germ-free (GF) C57/Black 6 mice are generated and treated with: (1) CSHEPCc as monocultures (one, two, three, or four organisms at a time) or with JO as monocultures (J or O); (2) altered Schaedler flora (ASF) which consists of eight common mouse intestinal commensal bacteria which were developed to colonize germ-free mice and to establish a uniform baseline of conventionally colonized mice (Dewhirst et at., Appl. Environ. Microbiol., 1999, 65:3287-3292) followed by introduction of CSHEPCc as monocultures or JO (J or O), or nothing (control); (3) feces from normal mice treated with CSHEPCc or control untreated normal mice. From two months of age to four months of age, mice are fed a 10% fat diet. At four months of age, half of the mice (10 mice) in each treatment group are switched to the 60% DIO diet, and half of the mice (10 mice) are kept on the 10% diet. The same genotypes and phenotype parameters are measured as specified in section 3.2, above.

REFERENCES

1. Reppas, C., Swidan, S. Z., Tobey, S. W., Turowski, M. & Dressman, J. B. Hydroxypropylmethylcellulose significantly lowers blood cholesterol in mildly hypercholesterolemic human subjects. *Europ J Clin Nutri* 63, 71-77 (2009). (Need better ref)
2. Carr, T., Gallaher, D., Yang, C. & Hassel, C. Increased intestinal contents viscosity reduces cholesterol absorption efficiency in hamsters fed hydroxypropyl methylcellulose. *J of Nutri* 126, 1463 (1996). (Need better ref)
3. Gallaher, D., Hassel, C. & Lee, K. Relationships between viscosity of hydroxypropyl methylcellulose and plasma cholesterol in hamsters. *J of Nutri* 123, 1732 (1993).
4. Maki, K. C., et al. High-viscosity hydroxypropylmethylcellulose blunts postprandial glucose and insulin responses. *Diabetes Care* 30, 1039-1043 (2007).
5. Maki, K. C., et al. Dose-response characteristics of high-viscosity hydroxypropylmethylcellulose in subjects at risk for the development of type 2 diabetes mellitus. *Diabetes Technol Ther* 11, 119-125 (2009).
6. Maki, K. C., et al. Hydroxypropylmethylcellulose and methylcellulose consumption reduce postprandial insulinemia in overweight and obese men and women. *J Nutr* 138, 292-296 (2008).
7. Qin, J., et al. A human gut microbial gene catalogue established by metagenomic sequencing. *Nature* 464, 59-65 (2010).
8. Wong, J. M. W., de Souza, R., Kendall, C. W. C., Emam, A. & Jenkins, D. J. A. Colonic health: fermentation and short chain fatty acids. *Journal of Clinical Gastroenterology* 40, 235-243 (2006).
9. Louis, P., et al. Restricted distribution of the butyrate kinase pathway among butyrate-producing bacteria from the human colon. *Journal of Bacteriology* 186, 2099-2106 (2004).
10. Savage, D. C. Microbial ecology of the gastrointestinal tract. *Annu Rev Microbiol* 31, 107-133 (1977).
11. Turnbaugh, P. J., et al. An obesity-associated gut microbiome with increased capacity for energy harvest. *Nature* 444, 1027-1131 (2006).
12. Savage, D. C. Gastrointestinal microflora in mammalian nutrition. *Annu Rev Nutr* 6, 155-178 (1986).
13. Siepmann, J. & Peppas, N. A. Modeling of drug release from delivery systems based on hydroxypropyl methylcellulose (HPMC). *Adv Drug Deliv Rev* 48, 139-157 (2001).
14. Gallaher, D. D., Hassel, C. A., Lee, K. J. & Gallaher, C. M. Viscosity and fermentability as attributes of dietary fiber responsible for the hypocholesterolemic effect in hamsters. *J Nutr* 123, 244-252 (1993).
15. Hung, S.-C., et al. Dietary fiber improves lipid homeostasis and modulates adipocytokines in hamsters. *J Diabetes* 1, 194-206 (2009).
16. Topping, D. Hydroxypropylmethylcellulose, viscosity, and plasma cholesterol control. *Nutr Rev* 52, 176-178 (1994).
17. Cook, S. I. & Sellin, J. H. Review article: short chain fatty acids in health and disease. *Aliment Pharmacol Ther* 12, 499-507 (1998).
18. Braun, W. H., Ramsey, J. C. & Gehring, P. J. The lack of significant absorption of methylcellulose, viscosity 3300 CP, from the gastrointestinal tract following single and multiple oral doses to the rat. *Food Cosmet Toxicol* 12, 373-376 (1974).
19. Machle, W., Heyroth, F. & Witherup, S. The Fate of Methylcellulose in the Human Digestive Tract. 1-9 (1944).
20. Yokoyama, W., Knuckles, B., Davis, P. & Daggy, B. Stability of ingested methylcellulose in the rat determined by polymer molar mass measurements by light scattering. *Journal of agricultural and food chemistry* 50, 7726-7730 (2002).
21. Ferguson, M. & Jones, G. Production of short chain fatty acids following in vitro fermentation of saccharides, saccharide esters, fructo oligosaccharides, starches, modified starches and non starch polysaccharides. *Journal of the Science of Food and Agriculture* 80, 166-170 (2000).
22. Cai, X., Yang, L., Zhang, L.-M. & Wu, Q. Synthesis and anaerobic biodegradation of indomethacin-conjugated cellulose ethers used for colon-specific drug delivery. *Bioresource Technology* 100, 4164-4170 (2009).
23. Haupt, S. & Rubinstein, A. The colon as a possible target for orally administered peptide and protein drugs. *Critical reviews in therapeutic drug carrier systems* 19, 499 (2002).
24. Hamman, J. H., Enslin, G. M. & Kotze, A. F. Oral delivery of peptide drugs: barriers and developments. *BioDrugs* 19, 165-177 (2005).
25. Miranda, E. & Berglund, K. Recovery of *Clostridium* thermosulfurogenes produced. beta.-amylase by hydroxypropyl methylcellulose partition. *Biotechnology Progress* 6, 214-219 (1990).
26. Clark, J., et al. Guide for the care and use of laboratory animals. Institute of Laboratory Animal Resources, National Research Council, Washington, D.C. (1996).
27. AOCS. Preparation of methyl esters of long-chain fatty acids from sampling analysis of commercial fats and oils. *Official method, AOCS*, Champaign, Ill. Ce 2-66 (1997).
28. Hong, Y. J., Turowski, M., Lin, J. T. & Yokoyama, W. H. Simultaneous characterization of bile acid, sterols, and determination of acylglycerides in feces from soluble cellulose-fed hamsters using HPLC with evaporative light-scattering detection and APCIñMS. *Journal of agricultural and food chemistry* 55, 9750-9757 (2007).

29. Caporaso, J. G., et al. QIIME allows analysis of high-throughput community sequencing data. *Nat Methods* 7, 335-336 (2010).
30. Lozupone, C., Lladser, M. E., Knights, D., Stombaugh, J. & Knight, R. UniFrac: an effective distance metric for microbial community comparison. *ISME J*(2010).
31. Lozupone, C. & Knight, R. UniFrac: a new phylogenetic method for comparing microbial communities. *Appl Environ Microbiol* 71, 8228-8235 (2005).
32. R: A Language and Environment for Statistical Computing. in *R Foundation for Statistical Computing*, Vol. 1 (R Foundation for Statistical Computing, 2009).
33. Gentleman, R. C., et al. Bioconductor: open software development for computational biology and bioinformatics. *Genome Biol* 5, R80 (2004).
34. Arumugam M, Raes J, Pelletier E, Le Paslier D, et al. Enterotypes of the human gut microbiome. *Nature* 2011; 473:174-80.
35. Muegge B D, Kuczynski J, Knights D, Clemente J C, González A, Fontana L, Henrissat B, Knight R, Gordon J I. Diet drives convergence in gut microbiome functions across mammalian phylogeny and within humans. Science 2011; 332:970-4.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

---

What is claimed:

1. A method for preventing weight gain in a mammal in need thereof comprising administering to the mammal a therapeutically effective amount of a probiotic composition comprising at least one strain from the genus *Dorea*.

2. The method of claim 1, wherein said strain is selected from the group consisting of live bacterial strains, spores and conditionally lethal bacterial strains.

3. The method of claim 1, wherein the probiotic composition is administered conjointly with a prebiotic composition which stimulates growth and/or metabolic activity of bacteria contained in the probiotic composition.

4. The method of claim 3, wherein the probiotic and prebiotic compositions are administered in one composition, or simultaneously as two separate compositions, or sequentially.

5. The method of claim 1, wherein the probiotic composition is administered orally or rectally.

6. The method of claim 1, wherein the probiotic composition is administered in a form of a capsule or in a form of a suppository.

7. The method of claim 1, wherein the mammal is human.

* * * * *

SEQUENCE LISTING

```
<160> NUMBER OF SEQ ID NOS: 13

<210> SEQ ID NO 1
<211> LENGTH: 17
<212> TYPE: DNA
<213> ORGANISM: Artificial Sequence
<220> FEATURE:
<223> OTHER INFORMATION: PCR primer

<400> SEQUENCE: 1
cagcagccgc ggtrata                                                  17

<210> SEQ ID NO 2
<211> LENGTH: 22
<212> TYPE: DNA
<213> ORGANISM: Artificial Sequence
<220> FEATURE:
<223> OTHER INFORMATION: PCR primer

<400> SEQUENCE: 2
ggactaccvg ggtatctaak cc                                            22

<210> SEQ ID NO 3
<211> LENGTH: 25
<212> TYPE: DNA
<213> ORGANISM: Artificial Sequence
<220> FEATURE:
<223> OTHER INFORMATION: PCR primer

<400> SEQUENCE: 3
ggagyatgtg gtttaattcg aagca                                         25

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
agctgacgac aaccatgcac                                               20

<210> SEQ ID NO 5
<211> LENGTH: 25
<212> TYPE: DNA
<213> ORGANISM: Artificial Sequence
<220> FEATURE:
```

```
<223> OTHER INFORMATION: PCR primer

<400> SEQUENCE: 5
ggarcatgtg gtttaattcg atgat                                          25

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
agctgacgac aaccatgcag                                                20

<210> SEQ ID NO 7
<211> LENGTH: 22
<212> TYPE: DNA
<213> ORGANISM: Artificial Sequence
<220> FEATURE:
<223> OTHER INFORMATION: PCR primer

<400> SEQUENCE: 7
ctyggtcatt tagaggaagt aa                                             22

<210> SEQ ID NO 8
<211> LENGTH: 19
<212> TYPE: DNA
<213> ORGANISM: Artificial Sequence
<220> FEATURE:
<223> OTHER INFORMATION: PCR primer

<400> SEQUENCE: 8
rctgcgttct tcatcgwtg                                                 19

<210> SEQ ID NO 9
<211> LENGTH: 19
<212> TYPE: DNA
<213> ORGANISM: Artificial Sequence
<220> FEATURE:
<223> OTHER INFORMATION: Probe

<400> SEQUENCE: 9
tcygtaggtg aacctgcrg                                                 19

<210> SEQ ID NO 10
<211> LENGTH: 29
<212> TYPE: DNA
<213> ORGANISM: Artificial Sequence
<220> FEATURE:
<223> OTHER INFORMATION: PCR primer

<400> SEQUENCE: 10
gcgacatttc actggaayws tggcayatg                                      29

<210> SEQ ID NO 11
<211> LENGTH: 25
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: 23
<223> OTHER INFORMATION: n = A,T,C or G

<400> SEQUENCE: 11
```

```
cctgcctttg caatrtcacr aangc                                              25

<210> SEQ ID NO 12
<211> LENGTH: 17
<212> TYPE: DNA
<213> ORGANISM: Artificial Sequence
<220> FEATURE:
<223> OTHER INFORMATION: PCR primer

<400> SEQUENCE: 12
cctacgggag gcagcag                                                       17

<210> SEQ ID NO 13
<211> LENGTH: 18
<212> TYPE: DNA
<213> ORGANISM: Artificial Sequence
<220> FEATURE:
<223> OTHER INFORMATION: PCR primer

<400> SEQUENCE: 13
ccgtcaattc mtttragt                                                      18
```